(12) United States Patent
Leung

(10) Patent No.: US 11,976,116 B2
(45) Date of Patent: May 7, 2024

(54) SALVAGE CHIMERIC ANTIGEN RECEPTOR SYSTEMS

(71) Applicant: 2seventy bio, Inc., Cambridge, MA (US)

(72) Inventor: Wai-Hang Leung, Seattle, WA (US)

(73) Assignee: 2SEVENTY BIO, INC., Cambridge, MA (US)

( * ) Notice: Subject to any disclaimer, the term of this patent is extended or adjusted under 35 U.S.C. 154(b) by 1559 days.

(21) Appl. No.: 16/092,946

(22) PCT Filed: Apr. 14, 2017

(86) PCT No.: PCT/US2017/027606
§ 371 (c)(1),
(2) Date: Oct. 11, 2018

(87) PCT Pub. No.: WO2017/180993
PCT Pub. Date: Oct. 19, 2017

(65) Prior Publication Data
US 2022/0195039 A1   Jun. 23, 2022

Related U.S. Application Data

(60) Provisional application No. 62/356,335, filed on Jun. 29, 2016, provisional application No. 62/322,634, filed on Apr. 14, 2016.

(51) Int. Cl.
| | |
|---|---|
| *C07K 16/28* | (2006.01) |
| *A61K 35/17* | (2015.01) |
| *C07K 14/705* | (2006.01) |
| *C07K 14/725* | (2006.01) |

(52) U.S. Cl.
CPC .......... *C07K 16/2803* (2013.01); *A61K 35/17* (2013.01); *C07K 14/7051* (2013.01); *C07K 14/70517* (2013.01); *C07K 14/70578* (2013.01); *C07K 2317/622* (2013.01); *C07K 2319/02* (2013.01); *C07K 2319/03* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 5,858,358 A | 1/1999 | June et al. | |
| 5,883,223 A | 3/1999 | Gray | |
| 5,994,136 A | 11/1999 | Naldini et al. | |
| 6,005,079 A | 12/1999 | Casterman et al. | |
| 6,013,516 A | 1/2000 | Verma et al. | |
| 6,352,694 B1 | 3/2002 | June et al. | |
| 6,534,055 B1 | 3/2003 | June et al. | |
| 6,649,595 B2 | 11/2003 | Clackson et al. | |
| 6,682,907 B1 | 1/2004 | Charneau et al. | |
| 6,692,964 B1 | 2/2004 | June et al. | |
| 6,797,514 B2 | 9/2004 | Berenson et al. | |
| 6,867,041 B2 | 3/2005 | Berenson et al. | |
| 6,887,466 B2 | 5/2005 | June et al. | |
| 6,905,680 B2 | 6/2005 | June et al. | |
| 6,905,681 B1 | 6/2005 | June et al. | |
| 6,905,874 B2 | 6/2005 | Seo | |
| 7,067,318 B2 | 6/2006 | June et al. | |
| 7,144,575 B2 | 12/2006 | June et al. | |
| 7,172,869 B2 | 2/2007 | June et al. | |
| 7,175,843 B2 | 2/2007 | June et al. | |
| 7,232,566 B2 | 6/2007 | June et al. | |
| 2003/0147869 A1 | 8/2003 | Riley et al. | |
| 2015/0266973 A1 | 9/2015 | Jarjour et al. | |
| 2015/0368342 A1 | 12/2015 | Wu et al. | |
| 2017/0081411 A1* | 3/2017 | Engels | A61K 38/177 |

FOREIGN PATENT DOCUMENTS

| | | | |
|---|---|---|---|
| EP | 0 404 097 | 12/1990 | |
| WO | WO 93/01161 | 1/1993 | |
| WO | WO 94/04678 | 3/1994 | |
| WO | WO 94/25591 | 11/1994 | |
| WO | WO 03/057171 | 7/2003 | |
| WO | WO 2006/010834 | 2/2006 | |
| WO | WO 2013/138505 | 9/2013 | |
| WO | WO-2014127261 A1 * | 8/2014 | A61K 35/17 |
| WO | WO 2015/142661 | 9/2015 | |

(Continued)

OTHER PUBLICATIONS

Extended European Search Report dated Nov. 5, 2019, for European Application No. 17783220.1, 12 pages.
Guest et al., "The role of extracellular spacer regions in the optimal design of chimeric immune receptors: evaluation of four different scFvs and antigens," J Immunother. May-Jun. 2005;28(3):203-11.
Huber et al., "Antibody structure," Trends in Biochemical Sciences, vol. 1, Issue 8, Aug. 1976, pp. 174-178.
Hudecek et al., "The nonsignaling extracellular spacer domain of chimeric antigen receptors is decisive for in vivo antitumor activity," Cancer Immunol Res. Feb. 2015;3(2):125-35.

(Continued)

*Primary Examiner* — Michael D Burkhart
(74) *Attorney, Agent, or Firm* — McCarter & English, LLP; Marcie B. Clarke; Dylan M. Blumenthal

(57) ABSTRACT

The invention provides improved compositions for adoptive cell therapies for cancers. The invention generally provides improved vectors for generating T cell therapies and methods of using the same. More particularly, the invention provides salvage CARs, dimerizable salvage receptors, and their use in treating, preventing, or ameliorating cancers, and in particular preferred embodiments relapsed or refractory cancer. In various embodiments, a salvage chimeric antigen receptor (CAR) is provided comprising: an extracellular antigen binding domain; a multimerization domain; a transmembrane domain; one or more intracellular co-stimulatory signaling domains; and/or a primary signaling domain.

14 Claims, 9 Drawing Sheets
Specification includes a Sequence Listing.

(56) References Cited

FOREIGN PATENT DOCUMENTS

| WO | WO 2015/150771 | 10/2015 |
|---|---|---|
| WO | WO 2016/014576 | 1/2016 |
| WO | WO 2016/014789 | 1/2016 |
| WO | WO 2017/180993 | 10/2017 |

OTHER PUBLICATIONS

International Search Report and Written Opinion dated Jul. 14, 2017, for International Application No. PCT/US2017/027606, 13 pages.
Jonas V Schaefer et al: "Chapter 7: Miniantibodies", pp. 85-100, XP009188580.
Rheinnecker et al., "Multivalent antibody fragments with high functional affinity for a tumor-associated carbohydrate antigen," J Immunol. Oct. 1, 1996;157(7):2989-97.
Bird, Robert E., et al. "Single-chain antigen-binding proteins." Science (1988); 242.4877: 423-427.
Borden and Kabat, "Nucleotide sequence of the cDNAs encoding the variable region heavy and light chains of a myeloma protein specific for the terminal nonreducing end of alpha (1—6) dextran", Proc Natl Acad Sci U S A (1987); 84(8):2440-3.
Challita, P. et al., "Multiple modifications in cis elements of the long terminal repeat of retroviral vectors lead to increased expression and decreased DNA methylation in embryonic carcinoma cells." J Virol. (1995); 69(2): 748-755.
Chaudhary, Vijay K., et al. "A rapid method of cloning functional variable-region antibody genes in *Escherichia coli* as single-chain immunotoxins." Proceedings of the National Academy of Sciences (1990); 87.3: 1066-1070 (and correction).
Chothia and Lesk, "Canonical structures for the hypervariable regions of immunoglobulins", J Mol Biol (1987); 196(4):901-917.
Chothia, C. et al., "Conformations of immunoglobulin hypervariable regions", Nature (1989); 342(6252):877-883.
Clever, J. et al., "RNA Secondary Structure and Binding Sites for gag Gene Products in the 5' Packaging Signal of Human Immunodeficiency Virus Type 1." J. of Virology (1995); 69(4): 2101-2109.
Cooper, Laurence JN, et al. "T-cell clones can be rendered specific for CD19: Toward the selective augmentation of the graft-versus-B—lineage leukemia effect." Blood (2003); 101.4: 1637-1644.
Cullen, B.R., "Human Immunodeficiency Virus as a Prototypic Complex Retrovirus", Journal of Virology (1991); 65(3): 1053-1056.
Cullen and Greene, "Regulatory Pathways Governing HIV-1 Replication", Cell (1989); 58: 423-426.
De Felipe, Pablo, and Ryan, Martin D. "Targeting of proteins derived from self-processing polyproteins containing multiple signal sequences." Traffic (2004); 5.8: 616-626.
Desjarlais, John R., and Berg, Jeremy M. "Use of a zinc-finger consensus sequence framework and specificity rules to design specific DNA binding proteins." Proceedings of the National Academy of Sciences (1993); 90.6: 2256-2260.
Desjarlais, John R., and Berg, Jeremy M. "Length-encoded multiplex binding site determination: application to zinc finger proteins." Proceedings of the National Academy of Sciences (1994); 91.23: 11099-11103.
Donnelly, M. et al., "The 'cleavage' activities of foot-and-mouth disease virus 2A site-directed mutants and naturally occurring '2A-like' sequences." J Gen Virol. (2001); 82 (Pt 5): 1027-1041.
Dull et al., "A third-generation lentivirus vector with a conditional packaging system", Journal of Virology (1998); 72(11): 8463-8671.
Holliger et al., ""Diabodies": small bivalent and bispecific antibody fragments," Proc Natl Acad Sci U S A. Jul. 15, 1993;90(14):6444-8.
Holt et al., "Domain antibodies: proteins for therapy," Trends Biotechnol. Nov. 2003;21(11):484-90.
Huang and Yen, "Role of the hepatitis B virus posttranscriptional regulatory element in export of intronless transcripts", Molecular and Cellular Biology (1995); 15(7): 3864-3869.

Hudson et al., "Engineered antibodies," Nat Med. Jan. 2003;9(1):129-34.
Kim, Yang-Gyun, et al. "Hybrid restriction enzymes: zinc finger fusions to Fok I cleavage domain." Proceedings of the National Academy of Sciences (1996); 93.3: 1156-1160.
Koch-Nolte et al., "Single domain antibodies from llama effectively and specifically block T cell ecto-ADP-ribosyltransferase ART2.2 in vivo," FASEB J. Nov. 2007; 21(13):3490-8. Epub Jun. 15, 2007.
Kozak, M., "Point mutations define a sequence flanking the AUG initiator codon that modulates translation by eukaryotic ribosomes", Cell (1986), 44(2):283-92.
Kozak, M., "An analysis of 5'-noncoding sequences from 699 vertebrate messenger RNAs", Nucleic Acids Res. (1987), 15(20):8125-48.
Kutner, et al., "Simplified production andconcentration of HIV-1-based lentiviral vectors using HYPERFlask vessels and anion exchange membrane chromatography", BMC Biotechnol. (2009); 9:10. p. 1-7.
Kutner et al., "Production, concentration and titration of pseudotyped HIV-1-based lentiviral vectors", Nature Protocols (2009); 4: 495-505.
Lee et al. "Safety and Response of Incorporating CD19 Chimeric Antigen Receptor T Cell Therapy in Typical Salvage Regimens for Children and Young Adults with Acute Lymphoblastic Leukemia," Blood, Dec. 3, 2015 (Dec. 3, 2015), vol. 126, No. 23, p. 684.
Liu et al., "Design of polydactyl zinc-finger proteins for unique addressing within complex genomes," Proc Natl Acad Sci U S A. May 27, 1997; 94(11):5525-30.
Liu and Mertz, "HnRNP L binds a cis-acting RNA sequence element that enables intron-dependent gene expression." Genes & Dev. (1995); 9: 1766-1780.
Naldini L. et al., "Efficient transfer, integration, and sustained long-term expression of the transgene in adult rat brains injected with a lentiviral vector", Proc Natl Acad Sci USA (1996); 93(21): 11382-11388.
Naldini, L. et al., "In vivo gene delivery and stable transduction of nondividing cells by a lentiviral vector", Science (1996); 272(5259): 263-267.
Naldini, L., "Lentiviruses as gene transfer agents for delivery to non-dividing cells", Curr Opin Biotechnol. (1998); 5: 457-463.
Orlandi et al., "Cloning immunoglobulin variable domains for expression by the polymerase chain reaction," Proc Natl Acad Sci U S A. May 1989;86(10):3833-7.
Patel, S. et al., "Impact of chimeric immune receptor extracellular protein domains on T cell function." Gene Ther (1999); 6(3): 412-419.
Pomerantz, Joel L., et al. "Structure-based design of transcription factors." Science (1995); 267.5194: 93-96.
Pluckthun, "Antibodies from *Escherichia coli*," The Pharmacology of Monoclonal Antibodies, vol. 113, Rosenburg and Moore eds., (Springer-Verlag, New York, 1994), pp. 269-315.
Riechmann et al., "Single domain antibodies: comparison of camel VH and camelised human VH domains," J Immunol Methods. Dec. 10, 1999;231(1-2):25-38.
Ryan, M. et al., "Virus-encoded proteinases of the picornavirus super-group." J Gen Virol. (1997); 78 (Pt 4): 699-723.
Szymczak, Andrea L., et al. "Correction of multi-gene deficiency in vivo using a single 'self-cleaving' 2A peptide-based retroviral vector." Nature Biotechnology (2004); 22.5: 589-594.
White, I. et al., "Comparison of the glycosyl-phosphatidylinositol cleavage/attachment site between mammalian cells and parasitic protozoa", J Cell Sci. (2000); 113 (Pt 4):721-727.
Whitelegg N & Rees AR, "WAM: an improved algorithm for modelling antibodies on the WEB," Protein Eng. Dec. 2000;13(12):819-24.
Whitelegg N & Rees AR, "Antibody variable regions: toward a unified modeling method," Methods Mol Biol. 2004;248:51-91.
Wu and Kabat, "An analysis of the sequences of the variable regions of Bence Jones proteins and myeloma light chains and their implications for antibody complementarity", J Exp Med., (1970) 132(2): 211-250.

(56) References Cited

OTHER PUBLICATIONS

Maguire, A.M. et al., "Safety and efficacy of gene transfer for Leber's congenital amaurosis", N Engl J Med. (2008), 358(21): 2240-2248.

Zennou, V. et al., "HIV-1 genome nuclear import is mediated by a central DNA flap." Cell (2000); 101(2): 173-185.

Zufferey et al., "Multiply attenuated lentiviral vector achieves efficient gene delivery in vivo", Nat Biotechnol. (1997), 15(9): 871-875.

Zufferey, R. et al., "Woodchuck hepatitis virus posttranscriptional regulatory element enhances expression of transgenes delivered by retroviral vectors." J Virol. (1999); 73(4): 2886-2892.

* cited by examiner

Targeting CD19⁺ cells

E:T ratio = 2:1 (against Nalm-6)

SALVAGE CHIMERIC ANTIGEN RECEPTOR SYSTEMS

CROSS REFERENCE TO RELATED APPLICATIONS

This application is the National Stage of International Application No. PCT/US2017/027606, filed Apr. 14, 2017, which claims the benefit under 35 U.S.C. § 119(e) of U.S. Provisional Application No. 62/356,335, filed Jun. 29, 2016, and U.S. Provisional Application No. 62/322,634, filed Apr. 14, 2016, each of which is incorporated by reference herein in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is BLBD_068_02WO_ST25.txt. The text file is 42 KB, was created on Apr. 14, 2017, and is being submitted electronically via EFS-Web, concurrent with the filing of the specification.

BACKGROUND

Technical Field

The present invention relates to improved compositions and methods for treating cancer. More particularly, the invention relates to cellular immunotherapy compositions and methods of using the same to treat cancer.

Description of the Related Art

Cancer is a significant health problem throughout the world. Based on rates from 2008-2010, 40.76% of men and women born today will be diagnosed with some form of cancer at some time during their lifetime. 20.37% of men will develop cancer between their 50th and 70th birthdays compared to 15.30% for women. On Jan. 1, 2010, in the United States there were approximately 13,027,914 men and women alive who had a history of cancer—6,078,974 men and 6,948,940 women. It is estimated that 1,660,290 men and women (854,790 men and 805,500 women) in the United States will be diagnosed with and 580,350 men and women will die of cancer of all sites in 2013. Howlader et al. 2013.

Although advances have been made in detection, prevention, and treatment of cancer, a universally successful therapeutic strategy has yet to be realized. The response of various forms of cancer treatment is mixed. Traditional methods of treating cancers, including chemotherapy and radiotherapy, have limited utility due to toxic side effects.

Immunotherapy with therapeutic antibodies have also provided limited success, due in part to poor pharmacokinetic profiles, rapid elimination of antibodies by serum proteases and filtration at the glomerulus, and limited penetration into the tumor site and expression levels of the target antigen on tumor cells. Attempts to use genetically modified cells expressing chimeric antigen receptors (CARs) have also met with limited success due to poor in vivo expansion of CAR T cells, rapid disappearance of the cells after infusion, disappointing clinical activity, and relapsed or refractory cancers.

BRIEF SUMMARY

The invention generally provides improved vectors for generating T cell therapies and methods of using the same. More particularly, the invention provides salvage CARs, dimerizable salvage receptors, and their use in treating, preventing, or ameliorating cancers, and in particular preferred embodiments relapsed or refractory cancer.

In various embodiments, a salvage chimeric antigen receptor (CAR) is provided comprising: an extracellular antigen binding domain; a multimerization domain; a transmembrane domain; one or more intracellular co-stimulatory signaling domains; and/or a primary signaling domain.

In various embodiments, a salvage chimeric antigen receptor (CAR) is provided comprising: an extracellular antigen binding domain; a transmembrane domain; a multimerization domain; one or more intracellular co-stimulatory signaling domains; and/or a primary signaling domain.

In particular embodiments, the salvage CAR further comprises the extracellular antigen binding domain comprises an antibody or antigen binding fragment thereof.

In some embodiments, the salvage CAR further comprises the antibody or antigen binding fragment is selected from the group consisting of: a Camel Ig, Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), and single-domain antibody (sdAb, Nanobody).

In additional embodiments, the antibody or antigen binding fragment is an scFv.

In certain embodiments, the extracellular antigen binding domain binds an antigen selected from the group consisting of: alpha folate receptor, 5T4, $\alpha_v\beta_6$ integrin, BCMA, B7-H3, B7-H6, CAIX, CD16, CD19, CD20, CD22, CD30, CD33, CD37, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, VEGFR2, and WT-1.

In particular embodiments, the salvage CAR further comprises the extracellular antigen binding domain binds an antigen selected from the group consisting of: BCMA, CD19, CSPG4, PSCA, ROR1, and TAG72.

In particular embodiments, the salvage CAR further comprises the extracellular antigen binding domain binds an antigen selected from the group consisting of: BCMA, CD19, CD20, CD22, CD23, CD33, CD37, CD52, CD80, and HLA-DR.

In certain embodiments, the extracellular antigen binding domain binds BCMA or CD19.

In some embodiments, the extracellular antigen binding domain binds an antigen expressed on a cancer cell.

In additional embodiments, the extracellular antigen binding domain binds an antigen expressed on a solid cancer cell.

In some embodiments, the extracellular antigen binding domain binds an antigen expressed on a liquid cancer cell.

In particular embodiments, the salvage CAR further comprises the extracellular antigen binding domain binds an antigen expressed on a malignant B cell.

In further embodiments, the extracellular antigen binding domain binds an antigen expressed on a malignant plasma cell.

In particular embodiments, the salvage CAR further comprises the multimization domain is selected from the group consisting of: an FKBP polypeptide, an FRB polypeptide, a calcineurin polypeptide, a cyclophilin polypeptide, a bacterial DHFR polypeptide, a PYL1 polypeptide, an ABI1 polypeptide, a GIB1 polypeptide, a GAI polypeptide, and variants thereof.

In particular embodiments, the salvage CAR further comprises the multimerization domain is selected from the group consisting of: an FKBP polypeptide, an FRB polypeptide, and variants thereof.

In additional embodiments, the multimerization domain is selected from the group consisting of: an FKBP12 polypeptide and an FRB T2098L polypeptide.

In some embodiments, the transmembrane domain is isolated from a polypeptide selected from the group consisting of: alpha or beta chain of the T-cell receptor, CDδ, CD3ε, CDγ, CD3ζ, CD4, CD5, CD8α, CD9, CD 16, CD22, CD27, CD28, CD33, CD37, CD45, CD64, CD71, CD80, CD86, CD 134, CD137, CD152, CD154, AMN, and PD1.

In particular embodiments, the salvage CAR further comprises the transmembrane domain is isolated from a polypeptide selected from the group consisting of: CD8α; CD4, CD45, PD1, and CD152.

In certain embodiments, the transmembrane domain is isolated from CD8α.

In certain embodiments, the one or more co-stimulatory signaling domains and/or primary signaling domains comprise an immunoreceptor tyrosine activation motif (ITAM).

In particular embodiments, the salvage CAR further comprises the one or more co-stimulatory signaling domains are isolated from a co-stimulatory molecule selected from the group consisting of: TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD278 (ICOS), DAP10, LAT, NKD2C, SLP76, TRIM, and ZAP70.

In some embodiments, the one or more co-stimulatory signaling domains are isolated from a co-stimulatory molecule selected from the group consisting of: CD28, CD134, CD137, and CD278.

In additional embodiments, the one or more co-stimulatory signaling domains is isolated from CD137.

In additional embodiments, the primary signaling domain isolated from a polypeptide selected from the group consisting of: FcRγ, FcRβ, CD3γ, CD3δ, CD3ε, CD3ζ, CD22, CD79a, CD79b, and CD66d.

In particular embodiments, the primary signaling domain isolated from a CD3ζ.

In some embodiments, the salvage CAR further comprises a hinge region polypeptide.

In particular embodiments, the hinge region polypeptide comprises a hinge region of CD8α.

In some embodiments, the salvage CAR further comprises a spacer region.

In particular embodiments, the salvage CAR further comprises a signal peptide.

In further embodiments, the signal peptide comprises an IgG1 heavy chain signal polypeptide, a CD8α signal polypeptide, or a human GM-CSF receptor alpha signal polypeptide.

In various embodiments, a salvage CAR comprising a signal peptide, an anti-BCMA scFv, a linker, an FRB (T82L) multimerization domain, a CD8α hinge and transmembrane domain, a 4-1BB co-stimulatory domain, and a CD3ζ primary signaling domain is provided.

In various embodiments, a salvage CAR comprising an amino acid sequence set forth in SEQ ID NO: 2 is provided.

In various embodiments, a dimerizable salvage receptor is provided comprising: an antigen binding domain; and a multimerization domain.

In various other embodiments, a dimerizable salvage receptor is provided comprising: a) an antigen binding domain; a multimerization domain; and an anchor domain.

In various particular embodiments, a dimerizable salvage receptor is provided consisting essentially of an antigen binding domain; a linker; and a multimerization domain.

In various certain embodiments, a dimerizable salvage receptor is provided consisting essentially of a signal peptide; an antigen binding domain; a linker; and a multimerization domain.

In various additional embodiments, a dimerizable salvage receptor is provided consisting essentially of an antigen binding domain; a linker; a multimerization domain; a hinge domain; and an anchor domain.

In various further embodiments, a dimerizable salvage receptor is provided consisting essentially of a signal peptide; an antigen binding domain; a linker; a multimerization domain; a hinge domain; and an anchor domain.

In additional embodiments, the antigen binding domain comprises an antibody or antigen binding fragment thereof.

In particular embodiments, the antibody or antigen binding fragment is selected from the group consisting of a Camel Ig, Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), and single-domain antibody (sdAb, Nanobody).

In some embodiments, the antibody or antigen binding fragment is an scFv.

In additional embodiments, the antigen binding domain binds an antigen selected from the group consisting of alpha folate receptor, 5T4, αvβ6 integrin, BCMA, B7-H3, B7-H6, CAIX, CD16, CD19, CD20, CD22, CD30, CD33, CD37, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, VEGFR2, and WT-1.

In certain embodiments, the antigen binding domain binds an antigen selected from the group consisting of BCMA, CD19, CSPG4, PSCA, ROR1, and TAG72.

In particular embodiments, the antigen binding domain binds an antigen selected from the group consisting of BCMA, CD19, CD20, CD22, CD23, CD33, CD37, CD52, CD80, and HLA-DR.

In some embodiments, the antigen binding domain binds BCMA or CD19.

In some embodiments, the antigen binding domain binds an antigen expressed on a cancer cell.

In further embodiments, the antigen binding domain binds an antigen expressed on a solid cancer cell.

In particular embodiments, the antigen binding domain binds an antigen expressed on a liquid cancer cell.

In certain embodiments, the antigen binding domain binds an antigen expressed on a malignant B cell.

In particular embodiments, the antigen binding domain binds an antigen expressed on a malignant plasma cell.

In particular embodiments, the multimization domain is selected from the group consisting of an FKBP polypeptide, an FRB polypeptide, a calcineurin polypeptide, a cyclophilin polypeptide, a bacterial DHFR polypeptide, a PYL1 polypeptide, an ABI1 polypeptide, a GIB1 polypeptide, a GAI polypeptide, and variants thereof.

In some embodiments, the multimerization domain is selected from the group consisting of an FKBP polypeptide, an FRB polypeptide, and variants thereof.

In further embodiments, the multimerization domain is selected from the group consisting of an FKBP12 polypeptide and an FRB T2098L polypeptide.

In additional embodiments, the hinge domain is selected from the group consisting essentially of a CD4 hinge, a CD8α hinge, a PD-1 hinge, and a CD152 hinge.

In particular embodiments, the anchor domain is selected from the group consisting of a GPI molecule and a transmembrane domain.

In additional embodiments, the anchor domain is comprises a transmembrane region of a polypeptide selected from the group consisting of: the alpha or beta chain of the T-cell receptor, CDδ, CD3E, CDγ, CD3ζ, CD4, CD5, CD8α, CD9, CD 16, CD22, CD27, CD28, CD33, CD37, CD45, CD64, CD71, CD80, CD86, CD 134, CD137, CD152, CD154, AMN, and PD1.

In various embodiments, a dimerizable salvage receptor comprising a signal peptide, an anti-CD19 scFv, a linker, and an FKBP12 multimerization domain is provided.

In various embodiments, a dimerizable salvage receptor comprising a signal peptide, an anti-CD19 scFv, a linker, and an FKBP12 multimerization domain bound to a bridging factor is provided.

In various embodiments, a dimerizable salvage receptor comprising polypeptide sequence set forth in any one of SEQ ID NOs: 3-5 is provided.

In various embodiments, a dimerizable salvage receptor comprising polypeptide sequence set forth in any one of SEQ ID NOs: 3-5 bound to a bridging factor is provided.

In various embodiments, a polynucleotide encoding a salvage CAR contemplated herein is provided.

In particular embodiments, a polynucleotide encoding a dimerizable salvage receptor contemplated herein is provided.

In various embodiments, a vector encoding a polynucleotide contemplated herein is provided.

In certain embodiments, the vector is an expression vector.

In particular embodiments, the vector is an episomal vector.

In particular embodiments, the vector is a viral vector.

In some embodiments, the vector is a retroviral vector.

In further embodiments, the vector is a lentiviral vector.

In particular embodiments, the lentiviral vector is selected from the group consisting essentially of human immunodeficiency virus 1 (HIV-1); human immunodeficiency virus 2 (HIV-2), visna-maedi virus (VMV) virus; caprine arthritis-encephalitis virus (CAEV); equine infectious anemia virus (EIAV); feline immunodeficiency virus (FIV); bovine immune deficiency virus (BIV); and simian immunodeficiency virus (SIV).

In certain embodiments, a vector comprises a left (5') retroviral LTR, a Psi (Ψ) packaging signal, a central polypurine tract/DNA flap (cPPT/FLAP), a retroviral export element; a promoter operably linked to the polynucleotide contemplated herein; and a right (3') retroviral LTR.

In additional embodiments, the promoter of the 5' LTR is replaced with a heterologous promoter.

In particular embodiments, the heterologous promoter is a cytomegalovirus (CMV) promoter, a Rous Sarcoma Virus (RSV) promoter, or an Simian Virus 40 (SV40) promoter.

In additional embodiments, the 3' LTR is a self-inactivating (SIN) LTR.

In various embodiments, a cell comprising a salvage CAR, a dimerizable salvage receptor, a polynucleotide, and/or a vector contemplated herein is provided.

In various embodiments, a cell comprising a salvage CAR and a dimerizable salvage receptor contemplated herein is provided.

In various embodiments, a cell comprising one or more polynucleotides contemplated herein is provided.

In various embodiments, a cell comprising one or more vectors contemplated herein is provided.

In some embodiments, the cell is a hematopoietic cell.

In further embodiments, the cell is an immune effector cell.

In particular embodiments, the cell is CD3+, CD4+, CD8+, or a combination thereof.

In certain embodiments, the cell is a T cell.

In additional embodiments, the cell is a cytotoxic T lymphocyte (CTL), a tumor infiltrating lymphocyte (TIL), or a helper T cell.

In some embodiments, the source of the cell is peripheral blood mononuclear cells, bone marrow, lymph nodes tissue, cord blood, thymus issue, tissue from a site of infection, ascites, pleural effusion, spleen tissue, or tumors.

In various embodiments, a composition comprising a salvage CAR, a dimerizable salvage receptor, a polynucleotide, a vector, and/or a cell contemplated herein is provided.

In various embodiments, a composition comprising a physiologically acceptable excipient and a salvage CAR, a dimerizable salvage receptor, a polynucleotide, a vector, and/or a cell contemplated herein is provided.

In various embodiments, a salvage CAR system is provided comprising: a CAR T cell comprising a salvage CAR that binds a first antigen; a dimerizable salvage receptor that binds a second antigen; and a bridging factor. In various embodiments, a salvage CAR system is provided comprising: a CAR T cell comprising a salvage CAR that binds a first antigen; and a dimerizable salvage receptor bound to a bridging factor.

In various embodiments, a salvage CAR system is provided comprising: a CAR T cell comprising a salvage CAR that binds a first antigen and a dimerizable salvage receptor that binds a second antigen; and a bridging factor.

In further embodiments, the dimerizable salvage receptor is encoded by a polynucleotide operably linked to an inducible promoter.

In particular embodiments, the first antigen is different that the second antigen.

In certain embodiments, the first antigen and second antigen are selected from the group consisting of: BCMA, CD19, CD20, CD22, CD23, CD33, CD37, CD52, CD80, and HLA-DR.

In particular embodiments, the first antigen and second antigen are selected from the group consisting of: BCMA or CD19.

In additional embodiments, the first antigen is BCMA and second antigen is CD19.

In some embodiments, the first antigen is CD19 and second antigen is BCMA.

In certain embodiments, the salvage CAR multimerization domain and dimerizable salvage receptor multimerization domain are a pair selected from FKBP and FRB, FKBP and calcineurin, FKBP and cyclophilin, FKBP and bacterial DHFR, calcineurin and cyclophilin, PYL1 and ABI1, or GIB1 and GAI, or variants thereof.

In particular embodiments, the salvage CAR multimerization domain comprises an FKBP polypeptide or variant thereof, and the dimerizable salvage receptor multimerization domain comprises an FRB polypeptide or variant thereof.

In some embodiments, the salvage CAR multimerization domain comprises an FRB polypeptide or variant thereof, and the dimerizable salvage receptor multimerization domain comprises an FKBP polypeptide or variant thereof.

In further embodiments, the bridging factor is AP21967, sirolimus, everolimus, novolimus, pimecrolimus, ridaforolimus, tacrolimus, temsirolimus, umirolimus, or zotarolimus.

In particular embodiments, the salvage CAR comprises an scFv specific for BCMA, an FRB T2098L multimerization domain, a transmembrane domain, a costimulatory domain of 4-1BB, and a primary signaling domain of CD3ζ; the dimerizable salvage receptor comprises an scFv specific for CD19, an FKBP12 multimerization domain, and optionally an anchor domain; and the bridging factor is AP21967.

In additional embodiments, the salvage CAR comprises an scFv specific for BCMA, an FKBP12 multimerization domain, a transmembrane domain, a costimulatory domain of 4-1BB, and a primary signaling domain of CD3ζ; the dimerizable salvage receptor comprises an scFv specific for CD19, an FRB T2098L multimerization domain, and optionally an anchor domain; and the bridging factor is AP21967.

In some embodiments, the salvage CAR comprises an scFv specific for CD19, an FRB T2098L multimerization domain, a transmembrane domain, a costimulatory domain of 4-1BB, and a primary signaling domain of CD3ζ; the dimerizable salvage receptor comprises an scFv specific for BCMA, an FKBP12 multimerization domain, and optionally an anchor domain; and the bridging factor is AP21967.

In particular embodiments, the salvage CAR comprises an scFv specific for CD19, an FKBP12 multimerization domain, a transmembrane domain, a costimulatory domain of 4-1BB, and a primary signaling domain of CD3ζ; the dimerizable salvage receptor comprises an scFv specific for BCMA, an FRB T2098L multimerization domain, and optionally an anchor domain; and the bridging factor is AP21967.

In certain embodiments, the salvage CAR comprises an scFv specific for BCMA, an FRB multimerization domain, a transmembrane domain, a costimulatory domain of 4-1BB, and a primary signaling domain of CD3ζ; the dimerizable salvage receptor comprises an scFv specific for CD19, an FKBP12 multimerization domain, and optionally an anchor domain; and the bridging factor is Rapamycin, temsirolimus or everolimus.

In some embodiments, the salvage CAR comprises an scFv specific for BCMA, an FKBP12 multimerization domain, a transmembrane domain, a costimulatory domain of 4-1BB, and a primary signaling domain of CD3ζ; the dimerizable salvage receptor comprises an scFv specific for CD19, an FRB multimerization domain, and optionally an anchor domain; and the bridging factor is Rapamycin, temsirolimus or everolimus.

In certain embodiments, the salvage CAR comprises an scFv specific for CD19, an FRB multimerization domain, a transmembrane domain, a costimulatory domain of 4-1BB, and a primary signaling domain of CD3ζ; the dimerizable salvage receptor comprises an scFv specific for BCMA and an FKBP12 multimerization domain, and optionally an anchor domain; and the bridging factor is Rapamycin, temsirolimus or everolimus.

In further embodiments, the salvage CAR comprises an scFv specific for CD19, an FKBP12 multimerization domain, a transmembrane domain, a costimulatory domain of 4-1BB, and a primary signaling domain of CD3ζ; the dimerizable salvage receptor comprises an scFv specific for BCMA and an FRB multimerization domain, and optionally an anchor domain; and the bridging factor is Rapamycin, temsirolimus or everolimus.

In various embodiments, a method for decreasing the number of relapsed/refractory cancer cells in a subject is provided, comprising administering to the subject: an effective amount of a dimerizable salvage receptor, wherein the subject has previously been administered immune effector cells comprising a salvage CAR; and an effective amount of a bridging factor that binds the multimerization domains of the dimerizable salvage receptor and the salvage CAR.

In various embodiments, a method for decreasing the number of relapsed/refractory cancer cells in a subject is provided, comprising administering to the subject: an effective amount of a dimerizable salvage receptor bound to a bridging factor, wherein the subject has previously been administered immune effector cells comprising a salvage CAR.

In various embodiments, a method for decreasing the number of relapsed/refractory cancer cells in a subject is provided, comprising administering to the subject: an effective amount of a salvage CAR T cell comprising a dimerizable salvage receptor; an inducer agent to induce expression of the dimerizable salvage receptor; and an effective amount of a bridging factor that binds the multimerization domains of the dimerizable salvage receptor and the salvage CAR.

In various embodiments, a method of treating a cancer in a subject in need thereof is provided, comprising administering to the subject: an effective amount of a dimerizable salvage receptor, wherein the subject has previously been administered immune effector cells comprising a salvage CAR; and an effective amount of a bridging factor that binds the multimerization domains of the dimerizable salvage receptor and the salvage CAR.

In various embodiments, a method of treating a cancer in a subject in need thereof is provided, comprising administering to the subject: an effective amount of a dimerizable salvage receptor bound to a bridging factor, wherein the subject has previously been administered immune effector cells comprising a salvage CAR.

In various embodiments, a method of treating a cancer in a subject in need thereof, is provided, comprising administering to the subject: an effective amount of a salvage CAR T cell comprising a dimerizable salvage receptor; an inducer agent to induce expression of the dimerizable salvage receptor; and an effective amount of a bridging factor that binds the multimerization domains of the dimerizable salvage receptor and the salvage CAR.

In additional embodiments, the cancer is a solid cancer.

In particular embodiments, the cancer is selected from the group consisting of: adrenal cancer, adrenocortical carcinoma, anal cancer, appendix cancer, astrocytoma, atypical teratoid/rhabdoid tumor, basal cell carcinoma, bile duct cancer, bladder cancer, bone cancer, brain/CNS cancer, breast cancer, bronchial tumors, cardiac tumors, cervical cancer, cholangiocarcinoma, chondrosarcoma, chordoma, colon cancer, colorectal cancer, craniopharyngioma, ductal carcinoma in situ (DCIS) endometrial cancer, ependymoma, esophageal cancer, esthesioneuroblastoma, Ewing's sarcoma, extracranial germ cell tumor, extragonadal germ cell tumor, eye cancer, fallopian tube cancer, fibrous histiosarcoma, fibrosarcoma, gallbladder cancer, gastric cancer, gastrointestinal carcinoid tumors, gastrointestinal stromal tumor (GIST), germ cell tumors, glioma, glioblastoma, head and neck cancer, hemangioblastoma, hepatocellular cancer, hypopharyngeal cancer, intraocular melanoma, kaposi sarcoma, kidney cancer, laryngeal cancer, leiomyosarcoma, lip cancer, liposarcoma, liver cancer, lung cancer, non-small cell lung cancer, lung carcinoid tumor, malignant mesothelioma, medullary carcinoma, medulloblastoma, menangioma, melanoma, Merkel cell carcinoma, midline tract carcinoma, mouth cancer, myxosarcoma, myelodysplastic syndrome, myeloproliferative neoplasms, nasal cavity and paranasal sinus cancer, nasopharyngeal cancer, neuroblastoma, oligodendroglioma, oral cancer, oral cavity cancer, oropharyngeal cancer, osteosarcoma, ovarian cancer, pancreatic cancer, pancreatic islet cell tumors, papillary carcinoma, paraganglioma, parathyroid cancer, penile cancer, pharyngeal cancer, pheochromocytoma, pinealoma, pituitary tumor, pleuropulmonary blastoma, primary peritoneal cancer, prostate cancer, rectal cancer, retinoblastoma, renal cell carcinoma, renal pelvis and ureter cancer, rhabdomyosarcoma, salivary gland cancer, sebaceous gland carcinoma, skin cancer, soft tissue sarcoma, squamous cell carcinoma, small cell lung cancer, small intestine cancer, stomach cancer, sweat gland carcinoma, synovioma, testicular cancer, throat cancer, thymus cancer, thyroid cancer, urethral cancer, uterine cancer, uterine sarcoma, vaginal cancer, vascular cancer, vulvar cancer, and Wilms Tumor.

In further embodiments, the cancer is selected from the group consisting of liver cancer, pancreatic cancer, lung cancer, breast cancer, bladder cancer, brain cancer, bone cancer, thyroid cancer, kidney cancer, and skin cancer.

In additional embodiments, the cancer is a liquid cancer or hematological cancer.

In particular embodiments, the hematological malignancy is a B cell malignancy.

In some embodiments, the B cell malignancy is selected from the group consisting of leukemias, lymphomas, and multiple myelomas.

In certain embodiments, the B cell malignancy is selected from the group consisting of acute lymphocytic leukemia (ALL), acute myeloid leukemia (AML), myeloblastic, promyelocytic, myelomonocytic, monocytic, erythroleukemia, hairy cell leukemia (HCL), chronic lymphocytic leukemia (CLL), and chronic myeloid leukemia (CML), chronic myelomonocytic leukemia (CMML) and polycythemia vera, Hodgkin lymphoma, nodular lymphocyte-predominant Hodgkin lymphoma, Burkitt lymphoma, small lymphocytic lymphoma (SLL), diffuse large B-cell lymphoma, follicular lymphoma, immunoblastic large cell lymphoma, precursor B-lymphoblastic lymphoma, mantle cell lymphoma, marginal zone lymphoma, mycosis fungoides, anaplastic large cell lymphoma, Sezary syndrome, precursor T-lymphoblastic lymphoma, multiple myeloma, overt multiple myeloma, smoldering multiple myeloma, plasma cell leukemia, non-secretory myeloma, IgD myeloma, osteosclerotic myeloma, solitary plasmacytoma of bone, and extramedullary plasmacytoma.

In particular embodiments, the B cell malignancy is multiple myeloma.

In various embodiments, a method for ameliorating at one or more symptoms associated with a cancer in a subject is provided, comprising administering to the subject: an effective amount of a dimerizable salvage receptor, wherein the subject has previously been administered immune effector cells comprising a salvage CAR; and an effective amount of a bridging factor that binds the multimerization domains of the dimerizable salvage receptor and the salvage CAR.

In various embodiments, a method for ameliorating at one or more symptoms associated with a cancer in a subject is provided, comprising administering to the subject: an effective amount of a dimerizable salvage receptor bound to a bridging factor, wherein the subject has previously been administered immune effector cells comprising a salvage CAR.

In various embodiments, a method for ameliorating at one or more symptoms associated with a cancer in a subject is provided, comprising administering to the subject: an effective amount of a salvage CAR T cell comprising a dimerizable salvage receptor; an inducer agent to induce expression of the dimerizable salvage receptor; and an effective amount of a bridging factor that binds the multimerization domains of the dimerizable salvage receptor and the salvage CAR.

In particular embodiments, the one or more symptoms ameliorated are selected from the group consisting of: weakness, fatigue, shortness of breath, easy bruising and bleeding, frequent infections, enlarged lymph nodes, distended or painful abdomen, bone or joint pain, fractures, unplanned weight loss, poor appetite, night sweats, persistent mild fever, and decreased urination.

BRIEF DESCRIPTION OF THE SEQUENCE IDENTIFIERS

Figure 1:
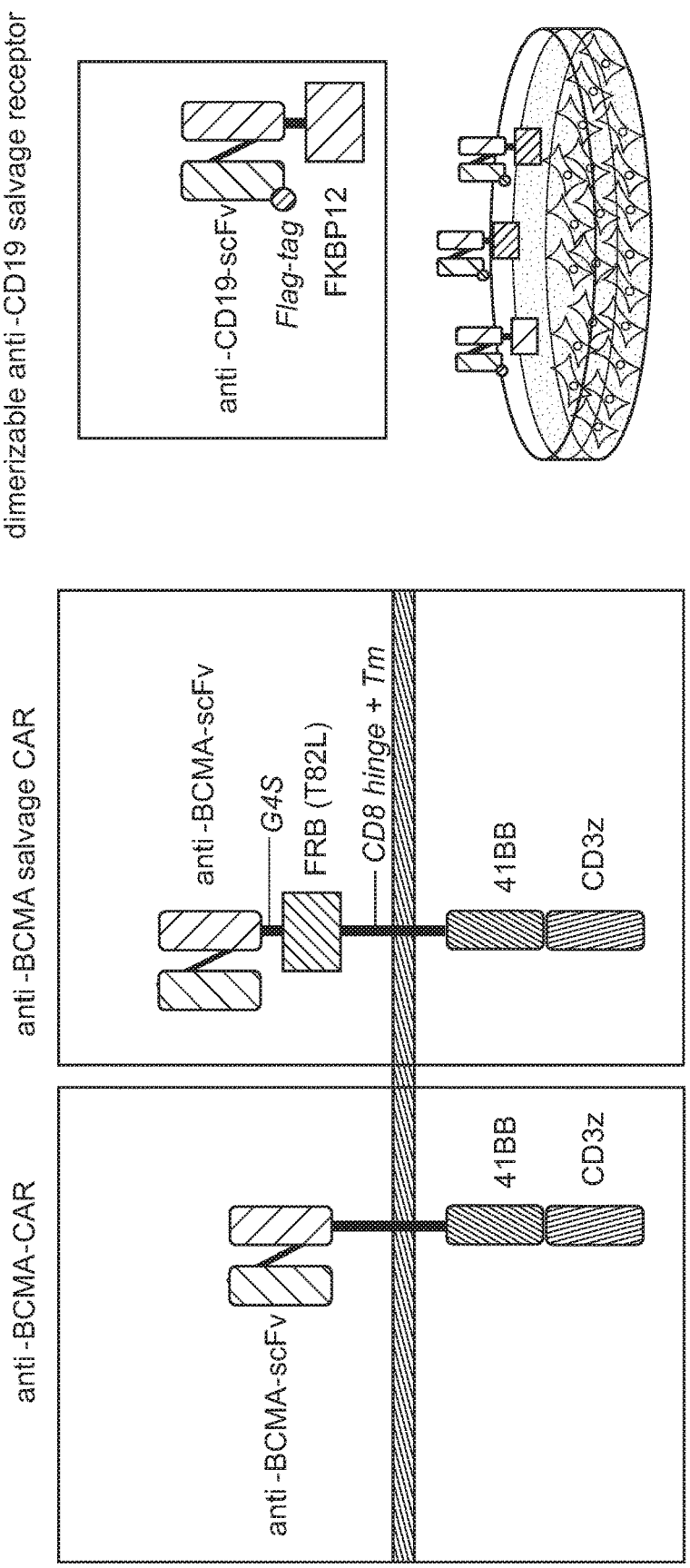
FIG. 1 shows a cartoon of a CAR T cell (left panel) compared to a salvage CAR system. The salvage CAR system comprises a salvage CAR (center panel) and a dimerizable salvage receptor (upper right panel). The lower right panel shows a 293T cell line engineered to express secreted dimerizable salvage receptor.

SEQ ID NO: 1 sets forth the polypeptide sequence for an anti-BCMA CAR.

SEQ ID NO: 2 sets forth the polypeptide sequence for an anti-BCMA salvage CAR.

SEQ ID NO: 3 sets forth the polypeptide sequence for a dimerizing salvage receptor.

SEQ ID NO: 4 sets forth the polypeptide sequence for a dimerizing salvage receptor-T2A-fluorescent reporter.

SEQ ID NO: 5 sets forth the polypeptide sequence for a dimerizing salvage receptor-T2A-fluorescent reporter.

SEQ ID NO: 6 sets forth the polypeptide sequence for an anti-BCMA DARIC.

SEQ ID NOs: 7-17 set forth the amino acid sequences of various linkers.

SEQ ID NOs: 18-42 set forth the amino acid sequences of protease cleavage sites and self-cleaving polypeptide cleavage sites.

DETAILED DESCRIPTION

A. Overview

Cancers are often heterogeneous pools of cells expressing different levels of various antigens. Generally, immunotherapies are initially selected to target an antigen that is expressed on a majority of cancer cells and that substantially lacks expression on normal cells. An effective targeted immunotherapy will kill the majority of cancer cells that express the target antigen, resulting in partial or complete remission. However, because most cancers are heterogeneous in nature, the remaining cancer cells that do not express, or that express low levels, of the targeted antigen are spared and can potentially give rise to cancer cells that are not effectively targeted by the initial immunotherapy.

One major obstacle that still limits the efficacy of CAR T cell therapy is relapse of "antigen negative" cancers. For example, although anti-CD19 CART cell therapy initially results in impressive remission rates in relapsed and refractory acute ALL, relapse of CD19 negative leukemic blasts occurs in approximately 10-20% of cases. The alarmingly high rate of antigen negative relapse represents an, as of yet, unaddressed weakness of CAR T immunotherapy. Without wishing to be bound by any particular theory, the inventors have solved the problem by re-engineering CARs so that they may retarget a virtually unlimited number of additional antigens expressed on the relapsed or refractory antigen negative cancer cells. Thus, the compositions and methods contemplated herein represent an important advance in CAR T cell immunotherapy.

In various embodiments, a salvage chimeric antigen receptor (CAR) is provided. The salvage CAR may comprise one or more antigen binding domains, a multimerization domain, a transmembrane domain, and one or more intracellular signaling domains. In some embodiments, a CAR can be adapted to a salvage CAR by incorporating a multimerization domain into the CAR. The multimerization domain can be positioned intracellularly or extracellularly.

In various embodiments, a dimerizable salvage receptor is provided. The dimerizable salvage CAR receptor may comprise one or more antigen binding domains and a multimerization domain, and optionally one or more of a linker domain, hinge domain, and/or anchor domain.

In various other embodiments a salvage CAR system is provided. The salvage CAR system may comprise salvage CAR T cells, a dimerizable salvage receptor, and a bridging factor. The bridging factor binds the multimerization domains of the salvage CAR and the dimerizable salvage receptor, which leads to formation of a functional CAR signaling complex.

In some embodiments, salvage CAR T cells further comprise an inducible dimerizable salvage receptor In particular embodiments, a method for purifying dimerizable salvage receptors preloaded with bridging factor is provided.

The practice of the particular embodiments will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See, e.g., Sambrook, et al., *Molecular Cloning: A Laboratory Manual* (3rd Edition, 2001); Sambrook, et al., *Molecular Cloning: A Laboratory Manual* (2nd Edition, 1989); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford, 1985); Anand, *Techniques for the Analysis of Complex Genomes*, (Academic Press, New York, 1992); *Transcription and Translation* (B. Hames & S. Higgins, Eds., 1984); Perbal, *A Practical Guide to Molecular Cloning* (1984); Harlow and Lane, *Antibodies*, (Cold Spring Harbor Laboratory Press, Cold Spring Harbor, N.Y., 1998) *Current Protocols in Immunology* Q. E. Coligan, A. M. Kruisbeek, D. H. Margulies, E. M. Shevach and W.

Strober, eds., 1991); *Annual Review of Immunology*; as well as monographs in journals such as *Advances in Immunology*.

B. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of particular embodiments, preferred embodiments of compositions, methods and materials are described herein. For the purposes of the present disclosure, the following terms are defined below.

The articles "a," "an," and "the" are used herein to refer to one or to more than one (i.e., to at least one, or to one or more) of the grammatical object of the article. By way of example, "an element" means one element or one or more elements.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, 9%, ±8%, ±7%, ±6%, ±5%, ±4%, ±3%, ±2%, or ±1% about a reference quantity, level, value, number, frequency, percentage, dimension, size, amount, weight or length.

Throughout this specification, unless the context requires otherwise, the words "comprise," "comprises," and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are present that materially affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment. Thus, the appearances of the foregoing phrases in various places throughout this specification are not necessarily all referring to the same embodiment. Furthermore, the particular features, structures, or characteristics may be combined in any suitable manner in one or more embodiments. It is also understood that the positive recitation of a feature in one embodiment, serves as a basis for excluding the feature in a particular embodiment.

An "antigen (Ag)" refers to a compound, composition, or substance that can stimulate the production of antibodies or a T cell response in an animal, including compositions (such as one that includes a cancer-specific protein) that are injected or absorbed into an animal. Exemplary antigens include but are not limited to lipids, carbohydrates, polysaccharides, glycoproteins, peptides, or nucleic acids. An antigen reacts with the products of specific humoral or cellular immunity, including those induced by heterologous antigens, such as the disclosed antigens.

A "target antigen" or "target antigen of interest" is an antigen that a binding domain contemplated herein, is designed to bind. In particular embodiments, the target antigen is selected from the group consisting of: alpha folate receptor, 5T4, αvβ6 integrin, BCMA, B7-H3, B7-H6, CAIX, CD16, CD19, CD20, CD22, CD30, CD33, CD37, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, STn, TAG72, TEMs, VEGFR2, and WT-1.

In one embodiment, the antigen is an MHC-peptide complex, such as a class I MHC-peptide complex or a class II MHC-peptide complex.

As used herein, the terms, "binding domain," "extracellular domain," "antigen binding domain," "extracellular binding domain," "extracellular antigen binding domain," "antigen-specific binding domain," and "extracellular antigen specific binding domain," are used interchangeably and provide a polypeptide with the ability to specifically bind to the target antigen of interest. The binding domain may be derived either from a natural, synthetic, semi-synthetic, or recombinant source.

The terms "specific binding affinity" or "specifically binds" or "specifically bound" or "specific binding" or "specifically targets" as used herein, describe binding of an antibody or antigen binding fragment thereof to a target antigen at greater binding affinity than background binding. A binding domain "specifically binds" to a target antigen, if it binds to or associates with the antigen with an affinity or $K_a$ (i.e., an equilibrium association constant of a particular binding interaction with units of 1/M) of, for example, greater than or equal to about $10^5$ M$^{-1}$. In certain embodiments, a binding domain (or a fusion protein thereof) binds to a target with a $K_a$ greater than or equal to about $10^6$ M$^{-1}$, $10^7$ M$^{-1}$, $10^8$ M$^{-1}$, $10^9$ M$^{-1}$, $10^{10}$ M$^{-1}$, $10^{11}$ M$^{-1}$, $10^{12}$ M$^{-1}$, or $10^{13}$ M$^{-1}$. "High affinity" binding domains (or single chain fusion proteins thereof) refers to those binding domains with a $K_a$ of at least $10^7$ M$^{-1}$, at least $10^8$ M$^{-1}$, at least $10^9$ M$^{-1}$, at least $10^{10}$ M$^{-1}$, at least $10^{11}$ M$^{-1}$, at least $10^{12}$ M$^{-1}$, at least $10^{13}$ M$^{-1}$, or greater.

Alternatively, affinity may be defined as an equilibrium dissociation constant ($K_d$) of a particular binding interaction with units of M (e.g., $10^{-5}$ M to $10^{-13}$ M, or less). Affinities of binding domain polypeptides can be readily determined using conventional techniques, e.g., by competitive ELISA (enzyme-linked immunosorbent assay), or by binding association, or displacement assays using labeled ligands, or using a surface-plasmon resonance device such as the Biacore T100, which is available from Biacore, Inc., Piscataway, NJ, or optical biosensor technology such as the EPIC system or EnSpire that are available from Corning and Perkin Elmer respectively (see also, e.g., Scatchard et al. (1949) *Ann. N. Y. Acad. Sci.* 51:660; and U.S. Pat. Nos. 5,283,173; 5,468,614, or the equivalent).

In one embodiment, the affinity of specific binding is about 2 times greater than background binding, about 5 times greater than background binding, about 10 times greater than background binding, about 20 times greater than background binding, about 50 times greater than background binding, about 100 times greater than background binding, or about 1000 times greater than background binding or more.

An "antibody" refers to a binding agent that is a polypeptide comprising at least a light chain or heavy chain immunoglobulin variable region which specifically recognizes and binds an epitope of an antigen, such as a lipid, carbohydrate, polysaccharide, glycoprotein, peptide, or nucleic acid containing an antigenic determinant, such as those recognized by an immune cell.

An "epitope" or "antigenic determinant" refers to the region of an antigen to which a binding agent binds.

Antibodies include antigen binding fragments thereof, such as Camel Ig, Ig NAR, Fab fragments, Fab' fragments, F(ab)'2 fragments, F(ab)'3 fragments, Fv, single chain Fv proteins ("scFv"), bis-scFv, (scFv)2, minibodies, diabodies, triabodies, tetrabodies, disulfide stabilized Fv proteins ("dsFv"), and single-domain antibody (sdAb, Nanobody) and portions of full length antibodies responsible for antigen binding. The term also includes genetically engineered forms such as chimeric antibodies (for example, humanized murine antibodies), heteroconjugate antibodies (such as, bispecific antibodies) and antigen binding fragments thereof. See also, Pierce Catalog and Handbook, 1994-1995 (Pierce Chemical Co., Rockford, IL); Kuby, J., Immunology, 3rd Ed., W. H. Freeman & Co., New York, 1997.

As would be understood by the skilled person and as described elsewhere herein, a complete antibody comprises two heavy chains and two light chains. Each heavy chain consists of a variable region and a first, second, and third constant region, while each light chain consists of a variable region and a constant region. Mammalian heavy chains are classified as α, δ, ε, γ, and μ. Mammalian light chains are classified as λ or κ. Immunoglobulins comprising the α, δ, ε, γ, and μ heavy chains are classified as immunoglobulin (Ig)A, IgD, IgE, IgG, and IgM. The complete antibody forms a "Y" shape. The stem of the Y consists of the second and third constant regions (and for IgE and IgM, the fourth constant region) of two heavy chains bound together and disulfide bonds (inter-chain) are formed in the hinge. Heavy chains γ, α and δ have a constant region composed of three tandem (in a line) Ig domains, and a hinge region for added flexibility; heavy chains μ and ε have a constant region composed of four immunoglobulin domains. The second and third constant regions are referred to as "CH2 domain" and "CH3 domain", respectively. Each arm of the Y includes the variable region and first constant region of a single heavy chain bound to the variable and constant regions of a single light chain. The variable regions of the light and heavy chains are responsible for antigen binding.

Light and heavy chain variable regions contain a "framework" region interrupted by three hypervariable regions, also called "complementarity-determining regions" or "CDRs." The CDRs can be defined or identified by conventional methods, such as by sequence according to Kabat et al. (Wu, T T and Kabat, E. A., *J Exp Med.* 132(2):211-50, (1970); Borden, P. and Kabat E. A., *PNAS,* 84: 2440-2443 (1987); (see, Kabat et al., *Sequences of Proteins of Immunological Interest,* U.S. Department of Health and Human Services, 1991, which is hereby incorporated by reference), or by structure according to Chothia et al (Chothia, C. and Lesk, A. M., *J Mol. Biol.,* 196(4): 901-917 (1987), Chothia, C. et al, *Nature,* 342: 877-883 (1989)).

Illustrative examples of rules for predicting light chain CDRs include: CDR-L1 starts at about residue 24, is preceded by a Cys, is about 10-17 residues, and is followed by a Trp (typically Trp-Tyr-Gln, but also, Trp-Leu-Gln, Trp-Phe-Gln, Trp-Tyr-Leu); CDR-L2 starts about 16 residues after the end of CDR-L1, is generally preceded by Ile-Tyr, but also, Val-Tyr, Ile-Lys, Ile-Phe, and is 7 residues; and CDR-L3 starts about 33 residues after the end of CDR-L2, is preceded by a Cys, is 7-11 residues, and is followed by Phe-Gly-XXX-Gly (SEQ ID NO:44) (XXX is any amino acid).

Illustrative examples of rules for predicting heavy chain CDRs include: CDR-H1 starts at about residue 26, is preceded by Cys-XXX-XXX-XXX (SEQ ID NO:45), is 10-12 residues and is followed by a Trp (typically Trp-Val, but also, Trp-Ile, Trp-Ala); CDR-H2 starts about 15 residues after the end of CDR-H1, is generally preceded by Leu-Glu-Trp-Ile-Gly (SEQ ID NO:46), or a number of variations, is 16-19 residues, and is followed by Lys/Arg-Leu/Ile/Val/Phe/Thr/Ala-Thr/Ser/Ile/Ala; and CDR-H3 starts about 33 residues after the end of CDR-H2, is preceded by Cys-XXX-XXX (SEQ ID NO:45) (typically Cys-Ala-Arg), is 3 to 25 residues, and is followed by Trp-Gly-XXX-Gly (SEQ ID NO:47).

In one embodiment, light chain CDRs and the heavy chain CDRs are determined according to the Kabat method In one embodiment, light chain CDRs and the heavy chain CDR2 and CDR3 are determined according to the Kabat method, and heavy chain CDR1 is determined according to the AbM method, which is a comprise between the Kabat and Clothia methods, see e.g., Whitelegg N & Rees A R, *Protein Eng.* 2000 December; 13(12):819-24 and *Methods Mol Biol.* 2004; 248:51-91. Programs for predicting CDRs are publicly available, e.g., AbYsis (www.bioinf.org.uk/abysis/).

The sequences of the framework regions of different light or heavy chains are relatively conserved within a species, such as humans. The framework region of an antibody, that is the combined framework regions of the constituent light and heavy chains, serves to position and align the CDRs in three-dimensional space. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, the CDRs located in the variable domain of the heavy chain of the antibody are referred to as CDRH1, CDRH2, and CDRH3, whereas the CDRs located in the variable domain of the light chain of the antibody are referred to as CDRL1, CDRL2, and CDRL3. Antibodies with different specificities (i.e., different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "V$_L$" or "VL" refer to the variable region of an immunoglobulin light chain, including that of an antibody, Fv, scFv, dsFv, Fab, or other antibody fragment as disclosed herein.

References to "V$_H$" or "VH" refer to the variable region of an immunoglobulin heavy chain, including that of an antibody, Fv, scFv, dsFv, Fab, or other antibody fragment as disclosed herein.

A "monoclonal antibody" is an antibody produced by a single clone of B lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a mouse. In particular preferred embodiments, an antigen-specific binding domain is a chimeric antibody or antigen binding fragment thereof.

In particular embodiments, the antibody is a human antibody (such as a human monoclonal antibody) or antigen binding fragment thereof that specifically binds to a target antigen. Human antibodies can be constructed by combining Fv clone variable domain sequence(s) selected from human-derived phage display libraries with known human constant domain sequences(s) as described above. Alternatively, human monoclonal antibodies may be made by the hybridoma method. Human myeloma and mouse-human heteromyeloma cell lines for the production of human monoclonal antibodies have been described, for example, by Kozbor *J Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991). In addition, transgenic animals (e.g., mice) can be used to produce a full repertoire of human antibodies in the absence of endogenous immunoglobulin production. See, e.g., Jakobovits et al., *PNAS USA*, 90: 2551 (1993); Jakobovits et al., *Nature*, 362: 255 (1993); Bruggermann et al., *Year in Immunol.*, 7: 33 (1993). Gene shuffling can also be used to derive human antibodies from non-human, e.g., rodent antibodies, where the human antibody has similar affinities and specificities to the starting non-human antibody. See PCT WO 93/06213 published Apr. 1, 1993. Unlike traditional humanization of non-human antibodies by CDR grafting, this technique provides completely human antibodies, which have no FR or CDR residues of non-human origin.

A "humanized" antibody is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. Humanized or other monoclonal antibodies can have additional conservative amino acid substitutions, which have substantially no effect on antigen binding or other immunoglobulin functions. Humanized antibodies can be constructed by means of genetic engineering (see for example, U.S. Pat. No. 5,585,089).

"Camel Ig" or "camelid VHH" as used herein refers to the smallest known antigen-binding unit of a heavy chain antibody (Koch-Nolte, et al, *FASEB J.*, 21: 3490-3498 (2007)). A "heavy chain antibody" or a "camelid antibody" refers to an antibody that contains two VH domains and no light chains (Riechmann L. et al, *J. Immunol. Methods* 231:25-38 (1999); WO94/04678; WO94/25591; U.S. Pat. No. 6,005,079).

"IgNAR" of "immunoglobulin new antigen receptor" refers to class of antibodies from the shark immune repertoire that consist of homodimers of one variable new antigen receptor (VNAR) domain and five constant new antigen receptor (CNAR) domains. IgNARs represent some of the smallest known immunoglobulin-based protein scaffolds and are highly stable and possess efficient binding characteristics. The inherent stability can be attributed to both (i) the underlying Ig scaffold, which presents a considerable number of charged and hydrophilic surface exposed residues compared to the conventional antibody VH and VL domains found in murine antibodies; and (ii) stabilizing structural features in the complementary determining region (CDR) loops including inter-loop disulfide bridges, and patterns of intra-loop hydrogen bonds.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three hypervariable regions (HVRs) of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., Nat. Med. 9:129-134 (2003); and Hollinger et al., PNAS USA 90: 6444-6448 (1993). Triabodies and tetrabodies are also described in Hudson et al., Nat. Med. 9:129-134 (2003).

"Single domain antibody" or "sdAb" or "nanobody" refers to an antibody fragment that consists of the variable region of an antibody heavy chain (VH domain) or the variable region of an antibody light chain (VL domain) (Holt, L., et al, Trends in Biotechnology, 21(11): 484-490).

"Single-chain Fv" or "scFv" antibody fragments comprise the VH and VL domains of antibody, wherein these domains are present in a single polypeptide chain and in either orientation (e.g., VL-VH or VH-VL). Generally, the scFv polypeptide further comprises a polypeptide linker between the VH and VL domains which enables the scFv to form the desired structure for antigen binding. For a review of scFv, see, e.g., Pluckthün, in *The Pharmacology of Monoclonal Antibodies*, vol. 113, Rosenburg and Moore eds., (Springer-Verlag, New York, 1994), pp. 269-315.

Single chain antibodies may be cloned from the V region genes of a hybridoma specific for a desired target. The production of such hybridomas has become routine. A technique which can be used for cloning the variable region heavy chain ($V_H$) and variable region light chain ($V_L$) has been described, for example, in Orlandi et al., PNAS, 1989; 86: 3833-3837.

A "linker" refers to a plurality of amino acid residues between the various polypeptide domains, e.g., between $V_H$ and $V_L$ domains, added for appropriate spacing and conformation of the molecule. In particular embodiments, the linker is a variable region linking sequence. A "variable region linking sequence," is an amino acid sequence that connects the $V_H$ and $V_L$ domains and provides a spacer function compatible with interaction of the two sub-binding domains so that the resulting polypeptide retains a specific binding affinity to the same target molecule as an antibody that comprises the same light and heavy chain variable regions. In particular embodiments, a linker separates one or more heavy or light chain variable domains, hinge domains, multimerization domains, transmembrane domains, co-stimulatory domains, and/or primary signaling domains.

Illustrated examples of linkers suitable for use in particular embodiments contemplated herein include, but are not limited to the following amino acid sequences: GGG; DGGGS (SEQ ID NO: 7); TGEKP (SEQ ID NO: 8) (see, e.g., Liu et al., PNAS 5525-5530 (1997)); GGRR (SEQ ID NO: 9) (Pomerantz et al. 1995, supra); (GGGGS)$_n$ wherein n=1, 2, 3, 4 or 5 (SEQ ID NO: 10) (Kim et al., PNAS 93, 1156-1160 (1996.); EGKSSGSGSESKVD (SEQ ID NO: 11) (Chaudhary et al., 1990, Proc. Natl. Acad. Sci. U.S.A. 87:1066-1070); KESGSVSSEQLAQFRSLD (SEQ ID NO: 12) (Bird et al., 1988, Science 242:423-426), GGRRGGGS (SEQ ID NO: 13); LRQRDGERP (SEQ ID NO: 14); LRQKDGGGSERP (SEQ ID NO: 15); LRQKD(GGGS)$_2$ERP (SEQ ID NO: 16). Alternatively, flexible linkers can be rationally designed using a computer program capable of modeling both DNA-binding sites and the peptides themselves (Desjarlais & Berg, PNAS 90:2256-2260 (1993), PNAS 91:11099-11103 (1994) or by phage display methods. In one embodiment, the linker comprises the following amino acid sequence: GSTSGSGKPGSGEGSTKG (SEQ ID NO: 17) (Cooper et al., *Blood*, 101(4): 1637-1644 (2003)).

A "spacer domain," refers to a polypeptide that separates two domains. In one embodiment, a spacer domain moves an antigen binding domain away from the effector cell surface to enable proper cell/cell contact, antigen binding and activation (Patel et al., *Gene Therapy*, 1999; 6: 412-419). In particular embodiments, a spacer domain separates one or more heavy or light chain variable domains, multimerization domains, transmembrane domains, co-stimulatory domains, and/or primary signaling domains. The spacer domain may be derived either from a natural, synthetic, semi-synthetic, or recombinant source. In certain embodiments, a spacer domain is a portion of an immunoglobulin, including, but not limited to, one or more heavy chain constant regions, e.g., CH2 and CH3. The spacer domain can include the amino acid sequence of a naturally occurring immunoglobulin hinge region or an altered immunoglobulin hinge region.

A "hinge domain," refers to a polypeptide that plays a role in positioning the antigen binding domain away from the effector cell surface to enable proper cell/cell contact, antigen binding and activation. In particular embodiments, polypeptides may comprise one or more hinge domains between the binding domain and the multimerization domain, between the binding domain and the transmembrane domain (TM), or between the multimerization domain and the transmembrane domain. The hinge domain may be derived either from a natural, synthetic, semi-synthetic, or recombinant source. The hinge domain can include the amino acid sequence of a naturally occurring immunoglobulin hinge region or an altered immunoglobulin hinge region.

An "altered hinge region" refers to (a) a naturally occurring hinge region with up to 30% amino acid changes (e.g., up to 25%, 20%, 15%, 10%, or 5% amino acid substitutions or deletions), (b) a portion of a naturally occurring hinge region that is at least 10 amino acids (e.g., at least 12, 13, 14 or 15 amino acids) in length with up to 30% amino acid changes (e.g., up to 25%, 20%, 15%, 10%, or 5% amino acid substitutions or deletions), or (c) a portion of a naturally occurring hinge region that comprises the core hinge region (which may be 4, 5, 6, 7, 8, 9, 10, 11, 12, 13, 14, or 15, or at least 4, 5, 6, 7, 8, 9, 10, 11, 12, 13, 14, or 15 amino acids in length). In certain embodiments, one or more cysteine residues in a naturally occurring immunoglobulin hinge region may be substituted by one or more other amino acid residues (e.g., one or more serine residues). An altered immunoglobulin hinge region may alternatively or additionally have a proline residue of a wild type immunoglobulin hinge region substituted by another amino acid residue (e.g., a serine residue).

A "multimerization domain," as used herein, refers to a polypeptide that preferentially interacts or associates with another different polypeptide directly or via a bridging molecule, wherein the interaction of different multimerization domains substantially contributes to or efficiently promotes multimerization (i.e., the formation of a dimer, trimer, or multipartite complex, which may be a homodimer, heterodimer, homotrimer, heterotrimer, homomultimer, heteromultimer). A multimerization domain may be derived either from a natural, synthetic, semi-synthetic, or recombinant source.

Illustrative examples of multimerization domains suitable for use in particular embodiments contemplated herein include an FKBP polypeptide, an FRB polypeptide, a calcineurin polypeptide, a cyclophilin polypeptide, a bacterial DHFR polypeptide, a PYL1 polypeptide, an ABI1 polypeptide, a GIB1 polypeptide, a GAI polypeptide, or variants thereof.

A "bridging factor" refers to a molecule that associates with and that is disposed between two or more multimerization domains. In particular embodiments, multimerization domains substantially contribute to or efficiently promote formation of a polypeptide complex only in the presence of a bridging factor. In particular embodiments, multimerization domains do not contribute to or do not efficiently promote formation of a polypeptide complex in the absence of a bridging factor. Illustrative examples of bridging factors suitable for use in particular embodiments contemplated herein include, but are not limited to rapamycin (sirolimus) or a rapalog thereof, coumermycin or a derivative thereof, gibberellin or a derivative thereof, abscisic acid (ABA) or a derivative thereof, methotrexate or a derivative thereof, cyclosporin A or a derivative thereof, FKCsA or a derivative thereof, trimethoprim (Tmp)-synthetic ligand for FKBP (SLF) or a derivative thereof, or any combination thereof.

Rapamycin analogs (rapalogs) include, but are not limited to those disclosed in U.S. Pat. No. 6,649,595, which rapalog structures are incorporated herein by reference in their entirety. In certain embodiments, a bridging factor is a rapalog with substantially reduced immunosuppressive effect as compared to rapamycin. In a preferred embodiment, the rapalog is AP21967 derivatives (also known as C-16-(S)-7-methylindolerapamycin, $IC_{50}$=10 nM, a chemically modified non-immunosuppressive rapamycin analogue).

A "substantially reduced immunosuppressive effect" refers to a rapalog having at least less than 0.1 to 0.005 times the immunosuppressive effect observed or expected for an equimolar amount of rapamycin, as measured either clinically or in an appropriate in vitro (e.g., inhibition of T cell proliferation) or in vivo surrogate of human immunosuppressive activity. In one embodiment, "substantially reduced immunosuppressive effect" refers to a rapalog having an EC50 value in such an in vitro assay that is at least 10 to 250 times larger than the EC50 value observed for rapamycin in the same assay. Other illustrative examples of rapalogs include, but are not limited to AP21967, everolimus, novolimus, pimecrolimus, ridaforolimus, tacrolimus, temsirolimus, umirolimus, and zotarolimus.

As used herein, "anchor domain" refers to an amino acid sequence or other molecule that promotes tethering, anchoring or association of a dimerizable salvage receptor to a cell surface. Exemplary anchor domains include an amino acid sequence with a structure that is stable in a cell membrane or an amino acid sequence that promotes the addition of a glycolipid (also known as glycosyl phosphatidylinositols or GPIs), or the like. By way of background, a GPI molecule is post-translationally attached to a protein target by a transamidation reaction, which results in the cleavage of a carboxy-terminal GPI signal sequence (see, e.g., White et al., *J Cell Sci.* 113:721, 2000) and the simultaneous transfer of the already synthesized GPI anchor molecule to the newly formed carboxy-terminal amino acid (see www.ncbi.nlm.nih.gov/books/NBK20711 for exemplary GPI anchors, which GPI anchors are incorporated by reference in their entirety). In certain embodiments, an anchor domain is a hydrophobic domain (e.g., transmembrane domain) or a GPI signal sequence. In some embodiments, a nucleic acid molecule encoding a polypeptide contemplated herein comprises an anchor domain, optionally wherein the anchor domain is a GPI molecule.

A "transmembrane domain" is a domain that anchors a polypeptide to the plasma membrane of a cell. The TM domain may be derived either from a natural, synthetic, semi-synthetic, or recombinant source.

An "intracellular signaling domain," refers to a polypeptide that participates in transducing the message of effective binding of a target antigen by a receptor expressed on an immune effector cell to into the interior of the immune effector cell to elicit effector cell function, e.g., activation, cytokine production, proliferation and cytotoxic activity, including the release of cytotoxic factors, or other cellular responses elicited with antigen binding to the receptor expressed on the immune effector cell.

The term "effector function" refers to a specialized function of an immune effector cell. Effector function of the T cell, for example, may be cytolytic activity or help or activity including the secretion of a cytokine. Thus, the term "intracellular signaling domain" refers to the portion of a protein which transduces the effector function signal and that directs the cell to perform a specialized function. While usually the entire intracellular signaling domain can be employed, in many cases it is not necessary to use the entire domain. To the extent that a truncated portion of an intracellular signaling domain is used, such truncated portion may be used in place of the entire domain as long as it transduces the effector function signal. The term intracellular signaling domain is meant to include any truncated portion of the intracellular signaling domain sufficient to transducing effector function signal.

It is known that signals generated through the TCR alone are insufficient for full activation of the T cell and that a secondary or co-stimulatory signal is also required. Thus, T cell activation can be said to be mediated by two distinct classes of intracellular signaling domains: primary signaling domains that initiate antigen-dependent primary activation through the TCR (e.g., a TCR/CD3 complex) and co-stimulatory signaling domains that act in an antigen-independent manner to provide a secondary or co-stimulatory signal.

A "primary signaling domain" refers to a signaling domain that regulates the primary activation of the TCR complex either in a stimulatory way, or in an inhibitory way. Primary signaling domains that act in a stimulatory manner may contain signaling motifs which are known as immunoreceptor tyrosine-based activation motifs or ITAMs. Illustrative examples of ITAM containing primary signaling domains that are suitable for use in particular embodiments include, but are not limited to those derived from FcRγ, FcRβ, CD3γ, CD3δ, CD3ε, CD3ζ, CD22, CD79a, CD79b, and CD66d.

As used herein, the term, "co-stimulatory signaling domain," or "co-stimulatory domain", refers to an intracellular signaling domain of a co-stimulatory molecule. Co-stimulatory molecules are cell surface molecules other than antigen receptors or Fc receptors that provide a second signal required for efficient activation and function of T lymphocytes upon binding to antigen. Illustrative examples of such co-stimulatory molecules from which co-stimulatory domains may be isolated include, but are not limited to: TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD278 (ICOS), DAP10, LAT, NKD2C, SLP76, TRIM, and ZAP70.

As used herein, the term "cancer" relates generally to a class of diseases or conditions in which abnormal cells divide without control and can invade nearby tissues.

As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor.

As used herein, the term "benign" or "non-malignant" refers to tumors that may grow larger but do not spread to other parts of the body. Benign tumors are self-limited and typically do not invade or metastasize.

A "cancer cell" refers to an individual cell of a cancerous growth or tissue. Cancer cells include both solid cancers and liquid cancers. A "tumor" or "tumor cell" refers generally to a swelling or lesion formed by an abnormal growth of cells, which may be benign, pre-malignant, or malignant. Most cancers form tumors, but liquid cancers, e.g., leukemia, do not necessarily form tumors. For those cancers that form tumors, the terms cancer (cell) and tumor (cell) are used interchangeably. The amount of a tumor in an individual is the "tumor burden" which can be measured as the number, volume, or weight of the tumor.

The term "relapse" refers to the diagnosis of return, or signs and symptoms of return, of a cancer after a period of improvement or remission.

"Remission," is also referred to as "clinical remission," and includes both partial and complete remission. In partial remission, some, but not all, signs and symptoms of cancer have disappeared. In complete remission, all signs and symptoms of cancer have disappeared, although cancer still may be in the body.

"Refractory" refers to a cancer that is resistant to, or non-responsive to, therapy with a particular therapeutic agent. A cancer can be refractory from the onset of treatment (i.e., non-responsive to initial exposure to the therapeutic agent), or as a result of developing resistance to the therapeutic agent, either over the course of a first treatment period or during a subsequent treatment period.

"Antigen negative" refers to a cell that does not express antigen or expresses a neglible amount of antigen that is undetectable. In one embodiment, antigen negative cells do not bind receptors directed to the antigen. In one embodiment, antigen negative cells do not substantially bind receptors directed to the antigen.

As used herein, the term "patient" refers to a subject that has been diagnosed with a particular disease, disorder, or condition that can be treated with the compositions and methods contemplated herein.

As used herein "treatment" or "treating," includes any beneficial or desirable effect on the symptoms or pathology of a disease or pathological condition, and may include even minimal reductions in one or more measurable markers of the disease or condition being treated. Treatment can involve optionally either the reduction of the disease or condition, or the delaying of the progression of the disease or condition, e.g., delaying tumor outgrowth. "Treatment" does not necessarily indicate complete eradication or cure of the disease or condition, or associated symptoms thereof.

As used herein, "prevent," and similar words such as "prevented," "preventing" etc., indicate an approach for preventing, inhibiting, or reducing the likelihood of the occurrence or recurrence of, a disease or condition. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

As used herein, the phrase "ameliorating at least one symptom of" refers to decreasing one or more symptoms of the disease or condition for which the subject is being treated. In particular embodiments, the disease or condition being treated is a cancer, wherein the one or more symptoms ameliorated include, but are not limited to, weakness, fatigue, shortness of breath, easy bruising and bleeding, frequent infections, enlarged lymph nodes, distended or painful abdomen (due to enlarged abdominal organs), bone or joint pain, fractures, unplanned weight loss, poor appetite, night sweats, persistent mild fever, and decreased urination (due to impaired kidney function).

By "enhance" or "promote," or "increase" or "expand" refers generally to the ability of a composition contemplated herein to produce, elicit, or cause a greater physiological response (i.e., downstream effects) compared to the response caused by either vehicle or a control molecule/composition. A measurable physiological response may include an increase in T cell expansion, activation, persistence, and/or an increase in cancer cell killing ability, among others apparent from the understanding in the art and the description herein. An "increased" or "enhanced" amount is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle or a control composition.

By "decrease" or "lower," or "lessen," or "reduce," or "abate" refers generally to the ability of composition contemplated herein to produce, elicit, or cause a lesser physiological response (i.e., downstream effects) compared to the response caused by either vehicle or a control molecule/composition. A "decrease" or "reduced" amount is typically a "statistically significant" amount, and may include an decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response (reference response) produced by vehicle, a control composition, or the response in a particular cell lineage.

By "maintain," or "preserve," or "maintenance," or "no change," or "no substantial change," or "no substantial decrease" refers generally to the ability of a composition contemplated herein to produce, elicit, or cause a substantially similar or comparable physiological response (i.e., downstream effects) in a cell, as compared to the response caused by either vehicle, a control molecule/composition, or the response in a particular cell lineage. A comparable response is one that is not significantly different or measurable different from the reference response.

C. Salvage Chimeric Antigen Receptors

In various embodiments, genetically engineered receptors that redirect cytotoxicity of immune effector cells toward cancer cells expressing a target antigen are provided. These genetically engineered receptors referred to herein as salvage chimeric antigen receptors (CARs). Salvage CARs are molecules that combine antibody-based specificity for a desired antigen with a T cell receptor-activating intracellular domain to generate a chimeric protein that exhibits an antigen specific cellular immune activity. Salvage CARs also contain a multimerization domain, which allows an antigen specific CAR to be redirected to another antigen. As used herein, the term, "chimeric," describes being composed of parts of different proteins or DNAs from different origins. T cells that comprise salvage CARs are referred to as CAR T cells that express a salvage CAR or salvage CAR T cells.

In particular embodiments, salvage CARs comprise an extracellular domain (also referred to as a binding domain or antigen-specific binding domain) that binds a target antigen, a multimerization domain, a transmembrane domain, and one or more intracellular signaling domains. In other particular embodiments, salvage CARs comprise an extracellular antigen-specific binding domain, a transmembrane domain, a multimerization domain, and one or more intracellular signaling domains. Engagement of the antigen binding domain of the salvage CAR with a target antigen on the surface of a target cell results in clustering of the salvage CAR and delivers an activation stimulus to the salvage CAR-containing cell. The main characteristic of salvage CARs are their ability to redirect immune effector cell specificity, thereby triggering proliferation, cytokine production, phagocytosis or production of molecules that can mediate cell death of the target antigen expressing cell in a major histocompatibility (MHC) independent manner, exploiting the cell specific targeting abilities of monoclonal antibodies, soluble ligands or cell specific co-receptors.

In various embodiments, salvage CARs contemplated herein offer increased targeting flexability and retargeting of cancers, optionally relapsed or refractory cancers that are antigen negative for the initial antigen targeted by the salvage CAR.

In particular embodiments, a salvage CAR comprises: an extracellular antigen binding domain; a multimerization domain; a transmembrane domain; one or more intracellular co-stimulatory signaling domains; and/or a primary signaling domain.

In particular embodiments, a salvage CAR comprises: an extracellular antigen binding domain; a transmembrane domain; a multimerization domain; one or more intracellular co-stimulatory signaling domains; and/or a primary signaling domain.

In particular embodiments, a salvage CAR comprises an extracellular binding domain that comprises antibody or antigen binding fragment thereof; one or more spacer domains and/or linkers; a multimerization domain, one or more hinge domains, a transmembrane domain including; one or more intracellular co-stimulatory signaling domains; and a primary signaling domain.

The salvage CARs contemplated in particular embodiments, comprise an antigen binding domain selected from the group consisting of: a Camel Ig, Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), and single-domain antibody (sdAb, Nanobody). In some preferred embodiments, the antigen binding domain is an scFv or a single-domain antibody.

In particular embodiments, an antigen binding domain binds a target antigen selected from the group consisting of: alpha folate receptor, 5T4, αvβ6 integrin, BCMA, B7-H3, B7-H6, CAIX, CD16, CD19, CD20, CD22, CD30, CD33, CD37, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, VEGFR2, and WT-1.

In particular embodiments, the target antigen is selected from the group consisting of: BCMA, CD19, CSPG4, PSCA, ROR1, and TAG72.

In particular embodiments, the target antigen is selected from the group consisting of: BCMA, CD19, CD20, CD22, CD23, CD33, CD37, CD52, CD80, and HLA-DR.

The CARs contemplated in particular embodiments, comprise one or more linker or spacer polypeptides between various domains of the salvage CAR to provide, in some cases, appropriate spacing and conformation of the salvage CAR domains. In particular embodiments, a linker is disposed between the heavy chain and light chain variable domains of an scFv in the antigen binding domain of a salvage CAR. In particular embodiments, a linker is a $(GGGGS)_n$ linker, wherein n=1, 2, 3, 4 or 5 (SEQ ID NO:10).

In certain embodiments, salvage CARs comprise a spacer domain that contains the CH2 and CH3 domains of IgG1, IgG4, or IgD.

Salvage CARs can also contain hinge domains in particular embodiments. Illustrative hinge domains suitable for use in the salvage CARs described herein include the hinge region derived from the extracellular regions of type 1 membrane proteins such as CD8α, and CD4, which may be wild-type hinge regions from these molecules or may be altered. In another embodiment, the hinge domain comprises a CD8α hinge region. In one embodiment, the hinge is a PD-1 hinge or CD152 hinge.

In particular embodiments, salvage CARs comprise one or more multimerization domains. In particular embodiments, the multimerization domain is extracellular. The multimerization domain may be disposed between the antigen binding domain and a transmembrane domain, between the antigen binding domain and a hinge domain, or between a hinge domain and a transmembrane domain. Illustrative examples of multimerization domains suitable for use in particular embodiments contemplated herein include an FKBP polypeptide, an FRB polypeptide, a calcineurin polypeptide, a cyclophilin polypeptide, a bacterial DHFR polypeptide, a PYL1 polypeptide, an ABI1 polypeptide, a GIB1 polypeptide, a GAI polypeptide, or variants thereof.

In one embodiment, the multimerization domain is selected from the group consisting of: an FKBP polypeptide, an FRB polypeptide, and variants thereof.

In one embodiment, the multimerization domain is selected from the group consisting of: an FKBP12 polypeptide and an FRB T2098L polypeptide.

In particular embodiments, a salvage CAR comprises a TM domain may be derived from (i.e., comprise at least the transmembrane region(s) of) the alpha or beta chain of the T-cell receptor, CDδ, CD3ε, CDγ, CD3ζ, CD4, CD5, CD8α, CD9, CD 16, CD22, CD27, CD28, CD33, CD37, CD45, CD64, CD71, CD80, CD86, CD 134, CD137, CD152, CD154, AMN, and PD1. In a particular embodiment, the TM domain is synthetic and predominantly comprises hydrophobic residues such as leucine and valine.

In one embodiment, salvage CARs comprise a TM domain derived from, PD1, CD152, or CD8α. In another embodiment, a salvage CAR comprises a TM domain derived from, PD1, CD152, or CD8α and a short oligo- or poly-peptide linker, preferably between 1, 2, 3, 4, 5, 6, 7, 8, 9, or 10 amino acids in length that links the TM domain and the intracellular signaling domain of the salvage CAR. A glycine-serine based linker provides a particularly suitable linker.

Salvage CARs contemplate herein comprise one or more intracellular signaling domains. In one embodiment, a salvage CAR comprises one or more co-stimulatory intracellular signaling domains and/or a primary signaling domain. In one embodiment, the intracellular signaling domain comprises an immunoreceptor tyrosine activation motif (ITAM).

Illustrative examples of ITAM containing primary signaling domains that are suitable for use in particular embodiments include those derived from FcRγ, FcRβ, CD3γ, CD3δ, CD3E, CD3ζ, CD22, CD79a, CD79b, and CD66d. In particular preferred embodiments, a salvage CAR comprises a CD3ζ primary signaling domain and one or more co-stimulatory signaling domains. The intracellular primary signaling and co-stimulatory signaling domains may be linked in any order in tandem to the carboxyl terminus of the transmembrane domain.

Illustrative examples of such co-stimulatory molecules include TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD278 (ICOS), DAP10, LAT, NKD2C, SLP76, TRIM, and ZAP70. In one embodiment, a salvage CAR comprises one or more co-stimulatory signaling domains selected from the group consisting of CD28, CD137, and CD134. In one embodiment, a salvage CAR comprises one or more co-stimulatory signaling domains selected from the group consisting of CD28, CD137, and CD134, and a CD3ζ primary signaling domain.

D. Dimerizable Salvage Receptors

In various embodiments, salvage CARs contemplated herein have been engineered to redirect cytotoxicity of immune effector cells toward relapsed or refractory cancer cells. Molecules that redirect or retarget the CAR T cells (salvage CAR T cells) toward the relapsed or refractory cancer cells are referred to herein as dimerizable salvage receptors. The dimerizable salvage receptors are molecules that combine antibody-based specificity for an antigen expressed on a relapsed or refractory cancer cell with a multimerization domain that interacts with the multimerization domain of a salvage CAR in the presence of a bridging factor. In the presence of the bridging factor, the dimerizable salvage receptor engages the salvage CAR molecule to re-initiate immune effector cell activity against the relapsed or refractory cancer cell. Without wishing to be bound by any particular theory, it is contemplated that CAR T cell therapy against an initial cancer antigen will result in remission. However, if the cancer should return and lacks expression or expresses little of the initial cancer antigen, then a dimerizable salvage receptor is selected that targets an antigen expressed on the relapsed or refractory cancer cells to re-initiate immune effector cell activity against the cancer.

In various embodiments, a dimerizable salvage receptor polypeptide is administered to a subject that has undergone CAR T cell therapy.

In various embodiments, a dimerizable salvage receptor polypeptide pre-loaded with bridging factor is administered to a subject that has undergone CAR T cell therapy.

In various embodiments, the salvage CAR T cells comprise an inducible promoter operably linked to a polynucleotide encoding a dimerizable salvage receptor.

In particular embodiments, a dimerizable salvage receptor comprises a bound bridging factor.

In particular embodiments, a dimerizable salvage receptor comprises an antigen binding domain and a multimerization domain.

In particular embodiments, a dimerizable salvage receptor comprises an antigen binding domain, a multimerization domain, and an anchor domain.

In particular embodiments, a dimerizable salvage receptor comprises an antigen binding domain, a multimerization domain, a hinge domain, and an anchor domain.

In particular embodiments, a dimerizable salvage receptor consists essentially of a signal peptide, an antigen binding domain, a linker domain, and a multimerization domain.

In particular embodiments, a dimerizable salvage receptor consists essentially of a signal peptide, an antigen binding domain, a linker domain, a multimerization domain, a hinge domain, and an anchor domain.

In particular embodiments, a dimerizable salvage receptor consists essentially of an antigen binding domain, a linker domain, and a multimerization domain.

In particular embodiments, a dimerizable salvage receptor consists essentially of an antigen binding domain, a linker domain, a multimerization domain, a hinge domain, and an anchor domain.

Dimerizable salvage receptors contemplated in particular embodiments, comprise an antibody or antigen binding fragment thereof. In particular embodiments, the antibody or antigen binding fragment is selected from the group consisting of a Camel Ig, Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), and single-domain antibody (sdAb, Nanobody). In one preferred embodiment, the dimerizable salvage receptor comprises an scFv antigen binding domain.

In particular embodiments, a dimerizable salvage receptor comprises an antigen binding domain binds an antigen selected from the group consisting of alpha folate receptor, 5T4, αvβ6 integrin, BCMA, B7-H3, B7-H6, CAIX, CD16, CD19, CD20, CD22, CD30, CD33, CD37, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, VEGFR2, and WT-1.

In one embodiment, antigen selected from the group consisting of BCMA, CD19, CSPG4, PSCA, ROR1, and TAG72; or the group consisting of BCMA, CD19, CD20, CD22, CD23, CD33, CD37, CD52, CD80, and HLA-DR.

In particular embodiments, a dimerizable salvage receptor comprises one or more linkers. The linkers may be disposed between the heavy chain and light chain variable regions of an antigen biding domain and/or between the antigen binding domain a multimerization domains. In one embodiment, the linker is a (GGGGS)$_n$ linker, wherein n=1, 2, 3, 4 or 5 (SEQ ID NO: 10).

In one embodiment, a dimerizable salvage receptor comprises a multimization domain selected from the group consisting of an FKBP polypeptide, an FRB polypeptide, a calcineurin polypeptide, a cyclophilin polypeptide, a bacterial DHFR polypeptide, a PYL1 polypeptide, an ABI1 polypeptide, a GIB1 polypeptide, a GAI polypeptide, and variants thereof.

In one embodiment, a multimerization domain comprises an FKBP polypeptide, an FRB polypeptide, or variants thereof.

In one embodiment, a multimerization domain comprises an FKBP12 polypeptide or an FRB T2098L polypeptide.

In particular embodiments, a dimerizable salvage receptor comprises a hinge domain. In one embodiment, the hinge domain is selected from the group consisting essentially of a CD4 hinge, a CD8α hinge, a PD-1 hinge, and a CD152 hinge.

In particular embodiments, a dimerizable salvage receptor comprises a TM domain may be derived from (i.e., comprise at least the transmembrane region(s) of) the alpha or beta chain of the T-cell receptor, CDδ, CD3ε, CDγ, CD3ζ, CD4, CD5, CD8α, CD9, CD 16, CD22, CD27, CD28, CD33, CD37, CD45, CD64, CD71, CD80, CD86, CD 134, CD137, CD152, CD154, AMN, and PD1. In a particular embodiment, the TM domain is synthetic and predominantly comprises hydrophobic residues such as leucine and valine.

In particular embodiments, a dimerizable salvage receptor comprises a GPI anchor molecule.

E. Salvage Car System

Relapsed or refractory cancers are a prevelant problem plaguing the cellular immunotherapy field. The salvage CAR systems contemplated herein provide a highly efficient solution for treating relapsed/refractory cancers, especially those that no longer express the antigen that was initially targeted (the initial target antigen). For example, a patient treated for a CD19 expressing leukemia with anti-CD19 CAR T cells may initially show improvement and cancer regression, but eventually, the leukemia may return, lacking CD19 expression. This scenario presents a serious problem because the CAR T cells residing in the patient are specific to CD19 and thus, the relapsed or refractory CD19 negative cancer cells are invisible to the immune system and will grow unchecked without additional therapeutic intervention. The salvage CAR system provides that intervention in the form of an additional targeting receptor, referred to herein as a dimerizable salvage receptor.

In various embodiments, a salvage CAR system is provided to a subject in order to treat a cancer, and in certain preferred embodiments, a relapsed or refractory cancer. The salvage CAR system comprises CAR T cells comprising a salvage CAR directed against a first antigen expressed on a cancer cell, a dimerizable salvage receptor directed against a second antigen expressed on a cancer cell, and a bridging factor.

In various embodiments, the dimerizable salvage receptor pre-loaded or bound to bridging factor may be provided or administered to a subject.

In various other embodiments, the dimerizable salvage receptor is not pre-loaded or bound to bridging factor when provided or administered to a subject.

Without wishing to be bound by any particular theory, it is contemplated that once a relapsed/refractory cancer cancer manifests itself in a subject that has been treated with CAR T cells that express a salvage CAR directed to a first antigen that is no longer expressed, or no longer substantially expressed, on the relapsed/refractory cancer, a dimerizable salvage receptor directed to a second antigen that is expressed or substantially expressed on the relapsed or refractory cancer cells is administered to the subject. The subject is further administered a bridging factor that binds a multimerization domain of the salvage CAR and a multimerization domain of the dimerizable salvage receptor; thereby promoting association between the salvage CAR and the salvage receptor. This association re-engages the CAR signaling pathways and promotes immune effector cell activity directed against the relapsed/refractory cancer cells expressing the second antigen.

In particular embodiments, a salvage CAR system comprises a CAR T cell (salvage CAR T cell) comprising a CAR that binds a first antigen; a dimerizable salvage receptor that binds a second antigen; and a bridging factor that binds the salvage CAR and the dimerizable salvage receptor to form a functionally active salvage CAR against a cancer cell that expresses the second antigen.

In one embodiment, the dimerizable salvage receptor is administered to the subject.

In one embodiment, the salvage CAR T cell comprises a nucleic acid comprising an inducible promoter and a polynucleotide encoding the dimerizable salvage receptor.

In some embodiments, the salvage CAR and dimerizable salvage receptor are designed to bind different epitopes on the same antigen.

In preferred embodiments, the first antigen is different than the second antigen.

In particular embodiments, the first antigen and the second antigen are independently selected from the group consisting of: alpha folate receptor, 5T4, αvβ6 integrin, BCMA, B7-H3, B7-H6, CAIX, CD16, CD19, CD20, CD22, CD30, CD33, CD37, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, VEGFR2, and WT-1.

In one embodiment, salvage CAR systems target B cell malignancies.

Salvage CAR systems contemplated in particular embodiments comprise a CAR T cell comprising a salvage CAR that targets a first antigen selected from the group consisting of: BCMA, CD19, CD20, CD22, CD23, CD33, CD37, CD52, CD80, and HLA-DR, and a dimerizable salvage receptor that targets a second antigen selected from the group consisting of: BCMA, CD19, CD20, CD22, CD23, CD33, CD37, CD52, CD80, and HLA-DR.

In particular embodiments, a salvage CAR system comprises a CAR T cell comprising a salvage CAR that targets BCMA and a dimerizable salvage receptor that targets a second antigen selected from the group consisting of: CD19, CD20, CD22, CD23, CD33, CD37, CD52, CD80, and HLA-DR.

In certain embodiments, a salvage CAR system comprises a CAR T cell comprising a salvage CAR that targets CD19 and a dimerizable salvage receptor that targets a second antigen selected from the group consisting of BCMA, CD20, CD22, CD23, CD33, CD37, CD52, CD80, and HLA-DR.

In one embodiment, a salvage CAR system comprises a CAR T cell comprising a salvage CAR that targets BCMA and a dimerizable salvage receptor that targets CD19.

In another embodiment, a salvage CAR system comprises a CAR T cell comprising a salvage CAR that targets CD19 and a dimerizable salvage receptor that targets BCMA.

The salvage CAR system is a flexible cancer targeting system where a salvage CAR that has initial specificity to one target antigen is co-opted to recognize a second target antigen through bridging factor mediated association of multimerization domains in the salvage CAR and dimerizable salvage receptor.

In various embodiments, the salvage CAR multimerization domain and the dimerizable salvage receptor multimerization domain are a pair selected from FKBP and FRB, FKBP and calcineurin, FKBP and cyclophilin, FKBP and bacterial DHFR, calcineurin and cyclophilin, PYL1 and ABI1, or GIB1 and GAI, or variants thereof.

In one embodiment, the salvage CAR multimerization domain comprises an FKBP polypeptide or variant thereof, and the dimerizable salvage receptor multimerization domain comprises an FRB polypeptide or variant thereof.

In one embodiment, the salvage CAR multimerization domain comprises an FRB polypeptide or variant thereof, and the dimerizable salvage receptor multimerization domain comprises an FKBP polypeptide or variant thereof.

In one embodiment, the bridging factor is AP21967, sirolimus, everolimus, novolimus, pimecrolimus, ridaforolimus, tacrolimus, temsirolimus, umirolimus, or zotarolimus.

In a particular embodiment, a salvage CAR system comprises a CAR T cell comprising a salvage CAR that has an scFv specific for BCMA, an FRB T2098L multimerization domain, a transmembrane domain, a costimulatory domain of 4-1BB, and an ITAM or primary signaling domain of CD3ζ and a dimerizable salvage receptor that has an scFv specific for CD19, an FKBP12 multimerization domain, and optionally an anchor domain, wherein the bridging factor is AP21967.

In one embodiment, a salvage CAR system comprises a CAR T cell comprising a salvage CAR that has an scFv specific for CD19, an FRB T2098L multimerization domain, a transmembrane domain, a costimulatory domain of 4-1BB, and an ITAM or primary signaling domain of CD3ζ and a dimerizable salvage receptor that has an scFv specific for BCMA, an FKBP12 multimerization domain, and optionally an anchor domain, wherein the bridging factor is AP21967.

In a particular embodiment, a salvage CAR system comprises a CAR T cell comprising a salvage CAR that has an scFv specific for BCMA, an FKBP12 multimerization domain, a transmembrane domain, a costimulatory domain of 4-1BB, and an ITAM or primary signaling domain of CD3ζ and a dimerizable salvage receptor that has an scFv specific for CD19, an FRB T2098L multimerization domain, and optionally an anchor domain, wherein the bridging factor is AP21967.

In one embodiment, a salvage CAR system comprises a CAR T cell comprising a salvage CAR that has an scFv specific for CD19, an FKBP12 multimerization domain, a transmembrane domain, a costimulatory domain of 4-1BB, and an ITAM or primary signaling domain of CD3ζ and a dimerizable salvage receptor that has an scFv specific for BCMA, an FRB T2098L multimerization domain, and optionally an anchor domain, wherein the bridging factor is AP21967.

In another embodiment, a salvage CAR system comprises a CAR T cell comprising a salvage CAR that has scFv specific for BCMA, an FRB multimerization domain, a transmembrane domain, a costimulatory domain of 4-1BB, and an ITAM or primary signaling domain of CD3ζ and a dimerizable salvage receptor that has an scFv specific for CD19, an FKBP12 multimerization domain, and optionally an anchor domain, wherein the bridging factor is Rapamycin, temsirolimus or everolimus.

In another embodiment, a salvage CAR system comprises a CAR T cell comprising a salvage CAR that has scFv specific for CD19, an FRB multimerization domain, a transmembrane domain, a costimulatory domain of 4-1BB, and an ITAM or primary signaling domain of CD3ζ and a dimerizable salvage receptor that has an scFv specific for BCMA, an FKBP12 multimerization domain, and optionally an anchor domain, wherein the bridging factor is Rapamycin, temsirolimus or everolimus.

In another embodiment, a salvage CAR system comprises a CAR T cell comprising a salvage CAR that has scFv specific for BCMA, an FKBP12 multimerization domain, a transmembrane domain, a costimulatory domain of 4-1BB, and an ITAM or primary signaling domain of CD3ζ and a dimerizable salvage receptor that has an scFv specific for CD19, an FRB multimerization domain, and optionally an anchor domain, wherein the bridging factor is Rapamycin, temsirolimus or everolimus.

In another embodiment, a salvage CAR system comprises a CAR T cell comprising a salvage CAR that has scFv specific for CD19, an FKBP12 multimerization domain, a transmembrane domain, a costimulatory domain of 4-1BB, and an ITAM or primary signaling domain of CD3ζ and a dimerizable salvage receptor that has an scFv specific for BCMA, an FRB multimerization domain, and optionally an anchor domain, wherein the bridging factor is Rapamycin, temsirolimus or everolimus.

F. Polypeptides

Various polypeptides are contemplated herein, including, but not limited to, salvage CAR polypeptides, dimerizable salvage receptor polypeptides and fragments thereof, cells and compositions comprising the same, and vectors that express polypeptides.

"Polypeptide," "polypeptide fragment," "peptide" and "protein" are used interchangeably, unless specified to the contrary, and according to conventional meaning, i.e., as a sequence of amino acids. Polypeptides may be synthesized or recombinantly produced. Polypeptides are not limited to a specific length, e.g., they may comprise a full length protein sequence or a fragment of a full length protein, and may include post-translational modifications of the polypeptide, for example, glycosylations, acetylations, phosphorylations and the like, as well as other modifications known in the art, both naturally occurring and non-naturally occurring. In various embodiments, the polypeptides comprise a signal (or leader) sequence at the N-terminal end of the protein, which co-translationally or post-translationally directs transfer of the protein. Illustrative examples of suitable signal sequences useful in polypeptides contemplated herein include, but are not limited to the IgG1 heavy chain signal polypeptide, a CD8α signal polypeptide, or a human GM-CSF receptor alpha signal polypeptide. Polypeptides can be prepared using any of a variety of well-known recombinant and/or synthetic techniques. Polypeptides contemplated herein specifically encompass sequences that have deletions from, additions to, and/or substitutions of one or more amino acids of a salvage CAR or dimerizable salvage receptor contemplated herein.

An "isolated peptide" or an "isolated polypeptide" and the like, as used herein, refer to in vitro isolation and/or purification of a peptide or polypeptide molecule from a cellular environment, and from association with other components of the cell, i.e., it is not significantly associated with in vivo substances. Similarly, an "isolated cell" refers to a cell that has been obtained from an in vivo tissue or organ and is substantially free of extracellular matrix.

Polypeptides include "polypeptide variants." Polypeptide variants may differ from a naturally occurring polypeptide in one or more substitutions, deletions, additions and/or insertions. Such variants may be naturally occurring or may be synthetically generated, for example, by modifying one or more of the above polypeptide sequences. For example, in particular embodiments, it may be desirable to improve the binding affinity and/or other biological properties of a polypeptide by introducing one or more substitutions, deletions, additions and/or insertions the polypeptide. In particular embodiments, polypeptides include polypeptides having at least about 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 86%, 97%, 98%, or 99% amino acid identity to any of the reference sequences contemplated herein, typically where the variant maintains at least one biological activity of the reference sequence.

Polypeptides include "polypeptide fragments." Polypeptide fragments refer to a polypeptide, which can be monomeric or multimeric that has an amino-terminal deletion, a carboxyl-terminal deletion, and/or an internal deletion or substitution of a naturally-occurring or recombinantly-produced polypeptide. In certain embodiments, a polypeptide fragment can comprise an amino acid chain at least 5 to about 500 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, or 450 amino acids long. Particularly useful polypeptide fragments include functional domains, including antigen-binding domains or fragments of antibodies The polypeptide may also be fused in-frame or conjugated to a linker or other sequence for ease of synthesis, purification or identification of the polypeptide (e.g., poly-His), or to enhance binding of the polypeptide to a solid support.

As noted above, polypeptides may be altered in various ways including amino acid substitutions, deletions, truncations, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (1985, *Proc. Natl. Acad. Sci. USA*. 82: 488-492), Kunkel et al., (1987, *Methods in Enzymol*, 154: 367-382), U.S. Pat. No. 4,873,192, Watson, J. D. et al., (*Molecular Biology of the Gene*, Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) *Atlas of Protein Sequence and Structure* (Natl. Biomed. Res. Found., Washington, D.C.).

In certain embodiments, a polypeptide variant comprises one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Modifications may be made in the structure of the polynucleotides and polypeptides contemplated in particular embodiments and still obtain a functional molecule that encodes a variant or derivative polypeptide with desirable characteristics. When it is desired to alter the amino acid sequence of a polypeptide to create an equivalent, or even an improved, variant polypeptide, one skilled in the art, for example, can change one or more of the codons of the encoding DNA sequence, e.g., according to Table 1.

TABLE 1

Amino Acid Codons

| Amino Acids | One letter code | Three letter code | Codons | | | | | |
|---|---|---|---|---|---|---|---|---|
| Alanine | A | Ala | GCA | GCC | GCG | | GCU | |
| Cysteine | C | Cys | UGC | | | UGU | | |
| Aspartic acid | D | Asp | GAC | | | GAU | | |
| Glutamic acid | E | Glu | GAA | | | GAG | | |
| Phenylalanine | F | Phe | UUC | | | UUU | | |
| Glycine | G | Gly | GGA | GGC | GGG | | GGU | |
| Histidine | H | His | CAC | | | CAU | | |
| Isoleucine | I | Iso | AUA | AUC | | AUU | | |
| Lysine | K | Lys | AAA | | | AAG | | |
| Leucine | L | Leu | UUA | UUG | CUA | CUC | CUG | CUU |
| Methionine | M | Met | | | AUG | | | |
| Asparagine | N | Asn | AAC | | | AAU | | |
| Proline | P | Pro | CCA | CCC | CCG | | CCU | |
| Glutamine | Q | Gln | CAA | | | CAG | | |
| Arginine | R | Arg | AGA | AGG | CGA | CGC | CGG | CGU |
| Serine | S | Ser | AGC | AGU | UCA | UCC | UCG | UCU |
| Threonine | T | Thr | ACA | ACC | ACG | | ACU | |
| Valine | V | Val | GUA | GUC | GUG | | GUU | |
| Tryptophan | W | Trp | | | UGG | | | |
| Tyrosine | Y | Tyr | UAC | | | UAU | | |

Guidance in determining which amino acid residues can be substituted, inserted, or deleted without abolishing biological activity can be found using computer programs well known in the art, such as DNASTAR, DNA Strider, Geneious, Mac Vector, or Vector NTI software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids. In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. *Molecular Biology of the Gene*, 4th Edition, 1987, The Benjamin/Cummings Pub. Co., p. 224).

In making such changes, the hydropathic index of amino acids may be considered. The importance of the hydropathic amino acid index in conferring interactive biologic function on a protein is generally understood in the art (Kyte and Doolittle, 1982, incorporated herein by reference). Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions may be based on the relative similarity of the amino acid side-chain substituents, for example, their hydrophobicity, hydrophilicity, charge, size, and the like.

Polypeptide variants further include glycosylated forms, aggregative conjugates with other molecules, and covalent conjugates with unrelated chemical moieties (e.g., pegylated molecules). Covalent variants can be prepared by linking functionalities to groups which are found in the amino acid chain or at the N- or C-terminal residue, as is known in the art. Variants also include allelic variants, species variants, and muteins. Truncations or deletions of regions which do not affect functional activity of the proteins are also variants.

In one embodiment, where expression of two or more polypeptides is desired, the polynucleotide sequences encoding them can be separated by an IRES sequence as discussed elsewhere herein. In another embodiment, two or more polypeptides can be expressed as a fusion protein that comprises one or more self-cleaving polypeptide sequences.

Polypeptides contemplated in particular embodiments include fusion polypeptides. In preferred embodiments, fusion polypeptides and polynucleotides encoding fusion polypeptides are provided, e.g., salvage CARs or dimerizable salvage receptors. Fusion polypeptides and fusion proteins refer to a polypeptide having at least two, three, four, five, six, seven, eight, nine, or ten or more polypeptide segments. Fusion polypeptides are typically linked C-terminus to N-terminus, although they can also be linked C-terminus to C-terminus, N-terminus to N-terminus, or N-terminus to C-terminus. The polypeptides of the fusion protein can be in any order or a specified order. Fusion polypeptides or fusion proteins can also include conservatively modified variants, polymorphic variants, alleles, mutants, subsequences, and interspecies homologs, so long as the desired transcriptional activity of the fusion polypeptide is preserved. Fusion polypeptides may be produced by chemical synthetic methods or by chemical linkage between the two moieties or may generally be prepared using other standard techniques. Ligated DNA sequences comprising the fusion polypeptide are operably linked to suitable transcriptional or translational control elements as discussed elsewhere herein.

In one embodiment, a fusion partner comprises a sequence that assists in expressing the protein (an expression enhancer) at higher yields than the native recombinant protein. Other fusion partners may be selected so as to increase the solubility of the protein or to enable the protein to be targeted to desired intracellular compartments or to facilitate transport of the fusion protein through the cell membrane.

Fusion polypeptides may further comprise a polypeptide cleavage signal between each of the polypeptide domains described herein. In addition, a polypeptide cleavage site can be put into any linker peptide sequence. Exemplary polypeptide cleavage signals include polypeptide cleavage recognition sites such as protease cleavage sites, nuclease cleavage sites (e.g., rare restriction enzyme recognition sites, self-cleaving ribozyme recognition sites), and self-cleaving viral oligopeptides (see deFelipe and Ryan, 2004. *Traffic*, 5(8); 616-26).

Suitable protease cleavages sites and self-cleaving peptides are known to the skilled person (see, e.g., in Ryan et al., 1997. *J Gener. Virol.* 78, 699-722; Scymczak et al. (2004) *Nature Biotech.* 5, 589-594). Exemplary protease cleavage sites include, but are not limited to the cleavage sites of potyvirus NIa proteases (e.g., tobacco etch virus protease), potyvirus HC proteases, potyvirus P1 (P35) proteases, byovirus NIa proteases, byovirus RNA-2-encoded proteases, aphthovirus L proteases, enterovirus 2A proteases, rhinovirus 2A proteases, picomna 3C proteases, comovirus 24K proteases, nepovirus 24K proteases, RTSV (rice tungro spherical virus) 3C-like protease, PYVF (parsnip yellow fleck virus) 3C-like protease, heparin, thrombin, factor Xa and enterokinase. Due to its high cleavage stringency, TEV (tobacco etch virus) protease cleavage sites are preferred in one embodiment, e.g., EXXYXQ(G/S) (SEQ ID NO: 18), for example, ENLYFQG (SEQ ID NO: 19) and ENLYFQS (SEQ ID NO: 20) wherein X represents any amino acid (cleavage by TEV occurs between Q and G or Q and L).

In a particular embodiment, self-cleaving peptides include those polypeptide sequences obtained from potyvirus and cardiovirus 2A peptides, FMDV (foot-and-mouth disease virus), equine rhinitis A virus, Thosea asigna virus and porcine teschovirus.

In certain embodiments, the self-cleaving polypeptide site comprises a 2A or 2A-like site, sequence or domain (Donnelly et al., 2001.1 *Gen. Virol.* 82:1027-1041). Exemplary 2A sites are shown in Table 2.

TABLE 2

| | |
|---|---|
| SEQ ID NO: 21 | GSGATNFSLLKQAGDVEENPGP |
| SEQ ID NO: 22 | ATNFSLLKQAGDVEENPGP |
| SEQ ID NO: 23 | LLKQAGDVEENPGP |
| SEQ ID NO: 24 | GSGEGRGSLLTCGDVEENPGP |
| SEQ ID NO: 25 | EGRGSLLTCGDVEENPGP |
| SEQ ID NO: 26 | LLTCGDVEENPGP |
| SEQ ID NO: 27 | GSGQCTNYALLKLAGDVESNPGP |
| SEQ ID NO: 28 | QCTNYALLKLAGDVESNPGP |
| SEQ ID NO: 29 | LLKLAGDVESNPGP |

TABLE 2-continued

| SEQ ID NO: 30 | GSGVKQTLNFDLLKLAGDVESNPGP |
| --- | --- |
| SEQ ID NO: 31 | VKQTLNFDLLKLAGDVESNPGP |
| SEQ ID NO: 32 | LLKLAGDVESNPGP |
| SEQ ID NO: 33 | LLNFDLLKLAGDVESNPGP |
| SEQ ID NO: 34 | TLNFDLLKLAGDVESNPGP |
| SEQ ID NO: 35 | LLKLAGDVESNPGP |
| SEQ ID NO: 36 | NFDLLKLAGDVESNPGP |
| SEQ ID NO: 37 | QLLNFDLLKLAGDVESNPGP |
| SEQ ID NO: 38 | APVKQTLNFDLLKLAGDVESNPGP |
| SEQ ID NO: 39 | VTELLYRMKRAETYCPRPLLAIHPTEARHKQKIVAPVKQT |
| SEQ ID NO: 40 | LNFDLLKLAGDVESNPGP |
| SEQ ID NO: 41 | LLAIHPTEARHKQKIVAPVKQTLNFDLLKLAGDVESNPGP |
| SEQ ID NO: 42 | EARHKQKIVAPVKQTLNFDLLKLAGDVESNPGP |

In preferred embodiments, a polypeptide comprises a salvage CAR polypeptide or dimerizable salvage receptor polypeptide.

G. Polynucleotides

In particular embodiments, a polynucleotide encoding one or more polypeptides is provided. As used herein, the terms "polynucleotide" or "nucleic acid" refers to messenger RNA (mRNA), RNA, genomic RNA (gRNA), plus strand RNA (RNA(+)), minus strand RNA (RNA(−)), genomic DNA (gDNA), complementary DNA (cDNA) or recombinant DNA. Polynucleotides include single and double stranded polynucleotides. In particular embodiments, polynucleotides include polynucleotides or variants having at least about 50%, 55%, 60%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 86%, 97%, 98%, or 99% sequence identity to any of the reference sequences contemplated herein. In various illustrative embodiments, polynucleotides include expression vectors, viral vectors, and transfer plasmids, and compositions and cells comprising the same.

In particular embodiments, polynucleotides are provided that encode at least about 5, 10, 25, 50, 100, 150, 200, 250, 300, 350, 400, 500, 1000, 1250, 1500, 1750, or 2000 or more contiguous amino acid residues of a polypeptide, as well as all intermediate lengths. It will be readily understood that "intermediate lengths," in this context, means any length between the quoted values, such as 6, 7, 8, 9, etc., 101, 102, 103, etc.; 151, 152, 153, etc.; 201, 202, 203, etc.

As used herein, the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms include polynucleotides in which one or more nucleotides have been added or deleted, or replaced with different nucleotides compared to a reference polynucleotide. In this regard, it is well understood in the art that certain alterations inclusive of mutations, additions, deletions and substitutions can be made to a reference polynucleotide whereby the altered polynucleotide retains the biological function or activity of the reference polynucleotide.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 86%, 97%, 98%, or 99% sequence identity to any of the reference sequences described herein, typically where the polypeptide variant maintains at least one biological activity of the reference polypeptide.

Terms used to describe sequence relationships between two or more polynucleotides or polypeptides include "reference sequence," "comparison window," "sequence identity," "percentage of sequence identity," and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, WI, USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., *Current Protocols in Molecular Biology*, John Wiley & Sons Inc, 1994-1998, Chapter 15.

As used herein, "isolated polynucleotide" refers to a polynucleotide that has been purified from the sequences which flank it in a naturally-occurring state, e.g., a DNA fragment that has been removed from the sequences that are normally adjacent to the fragment. An "isolated polynucleotide" also refers to a complementary DNA (cDNA), a recombinant DNA, or other polynucleotide that does not exist in nature and that has been made by the hand of man.

Terms that describe the orientation of polynucleotides include: 5' (normally the end of the polynucleotide having a free phosphate group) and 3' (normally the end of the polynucleotide having a free hydroxyl (OH) group). Polynucleotide sequences can be annotated in the 5' to 3' orientation or the 3' to 5' orientation. For DNA and mRNA, the 5' to 3' strand is designated the "sense," "plus," or "coding" strand because its sequence is identical to the sequence of the premessenger (premRNA) [except for uracil (U) in RNA, instead of thymine (T) in DNA]. For DNA and mRNA, the complementary 3' to 5' strand which is the strand transcribed by the RNA polymerase is designated as "template," "antisense," "minus," or "non-coding" strand. As used herein, the term "reverse orientation" refers to a 5' to 3' sequence written in the 3' to 5' orientation or a 3' to 5' sequence written in the 5' to 3' orientation.

The terms "complementary" and "complementarity" refer to polynucleotides (i.e., a sequence of nucleotides) related by the base-pairing rules. For example, the complementary strand of the DNA sequence 5' A G T C A T G 3' is 3' T C A G T A C 5'. The latter sequence is often written as the reverse complement with the 5' end on the left and the 3' end on the right, 5' C A T G A C T 3'. A sequence that is equal to its reverse complement is said to be a palindromic sequence. Complementarity can be "partial," in which only some of the nucleic acids' bases are matched according to the base pairing rules. Or, there can be "complete" or "total" complementarity between the nucleic acids.

Moreover, it will be appreciated by those of ordinary skill in the art that, as a result of the degeneracy of the genetic code, there are many nucleotide sequences that encode a polypeptide, or fragment of variant thereof, as described herein. Some of these polynucleotides bear minimal homology to the nucleotide sequence of any native gene. Nonetheless, polynucleotides that vary due to differences in codon usage are specifically contemplated in particular embodiments, for example polynucleotides that are optimized for human and/or primate codon selection. In particular embodiments, the polynucleotides are codon optimized for expression and/or stability. Further, alleles of the genes comprising the polynucleotide sequences provided herein may also be used. Alleles are endogenous genes that are altered as a result of one or more mutations, such as deletions, additions and/or substitutions of nucleotides.

The term "nucleic acid cassette" as used herein refers to genetic sequences within a vector which can express a RNA, and subsequently a protein. The nucleic acid cassette contains the gene of interest. The nucleic acid cassette is positionally and sequentially oriented within the vector such that the nucleic acid in the cassette can be transcribed into RNA, and when necessary, translated into a protein or a polypeptide, undergo appropriate post-translational modifications required for activity in the transformed cell, and be translocated to the appropriate compartment for biological activity by targeting to appropriate intracellular compartments or secretion into extracellular compartments. Preferably, the cassette has its 3' and 5' ends adapted for ready insertion into a vector, e.g., it has restriction endonuclease sites at each end.

In particular embodiments, polynucleotides include at least one polynucleotide-of-interest. As used herein, the term "polynucleotide-of-interest" refers to a polynucleotide encoding a polypeptide (i.e., a polypeptide-of-interest), inserted into an expression vector that is desired to be expressed. A vector may comprise 1, 2, 3, 4, 5, 6, 7, 8, 9, or 10 polynucleotides-of-interest. In certain embodiments, the polynucleotide-of-interest encodes a polypeptide that provides a therapeutic effect in the treatment or prevention of a disease or disorder. Polynucleotides-of-interest, and polypeptides encoded therefrom, include both polynucleotides that encode wild-type polypeptides, as well as functional variants and fragments thereof. In particular embodiments, a functional variant has at least 80%, at least 90%, at least 95%, or at least 99% identity to a corresponding wild-type reference polynucleotide or polypeptide sequence. In certain embodiments, a functional variant or fragment has at least 50%, at least 60%, at least 70%, at least 80%, or at least 90% of a biological activity of a corresponding wild-type polypeptide.

In one embodiment, the polynucleotide-of-interest is a template to transcribe miRNA, siRNA, or shRNA, ribozyme, or other inhibitory RNA. In various other embodiments, a polynucleotide comprises a polynucleotide-of-interest encoding a salvage CAR and one or more additional polynucleotides-of-interest including, but not limited to, an inhibitory nucleic acid sequence including, without limitation: an siRNA, an miRNA, an shRNA, and a ribozyme.

As used herein, the terms "siRNA" or "short interfering RNA" refer to a short polynucleotide sequence that mediates a process of sequence-specific post-transcriptional gene silencing, translational inhibition, transcriptional inhibition, or epigenetic RNAi in animals (Zamore et al., 2000, *Cell*, 101, 25-33; Fire et al., 1998, *Nature*, 391, 806; Hamilton et al., 1999, *Science*, 286, 950-951; Lin et al., 1999, *Nature*, 402, 128-129; Sharp, 1999, *Genes & Dev.*, 13, 139-141; and Strauss, 1999, *Science*, 286, 886). In certain embodiments, an siRNA comprises a first strand and a second strand that have the same number of nucleosides; however, the first and second strands are offset such that the two terminal nucleosides on the first and second strands are not paired with a residue on the complimentary strand. In certain instances, the two nucleosides that are not paired are thymidine resides. The siRNA should include a region of sufficient homology to the target gene, and be of sufficient length in terms of nucleotides, such that the siRNA, or a fragment thereof, can mediate down regulation of the target gene. Thus, an siRNA includes a region which is at least partially complementary to the target RNA. It is not necessary that there be perfect complementarity between the siRNA and the target, but the correspondence must be sufficient to enable the siRNA, or a cleavage product thereof, to direct sequence specific silencing, such as by RNAi cleavage of the target RNA. Complementarity, or degree of homology with the target strand, is most critical in the antisense strand. While perfect complementarity, particularly in the antisense strand, is often desired, some embodiments include one or more, but preferably 10, 8, 6, 5, 4, 3, 2, or fewer mismatches with respect to the target RNA. The mismatches are most tolerated in the terminal regions, and if present are preferably in a terminal region or regions, e.g., within 6, 5, 4, or 3 nucleotides of the 5' and/or 3' terminus. The sense strand need only be sufficiently complementary with the antisense strand to maintain the overall double-strand character of the molecule.

In addition, an siRNA may be modified or include nucleoside analogs. Single stranded regions of an siRNA may be modified or include nucleoside analogs, e.g., the unpaired region or regions of a hairpin structure, e.g., a region which links two complementary regions, can have modifications or nucleoside analogs. Modification to stabilize one or more 3'- or 5'-terminus of an siRNA, e.g., against exonucleases, or to favor the antisense siRNA agent to enter into RISC are also useful. Modifications can include C3 (or C6, C7, C12) amino linkers, thiol linkers, carboxyl linkers, non-nucleotidic spacers (C3, C6, C9, C12, abasic, triethylene glycol, hexaethylene glycol), special biotin or fluorescein reagents that come as phosphoramidites and that have another DMT-protected hydroxyl group, allowing multiple couplings during RNA synthesis. Each strand of an siRNA can be equal to or less than 30, 25, 24, 23, 22, 21, or 20 nucleotides in length. The strand is preferably at least 19 nucleotides in length. For example, each strand can be between 21 and 25 nucleotides in length. Preferred siRNAs have a duplex region of 17, 18, 19, 29, 21, 22, 23, 24, or 25 nucleotide pairs, and one or more overhangs of 2-3 nucleotides, preferably one or two 3' overhangs, of 2-3 nucleotides.

As used herein, the terms "miRNA" or "microRNA" s refer to small non-coding RNAs of 20-22 nucleotides, typically excised from ~70 nucleotide foldback RNA precursor structures known as pre-miRNAs. miRNAs negatively regulate their targets in one of two ways depending on the degree of complementarity between the miRNA and the target. First, miRNAs that bind with perfect or nearly perfect complementarity to protein-coding mRNA sequences induce the RNA-mediated interference (RNAi) pathway. miRNAs that exert their regulatory effects by binding to imperfect complementary sites within the 3' untranslated regions (UTRs) of their mRNA targets, repress target-gene expression post-transcriptionally, apparently at the level of translation, through a RISC complex that is similar to, or possibly identical with, the one that is used for the RNAi pathway. Consistent with translational control, miRNAs that use this mechanism reduce the protein levels of their target genes, but the mRNA levels of these genes are only minimally affected. miRNAs encompass both naturally occurring miRNAs as well as artificially designed miRNAs that can specifically target any mRNA sequence. For example, in one embodiment, the skilled artisan can design short hairpin RNA constructs expressed as human miRNA (e.g., miR-30 or miR-21) primary transcripts. This design adds a Drosha processing site to the hairpin construct and has been shown to greatly increase knockdown efficiency (Pusch et al., 2004). The hairpin stem consists of 22-nt of dsRNA (e.g., antisense has perfect complementarity to desired target) and a 15-19-nt loop from a human miR. Adding the miR loop and miR30 flanking sequences on either or both sides of the hairpin results in greater than 10-fold increase in Drosha and Dicer processing of the expressed hairpins when compared with conventional shRNA designs without microRNA. Increased Drosha and Dicer processing translates into greater siRNA/miRNA production and greater potency for expressed hairpins.

As used herein, the terms "shRNA" or "short hairpin RNA" refer to double-stranded structure that is formed by a single self-complementary RNA strand. shRNA constructs containing a nucleotide sequence identical to a portion, of either coding or non-coding sequence, of the target gene are preferred for inhibition. RNA sequences with insertions, deletions, and single point mutations relative to the target sequence have also been found to be effective for inhibition. Greater than 90% sequence identity, or even 100% sequence identity, between the inhibitory RNA and the portion of the target gene is preferred. In certain preferred embodiments, the length of the duplex-forming portion of an shRNA is at least 20, 21 or 22 nucleotides in length, e.g., corresponding in size to RNA products produced by Dicer-dependent cleavage. In certain embodiments, the shRNA construct is at least 25, 50, 100, 200, 300 or 400 bases in length. In certain embodiments, the shRNA construct is 400-800 bases in length. shRNA constructs are highly tolerant of variation in loop sequence and loop size.\

As used herein, the term "ribozyme" refers to a catalytically active RNA molecule capable of site-specific cleavage of target mRNA. Several subtypes have been described, e.g., hammerhead and hairpin ribozymes. Ribozyme catalytic activity and stability can be improved by substituting deoxyribonucleotides for ribonucleotides at noncatalytic bases. While ribozymes that cleave mRNA at site-specific recognition sequences can be used to destroy particular mRNAs, the use of hammerhead ribozymes is preferred. Hammerhead ribozymes cleave mRNAs at locations dictated by flanking regions that form complementary base pairs with the target mRNA. The sole requirement is that the target mRNA has the following sequence of two bases: 5'-UG-3'. The construction and production of hammerhead ribozymes is well known in the art.

A preferred method of delivery of a polynucleotide-of-interest that comprises an siRNA, an miRNA, an shRNA, or a ribozyme comprises one or more regulatory sequences, such as, for example, a strong constitutive pol III, e.g., human U6 snRNA promoter, the mouse U6 snRNA promoter, the human and mouse H1 RNA promoter and the human tRNA-val promoter, or a strong constitutive pol II promoter, as described elsewhere herein.

The polynucleotides contemplated herein, regardless of the length of the coding sequence itself, may be combined with other DNA sequences, such as promoters and/or enhancers, untranslated regions (UTRs), signal sequences, Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, and polynucleotides encoding self-cleaving polypeptides, epitope tags, as disclosed elsewhere herein or as known in the art, such that their overall length may vary considerably. It is therefore contemplated that a polynucleotide fragment of almost any length may be employed, with the total length preferably being limited by the ease of preparation and use in the intended recombinant DNA protocol.

Polynucleotides can be prepared, manipulated, expressed and/or delivered using any of a variety of well-established techniques known and available in the art. In order to express a desired polypeptide, a nucleotide sequence encoding the polypeptide, can be inserted into appropriate vector.

Illustrative examples of vectors include, but are not limited to plasmid, autonomously replicating sequences, and transposable elements, e.g., Sleeping Beauty, PiggyBac.

Additional Illustrative examples of vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses.

Illustrative examples of viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40).

Illustrative examples of expression vectors include, but are not limited to pCIneo vectors (Promega) for expression in mammalian cells; pLenti4/V5-DEST™, pLenti6/V5-DEST™, and pLenti6.2/V5-GW/lacZ (Invitrogen) for lentivirus-mediated gene transfer and expression in mammalian cells. In particular embodiments, coding sequences of polypeptides disclosed herein can be ligated into such expression vectors for the expression of the polypeptides in mammalian cells.

In particular embodiments, the vector is an episomal vector or a vector that is maintained extrachromosomally. As used herein, the term "episomal" refers to a vector that is able to replicate without integration into host's chromosomal DNA and without gradual loss from a dividing host cell also meaning that said vector replicates extrachromosomally or episomally. The vector is engineered to harbor the sequence coding for the origin of DNA replication or "ori" from an alpha, beta, or gamma herpesvirus, an adenovirus, SV40, a bovine papilloma virus, or a yeast. Typically, the host cell comprises the viral replication transactivator protein that activates the replication. Alpha herpesviruses have a relatively short reproductive cycle, variable host range, efficiently destroy infected cells and establish latent infections primarily in sensory ganglia. Illustrative examples of alpha herpes viruses include HSV 1, HSV 2, and VZV. Beta herpesviruses have long reproductive cycles and a restricted host range. Infected cells often enlarge. Latency can be maintained in the white cells of the blood, kidneys, secretory glands and other tissues. Illustrative examples of beta herpes viruses include CMV, HHV-6 and HHV-7. Gamma-herpesviruses are specific for either T or B lymphocytes, and latency is often demonstrated in lymphoid tissue. Illustrative examples of gamma herpes viruses include EBV and HHV-8.

"Expression control sequences," "control elements," or "regulatory sequences" present in an expression vector are those non-translated regions of the vector—origin of replication, selection cassettes, promoters, enhancers, translation initiation signals (Shine Dalgamo sequence or Kozak sequence) introns, a polyadenylation sequence, 5' and 3' untranslated regions—which interact with host cellular proteins to carry out transcription and translation. Such elements may vary in their strength and specificity. Depending on the vector system and host utilized, any number of suitable transcription and translation elements, including ubiquitous promoters and inducible promoters may be used.

In particular embodiments, a polynucleotide is a vector, including but not limited to expression vectors and viral vectors, and includes exogenous, endogenous, or heterologous control sequences such as promoters and/or enhancers. An "endogenous control sequence" is one which is naturally linked with a given gene in the genome. An "exogenous control sequence" is one which is placed in juxtaposition to a gene by means of genetic manipulation (i.e., molecular biological techniques) such that transcription of that gene is directed by the linked enhancer/promoter. A "heterologous control sequence" is an exogenous sequence that is from a different species than the cell being genetically manipulated.

The term "promoter" as used herein refers to a recognition site of a polynucleotide (DNA or RNA) to which an RNA polymerase binds. An RNA polymerase initiates and transcribes polynucleotides operably linked to the promoter. In particular embodiments, promoters operative in mammalian cells comprise an AT-rich region located approximately 25 to 30 bases upstream from the site where transcription is initiated and/or another sequence found 70 to 80 bases upstream from the start of transcription, a CNCAAT region where N may be any nucleotide.

The term "enhancer" refers to a segment of DNA which contains sequences capable of providing enhanced transcription and in some instances can function independent of their orientation relative to another control sequence. An enhancer can function cooperatively or additively with promoters and/or other enhancer elements. The term "promoter/enhancer" refers to a segment of DNA which contains sequences capable of providing both promoter and enhancer functions.

The term "operably linked", refers to a juxtaposition wherein the components described are in a relationship permitting them to function in their intended manner. In one embodiment, the term refers to a functional linkage between a nucleic acid expression control sequence (such as a promoter, and/or enhancer) and a second polynucleotide sequence, e.g., a polynucleotide-of-interest, wherein the expression control sequence directs transcription of the nucleic acid corresponding to the second sequence.

As used herein, the term "constitutive expression control sequence" refers to a promoter, enhancer, or promoter/enhancer that continually or continuously allows for transcription of an operably linked sequence. A constitutive expression control sequence may be a "ubiquitous" promoter, enhancer, or promoter/enhancer that allows expression in a wide variety of cell and tissue types or a "cell specific," "cell type specific," "cell lineage specific," or "tissue specific" promoter, enhancer, or promoter/enhancer that allows expression in a restricted variety of cell and tissue types, respectively.

Illustrative ubiquitous expression control sequences suitable for use in particular embodiments include, but are not limited to, a cytomegalovirus (CMV) immediate early promoter, a viral simian virus 40 (SV40) (e.g., early or late), a Moloney murine leukemia virus (MoMLV) LTR promoter, a Rous sarcoma virus (RSV) LTR, a herpes simplex virus (HSV) (thymidine kinase) promoter, H5, P7.5, and P11 promoters from vaccinia virus, an elongation factor 1-alpha (EF1a) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus (Irions et al., *Nature Biotechnology* 25, 1477-1482 (2007)), a Ubiquitin C promoter (UBC), a phosphoglycerate kinase-1 (PGK) promoter, a cytomegalovirus enhancer/chicken β-actin (CAG) promoter, a β-actin promoter and a myeloproliferative sarcoma virus enhancer, negative control region deleted, d1587rev primer-binding site substituted (MND) promoter (Challita et al., *J Virol.* 69(2):748-55 (1995)).

In one embodiment, a vector comprises an MND promoter.

In one embodiment, a vector comprises an EF1a promoter comprising the first intron of the human EF a gene.

In one embodiment, a vector comprises an EF1a promoter that lacks the first intron of the human EF1a gene.

In a particular embodiment, it may be desirable to use a cell, cell type, cell lineage or tissue specific expression control sequence to achieve cell type specific, lineage specific, or tissue specific expression of a desired polynucleotide sequence (e.g., to express a particular nucleic acid encoding a polypeptide in only a subset of cell types, cell lineages, or tissues or during specific stages of development).

In a particular embodiment, it may be desirable to express a polynucleotide a T cell specific promoter.

As used herein, "conditional expression" may refer to any type of conditional expression including, but not limited to, inducible expression; repressible expression; expression in cells or tissues having a particular physiological, biological, or disease state, etc. This definition is not intended to exclude cell type or tissue specific expression. Certain embodiments provide conditional expression of a polynucleotide-of-interest, e.g., expression is controlled by subjecting a cell, tissue, organism, etc., to a treatment or condition that causes the polynucleotide to be expressed or that causes an increase or decrease in expression of the polynucleotide encoded by the polynucleotide-of-interest.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, Gene, 323:67), the cumate inducible gene switch (WO 2002/088346), tetracycline-dependent regulatory systems, etc.

Inducer agents include, but are not limited to glucocorticoids, estrogens, mifepristone (RU486), metals, interferons, small molecules, cumate, tetracycline, doxycycline, and variants thereof.

Conditional expression can also be achieved by using a site specific DNA recombinase. According to certain embodiments the vector comprises at least one (typically two) site(s) for recombination mediated by a site specific recombinase. As used herein, the terms "recombinase" or "site specific recombinase" include excisive or integrative proteins, enzymes, co-factors or associated proteins that are involved in recombination reactions involving one or more recombination sites (e.g., two, three, four, five, seven, ten, twelve, fifteen, twenty, thirty, fifty, etc.), which may be wild-type proteins (see Landy, Current Opinion in Biotechnology 3:699-707 (1993)), or mutants, derivatives (e.g., fusion proteins containing the recombination protein sequences or fragments thereof), fragments, and variants thereof. Illustrative examples of recombinases suitable for use in particular embodiments include, but are not limited to: Cre, Int, IHF, Xis, Flp, Fis, Hin, Gin, ΦC31, Cin, Tn3 resolvase, TndX, XerC, XerD, TnpX, Hjc, Gin, SpCCE1, and ParA.

The polynucleotides may comprise one or more recombination sites for any of a wide variety of site specific recombinases. It is to be understood that the target site for a site specific recombinase is in addition to any site(s) required for integration of a vector, e.g., a retroviral vector or lentiviral vector. As used herein, the terms "recombination sequence," "recombination site," or "site specific recombination site" refer to a particular nucleic acid sequence to which a recombinase recognizes and binds.

For example, one recombination site for Cre recombinase is loxP which is a 34 base pair sequence comprising two 13 base pair inverted repeats (serving as the recombinase binding sites) flanking an 8 base pair core sequence (see FIG. 1 of Sauer, B., Current Opinion in Biotechnology 5:521-527 (1994)). Other exemplary loxP sites include, but are not limited to: lox511 (Hoess et al., 1996; Bethke and Sauer, 1997), lox5171 (Lee and Saito, 1998), lox2272 (Lee and Saito, 1998), m2 (Langer et al., 2002), lox71 (Albert et al., 1995), and lox66 (Albert et al., 1995).

Suitable recognition sites for the FLP recombinase include, but are not limited to: FRT (McLeod, et al., 1996), $F_1$, $F_2$, $F_3$ (Schlake and Bode, 1994), $F_4$, $F_5$ (Schlake and Bode, 1994), FRT(LE) (Senecoff et al., 1988), FRT(RE) (Senecoff et al., 1988).

Other examples of recognition sequences are the attB, attP, attL, and attR sequences, which are recognized by the recombinase enzyme λ Integrase, e.g., phi-c31. The φC31 SSR mediates recombination only between the heterotypic sites attB (34 bp in length) and attP (39 bp in length) (Groth et al., 2000). attB and attP, named for the attachment sites for the phage integrase on the bacterial and phage genomes, respectively, both contain imperfect inverted repeats that are likely bound by φC31 homodimers (Groth et al., 2000). The product sites, attL and attR, are effectively inert to further φC31-mediated recombination (Belteki et al., 2003), making the reaction irreversible. For catalyzing insertions, it has been found that attB-bearing DNA inserts into a genomic attP site more readily than an attP site into a genomic attB site (Thyagarajan et al., 2001; Belteki et al., 2003). Thus, typical strategies position by homologous recombination an attP-bearing "docking site" into a defined locus, which is then partnered with an attB-bearing incoming sequence for insertion.

As used herein, an "internal ribosome entry site" or "IRES" refers to an element that promotes direct internal ribosome entry to the initiation codon, such as ATG, of a cistron (a protein encoding region), thereby leading to the cap-independent translation of the gene. See, e.g., Jackson et al., 1990. Trends Biochem Sci 15(12):477-83) and Jackson and Kaminski. 1995. RNA 1(10):985-1000. Examples of IRES generally employed by those of skill in the art include those described in U.S. Pat. No. 6,692,736. Further examples of "IRES" known in the art include, but are not limited to IRES obtainable from picornavirus (Jackson et al., 1990) and IRES obtainable from viral or cellular mRNA sources, such as for example, immunoglobulin heavy-chain binding protein (BiP), the vascular endothelial growth factor (VEGF) (Huez et al. 1998. Mol. Cell. Biol. 18(11):6178-6190), the fibroblast growth factor 2 (FGF-2), and insulin-like growth factor (IGFII), the translational initiation factor eIF4G and yeast transcription factors TFIID and HAP4, the encephelomyocarditis virus (EMCV) which is commercially available from Novagen (Duke et al., 1992. J. Virol 66(3): 1602-9) and the VEGF IRES (Huez et al., 1998. Mol Cell Biol 18(11):6178-90). IRES have also been reported in viral genomes of Picornaviridae, Dicistroviridae and Flaviviridae species and in HCV, Friend murine leukemia virus (FrMLV) and Moloney murine leukemia virus (MoMLV).

In one embodiment, the IRES used in polynucleotides contemplated herein is an EMCV IRES.

In particular embodiments, the polynucleotides comprise polynucleotides that have a consensus Kozak sequence and that encode a desired polypeptide. As used herein, the term "Kozak sequence" refers to a short nucleotide sequence that greatly facilitates the initial binding of mRNA to the small subunit of the ribosome and increases translation. The consensus Kozak sequence is (GCC)RCCATGG (SEQ ID NO:43), where R is a purine (A or G) (Kozak, 1986. Cell. 44(2):283-92, and Kozak, 1987. Nucleic Acids Res. 15(20): 8125-48).

Elements directing the efficient termination and polyadenylation of the heterologous nucleic acid transcripts increases heterologous gene expression. Transcription termination signals are generally found downstream of the polyadenylation signal. In particular embodiments, vectors comprise a polyadenylation sequence 3' of a polynucleotide encoding a polypeptide to be expressed. The term "polyA site" or "polyA sequence" as used herein denotes a DNA sequence which directs both the termination and polyadenylation of the nascent RNA transcript by RNA polymerase II. Polyadenylation sequences can promote mRNA stability by addition of a polyA tail to the 3' end of the coding sequence and thus, contribute to increased translational efficiency. Efficient polyadenylation of the recombinant transcript is desirable as transcripts lacking a polyA tail are unstable and are rapidly degraded. Illustrative examples of polyA signals that can be used in a vector, includes an ideal polyA sequence (e.g., AATAAA, ATTAAA, AGTAAA), a bovine growth hormone polyA sequence (BGHpA), a rabbit β-globin polyA sequence (rβgpA), or another suitable heterologous or endogenous polyA sequence known in the art.

In some embodiments, a polynucleotide or cell harboring the polynucleotide utilizes a suicide gene, including an inducible suicide gene to reduce the risk of direct toxicity and/or uncontrolled proliferation. In specific embodiments, the suicide gene is not immunogenic to the host harboring the polynucleotide or cell. A certain example of a suicide gene that may be used is caspase-9 or caspase-8 or cytosine deaminase. Caspase-9 can be activated using a specific chemical inducer of dimerization (CID).

In certain embodiments, polynucleotides comprise gene segments that cause the immune effector cells, e.g., T cells, to be susceptible to negative selection in vivo. By "negative selection" is meant that the infused cell can be eliminated as a result of a change in the in vivo condition of the individual. The negative selectable phenotype may result from the insertion of a gene that confers sensitivity to an administered agent, for example, a compound. Negative selectable genes are known in the art, and include, inter alia the following: the Herpes simplex virus type I thymidine kinase (HSV-I TK) gene (Wigler et al., *Cell* 11:223, 1977) which confers ganciclovir sensitivity; the cellular hypoxanthine phosphribosyltransferase (HPRT) gene, the cellular adenine phosphoribosyltransferase (APRT) gene, and bacterial cytosine deaminase, (Mullen et al., *Proc. Natl. Acad. Sci. USA.* 89:33 (1992)).

In some embodiments, genetically modified immune effector cells, such as T cells, comprise a polynucleotide further comprising a positive marker that enables the selection of cells of the negative selectable phenotype in vitro. The positive selectable marker may be a gene which, upon being introduced into the host cell expresses a dominant phenotype permitting positive selection of cells carrying the gene. Genes of this type are known in the art, and include, inter alia, hygromycin-B phosphotransferase gene (hph) which confers resistance to hygromycin B, the amino glycoside phosphotransferase gene (neo or aph) from Tn5 which codes for resistance to the antibiotic G418, the dihydrofolate reductase (DHFR) gene, the adenosine deaminase gene (ADA), and the multi-drug resistance (MDR) gene.

In one embodiment, the positive selectable marker and the negative selectable element are linked such that loss of the negative selectable element necessarily also is accompanied by loss of the positive selectable marker. In a particular embodiment, the positive and negative selectable markers are fused so that loss of one obligatorily leads to loss of the other. An example of a fused polynucleotide that yields as an expression product a polypeptide that confers both the desired positive and negative selection features described above is a hygromycin phosphotransferase thymidine kinase fusion gene (HyTK). Expression of this gene yields a polypeptide that confers hygromycin B resistance for positive selection in vitro, and ganciclovir sensitivity for negative selection in vivo. See also the publications of PCT US91/08442 and PCT/US94/05601, by S. D. Lupton, describing the use of bifunctional selectable fusion genes derived from fusing a dominant positive selectable markers with negative selectable markers.

Preferred positive selectable markers are derived from genes selected from the group consisting of hph, nco, and gpt, and preferred negative selectable markers are derived from genes selected from the group consisting of cytosine deaminase, HSV-I TK, VZV TK, HPRT, APRT and gpt. Exemplary bifunctional selectable fusion genes contemplated in particular embodiments include, but are not limited to genes wherein the positive selectable marker is derived from hph or neo, and the negative selectable marker is derived from cytosine deaminase or a TK gene or selectable marker.

In particular embodiments, polynucleotides encoding one or more salvage CARs, dimerizable salvage receptors, therapeutic polypeptides, or fusion polypeptides may be introduced into immune effector cells, e.g., T cells, by both non-viral and viral methods. In particular embodiments, delivery of one or more polynucleotides may be provided by the same method or by different methods, and/or by the same vector or by different vectors.

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. In particular embodiments, non-viral vectors are used to deliver one or more polynucleotides contemplated herein to a T cell.

Illustrative examples of non-viral vectors include, but are not limited to plasmids (e.g., DNA plasmids or RNA plasmids), transposons, cosmids, bacterial artificial chromosomes, and viral vectors.

Illustrative methods of non-viral delivery of polynucleotides contemplated in particular embodiments include, but are not limited to: electroporation, sonoporation, lipofection, microinjection, biolistics, virosomes, liposomes, immunoliposomes, nanoparticles, polycation or lipid:nucleic acid conjugates, naked DNA, artificial virions, DEAE-dextran-mediated transfer, gene gun, and heat-shock.

Illustrative examples of polynucleotide delivery systems suitable for use in particular embodiments contemplated in particular embodiments include, but are not limited to those provided by Amaxa Biosystems, Maxcyte, Inc., BTX Molecular Delivery Systems, and Copernicus Therapeutics Inc. Lipofection reagents are sold commercially (e.g., Transfectam™ and Lipofectin™). Cationic and neutral lipids that are suitable for efficient receptor-recognition lipofection of polynucleotides have been described in the literature. See e.g., Liu et al. (2003) *Gene Therapy.* 10:180-187; and Balazs et al. (2011) *Journal of Drug Delivery.* 2011:1-12. Antibody-targeted, bacterially derived, non-living nanocell-based delivery is also contemplated in particular embodiments.

Viral vectors comprising polynucleotides contemplated in particular embodiments can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., mobilized peripheral blood, lymphocytes, bone marrow aspirates, tissue biopsy, etc.) or universal donor hematopoietic stem cells, followed by reimplantation of the cells into a patient.

In one embodiment, viral vectors comprising polynucleotides contemplated herein are administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Illustrative examples of viral vector systems suitable for use in particular embodiments contemplated in particular embodiments include, but are not limited to adeno-associated virus (AAV), retrovirus, herpes simplex virus, adenovirus, vaccinia virus vectors for gene transfer.

In various embodiments, one or more polynucleotides are introduced into an immune effector cell, e.g., T cell, by transducing the cell with a recombinant adeno-associated virus (rAAV), comprising the one or more polynucleotides.

AAV is a small (~26 nm) replication-defective, primarily episomal, non-enveloped virus. AAV can infect both dividing and non-dividing cells and may incorporate its genome into that of the host cell. Recombinant AAV (rAAV) are typically composed of, at a minimum, a transgene and its regulatory sequences, and 5' and 3' AAV inverted terminal repeats (ITRs). The ITR sequences are about 145 bp in length. In particular embodiments, the rAAV comprises ITRs and capsid sequences isolated from AAV1, AAV2, AAV3, AAV4, AAV5, AAV6, AAV7, AAV8, AAV9, or AAV10.

In some embodiments, a chimeric rAAV is used the ITR sequences are isolated from one AAV serotype and the capsid sequences are isolated from a different AAV serotype. For example, a rAAV with ITR sequences derived from AAV2 and capsid sequences derived from AAV6 is referred to as AAV2/AAV6. In particular embodiments, the rAAV vector may comprise ITRs from AAV2, and capsid proteins from any one of AAV1, AAV2, AAV3, AAV4, AAV5, AAV6, AAV7, AAV8, AAV9, or AAV10. In a preferred embodiment, the rAAV comprises ITR sequences derived from AAV2 and capsid sequences derived from AAV6.

In some embodiments, engineering and selection methods can be applied to AAV capsids to make them more likely to transduce cells of interest.

Construction of rAAV vectors, production, and purification thereof have been disclosed, e.g., in U.S. Pat. Nos. 9,169,494; 9,169,492; 9,012,224; 8,889,641; 8,809,058; and 8,784,799, each of which is incorporated by reference herein, in its entirety.

In various embodiments, one or more polynucleotides are introduced into an immune effector cell, e.g., T cell, by transducing the cell with a retrovirus, e.g., lentivirus, comprising the one or more polynucleotides.

As used herein, the term "retrovirus" refers to an RNA virus that reverse transcribes its genomic RNA into a linear double-stranded DNA copy and subsequently covalently integrates its genomic DNA into a host genome. Illustrative retroviruses suitable for use in particular embodiments, include, but are not limited to: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) and lentivirus.

As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In one embodiment, HIV based vector backbones (i.e., HIV cis-acting sequence elements) are preferred.

In various embodiments, a lentiviral vector contemplated herein comprises one or more LTRs, and one or more, or all, of the following accessory elements: a cPPT/FLAP, a Psi (Ψ) packaging signal, an export element, poly (A) sequences, and may optionally comprise a WPRE or HPRE, an insulator element, a selectable marker, and a cell suicide gene, as discussed elsewhere herein.

In particular embodiments, lentiviral vectors contemplated herein may be integrative or non-integrating or integration defective lentivirus. As used herein, the term "integration defective lentivirus" or "IDLV" refers to a lentivirus having an integrase that lacks the capacity to integrate the viral genome into the genome of the host cells. Integration-incompetent viral vectors have been described in patent application WO 2006/010834, which is herein incorporated by reference in its entirety.

Illustrative mutations in the HIV-1 pol gene suitable to reduce integrase activity include, but are not limited to: H12N, H12C, H16C, H16V, S81R, D41A, K42A, H51A, Q53C, D55V, D64E, D64V, E69A, K71A, E85A, E87A, D116N, D1161, D116A, N120G, N1201, N120E, E152G, E152A, D35E, K156E, K156A, E157A, K159E, K159A, K160A, R166A, D167A, E170A, H171A, K173A, K186Q, K186T, K188T, E198A, R199c, R199T, R199A, D202A, K211A, Q214L, Q216L, Q221 L, W235F, W235E, K236S, K236A, K246A, G247W, D253A, R262A, R263A and K264H.

The term "long terminal repeat (LTR)" refers to domains of base pairs located at the ends of retroviral DNAs which, in their natural sequence context, are direct repeats and contain U3, R and U5 regions.

As used herein, the term "FLAP element" or "cPPT/FLAP" refers to a nucleic acid whose sequence includes the central polypurine tract and central termination sequences (cPPT and CTS) of a retrovirus, e.g., HIV-1 or HIV-2. Suitable FLAP elements are described in U.S. Pat. No. 6,682,907 and in Zennou, et al., 2000, *Cell*, 101:173.

As used herein, the term "packaging signal" or "packaging sequence" refers to psi [Ψ] sequences located within the retroviral genome which are required for insertion of the viral RNA into the viral capsid or particle, see e.g., Clever et al., 1995. *J. of Virology*, Vol. 69, No. 4; pp. 2101-2109.

The term "export element" refers to a cis-acting post-transcriptional regulatory element which regulates the transport of an RNA transcript from the nucleus to the cytoplasm of a cell. Examples of RNA export elements include, but are not limited to, the human immunodeficiency virus (HIV) rev response element (RRE) (see e.g., Cullen et al., 1991. *J*

*Virol.* 65: 1053; and Cullen et al., 1991. *Cell* 58: 423), and the hepatitis B virus post-transcriptional regulatory element (HPRE).

In particular embodiments, expression of heterologous sequences in viral vectors is increased by incorporating posttranscriptional regulatory elements, efficient polyadenylation sites, and optionally, transcription termination signals into the vectors. A variety of posttranscriptional regulatory elements can increase expression of a heterologous nucleic acid at the protein, e.g., woodchuck hepatitis virus posttranscriptional regulatory element (WPRE; Zufferey et al., 1999, *J. Virol.*, 73:2886); the posttranscriptional regulatory element present in hepatitis B virus (HPRE) (Huang et al., *Mol. Cell. Biol.*, 5:3864); and the like (Liu et al., 1995, *Genes Dev.*, 9:1766).

Lentiviral vectors preferably contain several safety enhancements as a result of modifying the LTRs. "Self-inactivating" (SIN) vectors refers to replication-defective vectors, e.g., in which the right (3') LTR enhancer-promoter region, known as the U3 region, has been modified (e.g., by deletion or substitution) to prevent viral transcription beyond the first round of viral replication. An additional safety enhancement is provided by replacing the U3 region of the 5' LTR with a heterologous promoter to drive transcription of the viral genome during production of viral particles. Examples of heterologous promoters which can be used include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters.

The terms "pseudotype" or "pseudotyping" as used herein, refer to a virus whose viral envelope proteins have been substituted with those of another virus possessing preferable characteristics. For example, HIV can be pseudotyped with vesicular stomatitis virus G-protein (VSV-G) envelope proteins, which allows HIV to infect a wider range of cells because HIV envelope proteins (encoded by the env gene) normally target the virus to $CD4^+$ presenting cells.

In certain embodiments, lentiviral vectors are produced according to known methods. See e.g., Kutner et al., *BMC Biotechnol.* 2009; 9:10. doi: 10.1186/1472-6750-9-10; Kutner et al. *Nat. Protoc.* 2009; 4(4):495-505. doi: 10.1038/nprot.2009.22.

According to certain specific embodiments contemplated herein, most or all of the viral vector backbone sequences are derived from a lentivirus, e.g., HIV-1. However, it is to be understood that many different sources of retroviral and/or lentiviral sequences can be used, or combined and numerous substitutions and alterations in certain of the lentiviral sequences may be accommodated without impairing the ability of a transfer vector to perform the functions described herein. Moreover, a variety of lentiviral vectors are known in the art, see Naldini et al., (1996a, 1996b, and 1998); Zufferey et al., (1997); Dull et al., 1998, U.S. Pat. Nos. 6,013,516; and 5,994,136, many of which may be adapted to produce a viral vector or transfer plasmid contemplated herein.

In various embodiments, one or more polynucleotides are introduced into an immune effector cell, by transducing the cell with an adenovirus comprising the one or more polynucleotides.

Adenoviral based vectors are capable of very high transduction efficiency in many cell types and do not require cell division. With such vectors, high titer and high levels of expression have been obtained. This vector can be produced in large quantities in a relatively simple system. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity.

Generation and propagation of the current adenovirus vectors, which are replication deficient, may utilize a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones & Shenk, 1978), the current adenovirus vectors, with the help of 293 cells, carry foreign DNA in either the E1, the D3 or both regions (Graham & Prevec, 1991). Adenovirus vectors have been used in eukaryotic gene expression (Levrero et al., 1991; Gomez-Foix et al., 1992) and vaccine development (Grunhaus & Horwitz, 1992; Graham & Prevec, 1992). Studies in administering recombinant adenovirus to different tissues include trachea instillation (Rosenfeld et al., 1991; Rosenfeld et al., 1992), muscle injection (Ragot et al., 1993), peripheral intravenous injections (Herz & Gerard, 1993) and stereotactic inoculation into the brain (Le Gal La Salle et al., 1993). An example of the use of an Ad vector in a clinical trial involved polynucleotide therapy for antitumor immunization with intramuscular injection (Sterman et al., *Hum. Gene Ther.* 7:1083-9 (1998)).

In various embodiments, one or more polynucleotides are introduced into an immune effector cell by transducing the cell with a herpes simplex virus, e.g., HSV-1, HSV-2, comprising the one or more polynucleotides.

The mature HSV virion consists of an enveloped icosahedral capsid with a viral genome consisting of a linear double-stranded DNA molecule that is 152 kb. In one embodiment, the HSV based viral vector is deficient in one or more essential or non-essential HSV genes. In one embodiment, the HSV based viral vector is replication deficient. Most replication deficient HSV vectors contain a deletion to remove one or more intermediate-early, early, or late HSV genes to prevent replication. For example, the HSV vector may be deficient in an immediate early gene selected from the group consisting of: ICP4, ICP22, ICP27, ICP47, and a combination thereof. Advantages of the HSV vector are its ability to enter a latent stage that can result in long-term DNA expression and its large viral DNA genome that can accommodate exogenous DNA inserts of up to 25 kb. HSV-based vectors are described in, for example, U.S. Pat. Nos. 5,837,532, 5,846,782, and 5,804,413, and International Patent Applications WO 91/02788, WO 96/04394, WO 98/15637, and WO 99/06583, each of which are incorporated by reference herein in its entirety.

H. Genetically Modified Cells

In various embodiments, cells are modified to express the salvage CARs and/or dimerizable salvage receptors contemplated herein, for use in the treatment of cancer are provided. Cells may be non-genetically modified to express the salvage CARs and/or dimerizable salvage receptors contemplated herein, or in particular preferred embodiments, cells may be genetically modified to express the salvage CARs and/or dimerizable salvage receptors contemplated herein. As used herein, the term "genetically engineered" or "genetically modified" refers to the addition of extra genetic material in the form of DNA or RNA into the total genetic material in a cell. The terms, "genetically modified cells," "modified cells," and "redirected cells," are used interchangeably in particular embodiments. As used herein, the term "gene therapy" refers to the introduction of extra genetic material in the form of DNA or RNA into the total genetic material in a cell that restores, corrects, or modifies expression of a gene, or for the purpose of expressing a salvage CAR polypeptide and/or dimerizable salvage receptor polypeptide.

In particular embodiments, the salvage CARs contemplated herein are introduced and expressed in immune effector cells so as to redirect their specificity to a target antigen of interest. In particular embodiments, salvage CARs contemplated herein are introduced and expressed in immune effector cells so as to redirect their specificity to a primary target antigen of interest and dimerizable salvage receptors are introduced and inducibly expressed so as to redirect their specificity to a secondary target antigen of interest in the presence of a bridging factor.

An "immune effector cell," is any cell of the immune system that has one or more effector functions (e.g., cytotoxic cell killing activity, secretion of cytokines, induction of ADCC and/or CDC). The illustrative immune effector cells contemplated herein are T lymphocytes, in particular cytotoxic T cells (CTLs; CD8+ T cells), TILs, and helper T cells (HTLs; CD4+ T cells). In one embodiment, immune effector cells include natural killer (NK) cells. In one embodiment, immune effector cells include natural killer T (NKT) cells. Immune effector cells can be autologous/autogeneic ("self") or non-autologous ("non-self," e.g., allogeneic, syngeneic or xenogeneic).

"Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. In preferred embodiments, the cells are autologous.

Illustrative immune effector cells used with the salvage CARs and/or dimerizable salvage receptors contemplated herein include T lymphocytes. The terms "T cell" or "T lymphocyte" are art-recognized and are intended to include thymocytes, immature T lymphocytes, mature T lymphocytes, resting T lymphocytes, or activated T lymphocytes. A T cell can be a T helper (Th) cell, for example a T helper 1 (Th1) or a T helper 2 (Th2) cell. The T cell can be a helper T cell (HTL; CD4$^+$ T cell) CD4$^+$ T cell, a cytotoxic T cell (CTL; CD8$^+$ T cell), CD4$^+$ CD8$^+$ T cell, CD4$^-$ CD8$^-$ T cell, or any other subset of T cells. Other illustrative populations of T cells suitable for use in particular embodiments include naïve T cells and memory T cells.

As would be understood by the skilled person, other cells may also be used as immune effector cells with the salvage CARs and/or dimerizable salvage receptors contemplated herein. In particular, immune effector cells also include NK cells, NKT cells, neutrophils, and macrophages. Immune effector cells also include progenitors of effector cells wherein such progenitor cells can be induced to differentiate into an immune effector cells in vivo or in vitro. Thus, in particular embodiments, immune effector cell includes progenitors of immune effectors cells such as hematopoietic stem cells (HSCs) contained within the CD34$^+$ population of cells derived from cord blood, bone marrow or mobilized peripheral blood which upon administration in a subject differentiate into mature immune effector cells, or which can be induced in vitro to differentiate into mature immune effector cells.

As used herein, immune effector cells genetically engineered to contain a specific salvage CAR may be referred to as, "antigen specific redirected immune effector cells."

The term, "CD34$^+$ cell," as used herein refers to a cell expressing the CD34 protein on its cell surface. "CD34," as used herein refers to a cell surface glycoprotein (e.g., sialomucin protein) that often acts as a cell-cell adhesion factor and is involved in T cell entrance into lymph nodes. The CD34$^+$ cell population contains hematopoietic stem cells (HSC), which upon administration to a patient differentiate and contribute to all hematopoietic lineages, including T cells, NK cells, NKT cells, neutrophils and cells of the monocyte/macrophage lineage.

Methods for making the immune effector cells which express a salvage CAR and/or dimerizable salvage receptor contemplated herein are provided in particular embodiments. In one embodiment, the method comprises transfecting or transducing immune effector cells isolated from an individual such that the immune effector cells express one or more salvage CARs as contemplated herein. In one embodiment, the method comprises transfecting or transducing immune effector cells isolated from an individual such that the immune effector cells express one or more salvage CARs and/or dimerizable salvage receptors contemplated herein. In certain embodiments, the immune effector cells are isolated from an individual and genetically modified without further manipulation in vitro. Such cells can then be directly re-administered into the individual. In further embodiments, the immune effector cells are first activated and stimulated to proliferate in vitro prior to being genetically modified. In this regard, the immune effector cells may be cultured before and/or after being genetically modified.

In particular embodiments, prior to in vitro manipulation or genetic modification of the immune effector cells described herein, the source of cells is obtained from a subject. In particular embodiments, the modified immune effector cells comprise T cells.

T cells can be obtained from a number of sources including, but not limited to, peripheral blood mononuclear cells, bone marrow, lymph nodes tissue, cord blood, thymus issue, tissue from a site of infection, ascites, pleural effusion, spleen tissue, and tumors. In certain embodiments, T cells can be obtained from a unit of blood collected from a subject using any number of techniques known to the skilled person, such as sedimentation, e.g., FICOLL™ separation.

In other embodiments, an isolated or purified population of T cells is used. In some embodiments, after isolation of PBMC, both cytotoxic and helper T lymphocytes can be sorted into naïve, memory, and effector T cell subpopulations either before or after activation, expansion, and/or genetic modification.

A specific subpopulation of T cells, expressing one or more of the following markers: CD3, CD4, CD8, CD28, CD45RA, CD45RO, CD62, CD127, and HLA-DR can be further isolated by positive or negative selection techniques. In one embodiment, a specific subpopulation of T cells, expressing one or more of the markers selected from the group consisting of CD62L, CCR7, CD28, CD27, CD122, CD127, CD197; or CD38 or CD62L, CD127, CD197, and CD38, is further isolated by positive or negative selection techniques. In various embodiments, the manufactured T cell compositions do not express or do not substantially express one or more of the following markers: CD57, CD244, CD160, PD-1, CTLA4, TIM3, and LAG3.

In one embodiment, an isolated or purified population of T cells expresses one or more of the markers including, but not limited to a CD3+, CD4+, CD8+, or a combination thereof.

In certain embodiments, the T cells are isolated from an individual and first activated and stimulated to proliferate in vitro prior to being modified to express a salvage CAR and/or dimerizable salvage receptor.

In order to achieve sufficient therapeutic doses of T cell compositions, T cells are often subjected to one or more rounds of stimulation, activation and/or expansion. T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; and 6,867,041, each of which is incorporated herein by reference in its entirety. In particular embodiments, T cells are activated and expanded for about 6 hours, about 12 hours, about 18 hours or about 24 hours prior to introduction of vectors or mRNAs encoding the salvage CARs and/or dimerizable salvage receptors contemplated herein.

In one embodiment, T cells are activated at the same time that they are modified.

In various embodiments, a method of generating a CAR T cell comprises activating a population of cells comprising T cells and expanding the population of T cells. T cell activation can be accomplished by providing a primary stimulation signal through the T cell TCR/CD3 complex and by providing a secondary costimulation signal through an accessory molecule, e.g., CD28.

The TCR/CD3 complex may be stimulated by contacting the T cell with a suitable CD3 binding agent, e.g., a CD3 ligand or an anti-CD3 monoclonal antibody. Illustrative examples of CD3 antibodies include, but are not limited to, OKT3, G19-4, BC3, and 64.1.

In addition to the primary stimulation signal provided through the TCR/CD3 complex, induction of T cell responses requires a second, costimulatory signal. In particular embodiments, a CD28 binding agent can be used to provide a costimulatory signal. Illustrative examples of CD28 binding agents include but are not limited to: natural CD 28 ligands, e.g., a natural ligand for CD28 (e.g., a member of the B7 family of proteins, such as B7-1(CD80) and B7-2 (CD86); and anti-CD28 monoclonal antibody or fragment thereof capable of crosslinking the CD28 molecule, e.g., monoclonal antibodies 9.3, B-T3, XR-CD28, KOLT-2, 15E8, 248.23.2, and EX5.3D10.

In one embodiment, the molecule providing the primary stimulation signal, for example a molecule which provides stimulation through the TCR/CD3 complex and the costimulatory molecule are coupled to the same surface.

In certain embodiments, binding agents that provide stimulatory and costimulatory signals are localized on the surface of a cell. This can be accomplished by transfecting or transducing a cell with a nucleic acid encoding the binding agent in a form suitable for its expression on the cell surface or alternatively by coupling a binding agent to the cell surface.

In another embodiment, the molecule providing the primary stimulation signal, for example a molecule which provides stimulation through the TCR/CD3 complex and the costimulatory molecule are displayed on antigen presenting cells.

In one embodiment, the molecule providing the primary stimulation signal, for example a molecule which provides stimulation through the TCR/CD3 complex and the costimulatory molecule are provided on separate surfaces.

In a certain embodiment, one of the binding agents that provides stimulatory and costimulatory signals is soluble (provided in solution) and the other agent(s) is provided on one or more surfaces.

In a particular embodiment, the binding agents that provide stimulatory and costimulatory signals are both provided in a soluble form (provided in solution).

In various embodiments, the methods for making salvage CAR T cells contemplated herein comprise activating T cells with anti-CD3 and anti-CD28 antibodies.

In one embodiment, expanding T cells activated by the methods contemplated herein further comprises culturing a population of cells comprising T cells for several hours (about 3 hours) to about 7 days to about 28 days or any hourly integer value in between. In another embodiment, the T cell composition may be cultured for 14 days. In a particular embodiment, T cells are cultured for about 21 days. In another embodiment, the T cell compositions are cultured for about 2-3 days. Several cycles of stimulation/activation/expansion may also be desired such that culture time of T cells can be 60 days or more.

In particular embodiments, conditions appropriate for T cell culture include an appropriate media (e.g., Minimal Essential Media or RPMI Media 1640 or, X-vivo 15, (Lonza)) and one or more factors necessary for proliferation and viability including, but not limited to serum (e.g., fetal bovine or human serum), interleukin-2 (IL-2), insulin, IFN-γ, IL-4, IL-7, IL-21, GM-CSF, IL-10, IL-12, IL-15, TGFβ, and TNF-α or any other additives suitable for the growth of cells known to the skilled artisan.

Further illustrative examples of cell culture media include, but are not limited to RPMI 1640, Clicks, AIM-V, DMEM, MEM, a-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells.

Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% C02).

In particular embodiments, PBMCs or isolated T cells are contacted with a stimulatory agent and costimulatory agent, such as anti-CD3 and anti-CD28 antibodies, generally attached to a bead or other surface, in a culture medium with appropriate cytokines, such as IL-2, IL-7, and/or IL-15.

In other embodiments, artificial APC (aAPC) made by engineering K562, U937, 721.221, T2, and C1R cells to direct the stable expression and secretion, of a variety of costimulatory molecules and cytokines. In a particular embodiment K32 or U32 aAPCs are used to direct the display of one or more antibody-based stimulatory molecules on the AAPC cell surface. Populations of T cells can be expanded by aAPCs expressing a variety of costimulatory molecules including, but not limited to, CD137L (4-1BBL), CD134L (OX40L), and/or CD80 or CD86. Finally, the aAPCs provide an efficient platform to expand genetically modified T cells and to maintain CD28 expression on CD8 T cells. aAPCs provided in WO 03/057171 and US2003/0147869 are hereby incorporated by reference in their entirety.

In a particular embodiment, polynucleotide encoding a salvage CAR and/or dimerizable salvage receptor are introduced into the population of T cells. The polynucleotides may be introduced into the T cells by microinjection, transfection, lipofection, heat-shock, electroporation, transduction, gene gun, microinjection, DEAE-dextran-mediated transfer, and the like.

In various embodiments, a salvage CAR T cell is generated. In some embodiments, the salvage CAR T cell is further genetically modified by introducing a nucleic acid comprising an inducible promoter operably linked to a polynucleotide encoding a dimerizable salvage receptor.

In a preferred embodiment, polynucleotides are introduced into a T cell by viral transduction.

Illustrative examples of viral vector systems suitable for introducing a polynucleotide into an immune effector cell or CD34$^+$ cell include, but are not limited to adeno-associated virus (AAV), retrovirus, herpes simplex virus, adenovirus, vaccinia virus vectors for gene transfer.

In one embodiment, polynucleotides are introduced into a T cell by AAV transduction.

In one embodiment, polynucleotides are introduced into a T cell by retroviral transduction.

In one embodiment, polynucleotides are introduced into a T cell by lentiviral transduction.

In one embodiment, polynucleotides are introduced into a T cell by adenovirus transduction.

In one embodiment, polynucleotides are introduced into a T cell by herpes simplex virus transduction.

In one embodiment, polynucleotides are introduced into a T cell by vaccinia virus transduction.

In various embodiments, genetically modified cells contemplated herein further comprise one or more modified TCRα alleles. In particular embodiments, one or more engineered nucleases designed to create a double strand break at the TCRα locus are introduced into salvage CAR T cells. In particular embodiments, one or more engineered nucleases designed to create a double strand break at the TCRα locus are introduced into salvage CAR T cells comprising a nucleic acid comprising an inducible promoter operably linked to a polynucleotide encoding a dimerizable salvage receptor.

In particular embodiments, methods of generating genetically modified T cells comprises contacting the cells with a stimulatory agent and costimulatory agent, such as soluble anti-CD3 and anti-CD28 antibodies, or antibodies attached to a bead or other surface, in a culture medium with appropriate cytokines, such as IL-2, IL-7, and/or IL-15 and/or one or more agents that modulate a PI3K cell signaling pathway.

As used herein, the term "PI3K inhibitor" refers to a nucleic acid, peptide, compound, or small organic molecule that binds to and inhibits at least one activity of PI3K. The PI3K proteins can be divided into three classes, class 1 PI3Ks, class 2 PI3Ks, and class 3 PI3Ks. Class 1 PI3Ks exist as heterodimers consisting of one of four p110 catalytic subunits (p110α, p110β, p110δ, and p110γ) and one of two families of regulatory subunits. In particular embodiments, a PI3K inhibitor targets the class 1 PI3K inhibitors. In one embodiment, a PI3K inhibitor will display selectivity for one or more isoforms of the class 1 PI3K inhibitors (i.e., selectivity for p110α, p110β, p110δ, and p110γ or one or more of p110α, p110β, p110δ, and p110γ). In another aspect, a PI3K inhibitor will not display isoform selectivity and be considered a "pan-PI3K inhibitor." In one embodiment, a PI3K inhibitor will compete for binding with ATP to the PI3K catalytic domain.

Illustrative examples of PI3K inhibitors suitable for use particular embodiments include, but are not limited to, BKM120 (class 1 PI3K inhibitor, Novartis), XL147 (class 1 PI3K inhibitor, Exelixis), (pan-PI3K inhibitor, GlaxoSmithKline), and PX-866 (class 1 PI3K inhibitor; p110α, p110β, and p110γ isoforms, Oncothyreon).

Other illustrative examples of selective PI3K inhibitors include, but are not limited to BYL719, GSK2636771, TGX-221, AS25242, CAL-101, ZSTK474, and IPI-145.

Further illustrative examples of pan-PI3K inhibitors include, but are not limited to BEZ235, LY294002, GSK1059615, TG100713, and GDC-0941.

In a preferred embodiment, the PI3K inhibitor is ZSTK474.

I. Compositions and Formulations

The compositions contemplated herein may comprise one or more polypeptides, polynucleotides, vectors comprising same, genetically modified immune effector cells, etc. Compositions include, but are not limited to pharmaceutical compositions. A "pharmaceutical composition" refers to a composition formulated in pharmaceutically-acceptable or physiologically-acceptable solutions for administration to a cell or an animal, either alone, or in combination with one or more other modalities of therapy. It will also be understood that, if desired, the compositions may be administered in combination with other agents as well, such as, e.g., cytokines, growth factors, hormones, small molecules, chemotherapeutics, pro-drugs, drugs, antibodies, or other various pharmaceutically-active agents. There is virtually no limit to other components that may also be included in the compositions, provided that the additional agents do not adversely affect the ability of the composition to deliver the intended therapy.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein "pharmaceutically acceptable carrier" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier which has been approved by the United States Food and Drug Administration as being acceptable for use in humans or domestic animals. Exemplary pharmaceutically acceptable carriers include, but are not limited to, to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and any other compatible substances employed in pharmaceutical formulations.

In particular embodiments, compositions comprise an amount of salvage CAR-expressing immune effector cells contemplated herein. In other particular embodiments, compositions comprise an amount of dimerizable salvage receptor. In other particular embodiments, compositions comprise an amount of bridging factor. In other particular embodiments, compositions comprise an amount of dimerizable salvage receptor bound to a bridging factor.

As used herein, the term "amount" refers to "an amount effective" or "an effective amount" of a therapeutic cell, a salvage CAR T cell, a dimerizable salvage receptor, or bridging factor, etc., to achieve a beneficial or desired prophylactic or therapeutic result, including clinical results.

A "prophylactically effective amount" refers to an amount of a therapeutic cell, a salvage CAR T cell, a dimerizable salvage receptor, or bridging factor, etc., effective to achieve the desired prophylactic result. Typically but not necessarily, since a prophylactic dose is used in subjects prior to or at an earlier stage of disease, the prophylactically effective amount is less than the therapeutically effective amount.

A "therapeutically effective amount" of a therapeutic cell, a salvage CAR T cell, a dimerizable salvage receptor, or bridging factor, etc., may vary according to factors such as the disease state, age, sex, and weight of the individual, and the ability of the composition to elicit a desired response in the individual. A therapeutically effective amount is also one in which any toxic or detrimental effects of a therapeutic cell, a salvage CAR T cell, a dimerizable salvage receptor, or bridging factor, etc., are outweighed by the therapeutically beneficial effects. The term "therapeutically effective amount" includes an amount that is effective to "treat" a subject (e.g., a patient). When a therapeutic amount is indicated, the precise amount of the compositions to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^2$ to $10^{10}$ cells/kg body weight, preferably $10^5$ to $10^6$ cells/kg body weight, including all integer values within those ranges. The number of cells will depend upon the ultimate use for which the composition is intended as will the type of cells included therein. For uses provided herein, the cells are generally in a volume of a liter or less, can be 500 mLs or less, even 250 mLs or 100 mLs or less. Hence the density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells. In some embodiments, particularly since all the infused cells will be redirected to a particular target antigen, lower numbers of cells, in the range of $10^6$/kilogram ($10^6$-$10^{11}$ per patient) may be administered. T cell compositions that comprise T cells that express salvage CARs may be administered multiple times at dosages within these ranges. The cells may be allogeneic, syngeneic, xenogeneic, or autologous to the patient undergoing therapy. If desired, the treatment may also include administration of mitogens (e.g., PHA) or lymphokines, cytokines, and/or chemokines (e.g., IFN-γ, IL-2, IL-12, TNF-alpha, IL-18, and TNF-beta, GM-CSF, IL-4, IL-13, Flt3-L, RANTES, MIP1α, etc.) as described herein to enhance induction of the immune response.

Generally, compositions comprising the cells activated and expanded as described herein may be utilized in the treatment and prevention of diseases that arise in individuals who are immunocompromised. In particular, compositions contemplated herein are used in the treatment of cancer. In particular embodiments, salvage CAR-modified T cells, dimerizable salvage receptors, and bridging factors may be administered either alone, or as a pharmaceutical compositions in combination with carriers, diluents, excipients, and/or with other components such as IL-2 or other cytokines or cell populations.

In particular embodiments, pharmaceutical compositions comprise an amount of genetically modified T cells, in combination with one or more pharmaceutically or physiologically acceptable carriers, diluents or excipients.

In particular embodiments, pharmaceutical compositions comprise an amount of dimerizable salvage receptor, in combination with one or more pharmaceutically or physiologically acceptable carriers, diluents or excipients.

In particular embodiments, pharmaceutical compositions comprise an amount of bridging factor, in combination with one or more pharmaceutically or physiologically acceptable carriers, diluents or excipients.

Pharmaceutical compositions comprising a salvage CAR-expressing immune effector cell population, such as T cells, dimerizable salvage receptors, or bridging factors may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. In particular embodiments, compositions are preferably formulated for nasal, oral, enteral, or parenteral administration, e.g., intravascular (intravenous or intraarterial), intraperitoneal or intramuscular administration.

The liquid pharmaceutical compositions, whether they be solutions, suspensions or other like form, may include one or more of the following: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition is preferably sterile.

In one embodiment, the T cell compositions contemplated herein are formulated in a pharmaceutically acceptable cell culture medium. Such compositions are suitable for administration to human subjects. In particular embodiments, the pharmaceutically acceptable cell culture medium is a serum free medium.

Serum-free medium has several advantages over serum containing medium, including a simplified and better defined composition, a reduced degree of contaminants, elimination of a potential source of infectious agents, and lower cost. In various embodiments, the serum-free medium is animal-free, and may optionally be protein-free. Optionally, the medium may contain biopharmaceutically acceptable recombinant proteins. "Animal-free" medium refers to medium wherein the components are derived from non-animal sources. Recombinant proteins replace native animal proteins in animal-free medium and the nutrients are obtained from synthetic, plant or microbial sources. "Protein-free" medium, in contrast, is defined as substantially free of protein.

Illustrative examples of serum-free media used in particular compositions includes, but is not limited to QBSF-60 (Quality Biological, Inc.), StemPro-34 (Life Technologies), and X-VIVO 10.

In one preferred embodiment, compositions comprising T cells contemplated herein are formulated in a solution comprising PlasmaLyte A.

In another preferred embodiment, compositions comprising T cells contemplated herein are formulated in a solution comprising a cryopreservation medium. For example, cryopreservation media with cryopreservation agents may be used to maintain a high cell viability outcome post-thaw. Illustrative examples of cryopreservation media used in particular compositions includes, but is not limited to, CryoStor CS10, CryoStor CS5, and CryoStor CS2.

In a more preferred embodiment, compositions comprising T cells contemplated herein are formulated in a solution comprising 50:50 PlasmaLyte A to CryoStor CS10.

In a particular embodiment, compositions comprise an effective amount of salvage CAR-expressing immune effector cells, alone or in combination with one or more therapeutic agents. Thus, the salvage CAR-expressing immune effector cell compositions may be administered alone or in combination with dimerizable savage receptors, bridging factors, or other known cancer treatments, such as radiation therapy, chemotherapy, transplantation, immunotherapy, hormone therapy, photodynamic therapy, etc. The compositions may also be administered in combination with antibiotics. Such therapeutic agents may be accepted in the art as a standard treatment for a particular disease state as described herein, such as a particular cancer. Exemplary therapeutic agents contemplated include cytokines, growth factors, steroids, NSAIDs, DMARDs, anti-inflammatories, chemotherapeutics, radiotherapeutics, therapeutic antibodies, or other active and ancillary agents.

In certain embodiments, compositions comprising salvage CAR-expressing immune effector cells disclosed herein may be administered in conjunction with any number of chemotherapeutic agents. Illustrative examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; ellipitinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid derivatives such as Targretin™ (bexarotene), Panretin™ (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on cancers such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

A variety of other therapeutic agents may be used in conjunction with the compositions described herein. In one embodiment, the composition comprising salvage CAR-expressing immune effector cells is administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate.

Other exemplary NSAIDs are chosen from the group consisting of ibuprofen, naproxen, naproxen sodium, Cox-2 inhibitors such as VIOXX® (rofecoxib) and CELEBREX® (celecoxib), and sialylates. Exemplary analgesics are chosen from the group consisting of acetaminophen, oxycodone, tramadol of proporxyphene hydrochloride. Exemplary glucocorticoids are chosen from the group consisting of cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular) and minocycline.

Illustrative examples of therapeutic antibodies suitable for combination with the salvage CAR modified T cells contemplated herein, include but are not limited to, bavituximab, bevacizumab (avastin), bivatuzumab, blinatumomab, conatumumab, daratumumab, duligotumab, dacetuzumab, dalotuzumab, elotuzumab (HuLuc63), gemtuzumab, ibritumomab, indatuximab, inotuzumab, lorvotuzumab, lucatumumab, milatuzumab, moxetumomab, ocaratuzumab, ofatumumab, rituximab, siltuximab, teprotumumab, and ublituximab, either alone or as part of a dimerizable salvage receptor.

In certain embodiments, the compositions described herein are administered in conjunction with a cytokine. By "cytokine" as used herein is meant a generic term for proteins released by one cell population that act on another cell as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

J. Therapeutic Methods

The salvage CAR systems contemplated herein provide improved methods of adoptive immunotherapy for use in the prevention, treatment, and amelioration cancers, or for preventing, treating, or ameliorating at least one symptom associated with a cancer. In preferred embodiments, the salvage CAR systems contemplated herein provide improved methods of adoptive immunotherapy for use in the prevent, treatment, and amelioration of relapsed or refractory cancers.

In various embodiments, the salvage CAR systems contemplated herein provide improved methods of adoptive immunotherapy for use in increasing the cytotoxicity toward relapsed or refractory cancer cells or for use in decreasing the number of relapsed or refractory cancer cells.

In particular embodiments, the specificity of a primary T cell is redirected to tumor or cancer cells by genetically modifying the primary T cell with salvage CAR directed to a first antigen expresses on the cancer cells. In one embodiment, the salvage CAR T cells are infused to a recipient in need thereof. The infused cells are able to kill tumor cells in the recipient. Unlike antibody therapies, salvage CAR T cells are able to replicate in vivo; thus, contributing to long-term persistence that can lead to a more sustained cancer therapy. However, in cases where remission or cancer regression is incomplete and the cancer relapses or becomes refractory to treatment, a dimerizable salvage receptor is provided in the presence of a bridging factor to retarget the salvage CAR T cell therapies to a second antigen that is expressed on the relapsed or refractory cancer cells.

In one embodiment, salvage CAR T cells are administered to a subject diagnosed with cancer. Upon relapsed or refractory cancer cell growth, the subject is administered a dimerizable salvage receptor and a bridging factor to re-initiate the CAR T cell therapy toward the relapsed or refractory cells. Should the secondary tumor also relapse, either a different salvage CAR T cell, a different dimerizable salvage receptor, or both may be provided to the subject. This cycle may be repeated as many times as necessary to eradicate the cancer in the subject.

In one embodiment, salvage CAR T cells comprising an inducible dimerizable salvage receptor are administered to a subject diagnosed with cancer. Upon relapsed or refractory cancer cell growth, the subject is administered an agent that induces the expression of the dimerizable salvage receptor, and is also administered a bridging factor to re-initiate the CAR T cell therapy toward the relapsed or refractory cells. Should the secondary tumor also relapse, either a different salvage CAR T cell, a different dimerizable salvage receptor, or both may be provided to the subject. The different salvage receptor may be under the control of a different inducible promoter in the same salvage CAR T cell or provided by direct administration of the dimerizable salvage receptor polypeptide. This cycle may be repeated as many times as necessary to eradicate the cancer in the subject.

In particular embodiments, salvage CAR systems contemplated herein are used in the treatment of solid tumors or cancers.

In particular embodiments, salvage CAR systems contemplated herein are used in the treatment of solid tumors or cancers including, but not limited to: adrenal cancer, adrenocortical carcinoma, anal cancer, appendix cancer, astrocytoma, atypical teratoid/rhabdoid tumor, basal cell carcinoma, bile duct cancer, bladder cancer, bone cancer, brain/CNS cancer, breast cancer, bronchial tumors, cardiac tumors, cervical cancer, cholangiocarcinoma, chondrosarcoma, chordoma, colon cancer, colorectal cancer, craniopharyngioma, ductal carcinoma in situ (DCIS) endometrial cancer, ependymoma, esophageal cancer, esthesioneuroblastoma, Ewing's sarcoma, extracranial germ cell tumor, extragonadal germ cell tumor, eye cancer, fallopian tube cancer, fibrous histiosarcoma, fibrosarcoma, gallbladder cancer, gastric cancer, gastrointestinal carcinoid tumors, gastrointestinal stromal tumor (GIST), germ cell tumors, glioma, glioblastoma, head and neck cancer, hemangioblastoma, hepatocellular cancer, hypopharyngeal cancer, intraocular melanoma, kaposi sarcoma, kidney cancer, laryngeal cancer, leiomyosarcoma, lip cancer, liposarcoma, liver cancer, lung cancer, non-small cell lung cancer, lung carcinoid tumor, malignant mesothelioma, medullary carcinoma, medulloblastoma, menangioma, melanoma, Merkel cell carcinoma, midline tract carcinoma, mouth cancer, myxosarcoma, myelodysplastic syndrome, myeloproliferative neoplasms, nasal cavity and paranasal sinus cancer, nasopharyngeal cancer, neuroblastoma, oligodendroglioma, oral cancer, oral cavity cancer, oropharyngeal cancer, osteosarcoma, ovarian cancer, pancreatic cancer, pancreatic islet cell tumors, papillary carcinoma, paraganglioma, parathyroid cancer, penile cancer, pharyngeal cancer, pheochromocytoma, pinealoma, pituitary tumor, pleuropulmonary blastoma, primary peritoneal cancer, prostate cancer, rectal cancer, retinoblastoma, renal cell carcinoma, renal pelvis and ureter cancer, rhabdomyosarcoma, salivary gland cancer, sebaceous gland carcinoma, skin cancer, soft tissue sarcoma, squamous cell carcinoma, small cell lung cancer, small intestine cancer, stomach cancer, sweat gland carcinoma, synovioma, testicular cancer, throat cancer, thymus cancer, thyroid cancer, urethral cancer, uterine cancer, uterine sarcoma, vaginal cancer, vascular cancer, vulvar cancer, and Wilms Tumor.

In particular embodiments, salvage CAR systems contemplated herein are used in the treatment of solid tumors or cancers including, without limitation, liver cancer, pancreatic cancer, lung cancer, breast cancer, bladder cancer, brain cancer, bone cancer, thyroid cancer, kidney cancer, or skin cancer.

In particular embodiments, salvage CAR systems contemplated herein are used in the treatment of various cancers including but not limited to pancreatic, bladder, and lung.

In particular embodiments, salvage CAR systems contemplated herein are used in the treatment of liquid cancers or hematological cancers.

In particular embodiments, salvage CAR systems contemplated herein are used in the treatment of B-cell malignancies, including but not limited to: leukemias, lymphomas, and multiple myeloma.

In particular embodiments, salvage CAR systems contemplated herein are used in the treatment of liquid cancers including, but not limited to leukemias, lymphomas, and multiple myelomas: acute lymphocytic leukemia (ALL), acute myeloid leukemia (AML), myeloblastic, promyelocytic, myelomonocytic, monocytic, erythroleukemia, hairy cell leukemia (HCL), chronic lymphocytic leukemia (CLL), and chronic myeloid leukemia (CML), chronic myelomonocytic leukemia (CMML) and polycythemia vera, Hodgkin lymphoma, nodular lymphocyte-predominant Hodgkin lymphoma, Burkitt lymphoma, small lymphocytic lymphoma (SLL), diffuse large B-cell lymphoma, follicular lymphoma, immunoblastic large cell lymphoma, precursor B-lymphoblastic lymphoma, mantle cell lymphoma, marginal zone lymphoma, mycosis fungoides, anaplastic large cell lymphoma, Sezary syndrome, precursor T-lymphoblastic lymphoma, multiple myeloma, overt multiple myeloma, smoldering multiple myeloma, plasma cell leukemia, non-secretory myeloma, IgD myeloma, osteosclerotic myeloma, solitary plasmacytoma of bone, and extramedullary plasmacytoma.

In particular embodiments, a method comprises administering a therapeutically effective amount of salvage CAR T cells, to a patient in need thereof, and subsequently administering a dimerizable salvage receptor and a bridging factor to the subject in the event of relapsed or refractory cancer cell growth.

In particular embodiments, a method comprises administering a therapeutically effective amount of salvage CAR T cells, to a patient in need thereof, and subsequently administering a dimerizable salvage receptor bound to a bridging factor to the subject in the event of relapsed or refractory cancer cell growth.

In particular embodiments, a method comprises administering a therapeutically effective amount of salvage CAR T cells, to a patient in need thereof, and subsequently inducing expression of a dimerizable salvage receptor and administering a bridging factor to the subject in the event of relapsed or refractory cancer cell growth.

In certain embodiments, the cells are used in the treatment of patients at risk for developing a cancer. Thus, particular embodiments comprise the treatment or prevention or amelioration of at least one symptom of a cancer comprising administering to a patient in need thereof, a therapeutically effective amount of salvage CAR T cells, and subsequently administering a dimerizable salvage receptor and a bridging factor to the subject in the event of relapsed or refractory cancer cell growth.

In certain embodiments, the cells are used in the treatment of patients at risk for developing a cancer. Thus, particular embodiments comprise the treatment or prevention or amelioration of at least one symptom of a cancer comprising administering to a patient in need thereof, a therapeutically effective amount of salvage CAR T cells, and subsequently administering a dimerizable salvage receptor bound to a bridging factor to the subject in the event of relapsed or refractory cancer cell growth.

In particular embodiments, a method of treating a patient at risk for developing a cancer comprises administering a therapeutically effective amount of salvage CAR T cells, to a patient in need thereof, and subsequently inducing expression of a dimerizable salvage receptor and administering a bridging factor to the subject in the event of relapsed or refractory cancer cell growth.

In one embodiment, a method of treating a cancer in a subject in need thereof comprises administering an effective amount of salvage CAR T cells, and subsequently administering a dimerizable salvage receptor and a bridging factor to the subject in the event of relapsed or refractory cancer cell growth.

In one embodiment, a method of treating a cancer in a subject in need thereof comprises administering an effective amount of salvage CAR T cells, and subsequently administering a dimerizable salvage receptor bound to a bridging factor to the subject in the event of relapsed or refractory cancer cell growth.

In one embodiment, a method of treating a cancer in a subject in need thereof comprises administering an effective amount of salvage CAR T cells, to a patient in need thereof, and subsequently inducing expression of a dimerizable salvage receptor and administering a bridging factor to the subject in the event of relapsed or refractory cancer cell growth.

The quantity and frequency of administration will be determined by such factors as the condition of the patient, and the type and severity of the patient's disease, although appropriate dosages may be determined by clinical trials.

In one embodiment, the amount of immune effector cells, e.g., T cells, in the composition administered to a subject is at least $0.1 \times 10^5$ cells, at least $0.5 \times 10^5$ cells, at least $1 \times 10^5$ cells, at least $5 \times 10^5$ cells, at least $1 \times 10^6$ cells, at least $0.5 \times 10^7$ cells, at least $1 \times 10^7$ cells, at least $0.5 \times 10^8$ cells, at least $1 \times 10^8$ cells, at least $0.5 \times 10^9$ cells, at least $1 \times 10^9$ cells, at least $2 \times 10^9$ cells, at least $3 \times 10^9$ cells, at least $4 \times 10^9$ cells, at least $5 \times 10^9$ cells, or at least $1 \times 10^{10}$ cells.

In particular embodiments, about $1 \times 10^7$ T cells to about $1 \times 10^9$ T cells, about $2 \times 10^7$ T cells to about $0.9 \times 10^9$ T cells, about $3 \times 10^7$ T cells to about $0.8 \times 10^9$ T cells, about $4 \times 10^7$ T cells to about $0.7 \times 10^9$ T cells, about $5 \times 10^7$ T cells to about 0.6×10⁹ T cells, or about 5×10⁷ T cells to about 0.5×10⁹ T cells are administered to a subject.

In one embodiment, the amount of immune effector cells, e.g., T cells, in the composition administered to a subject is at least 0.1×10⁴ cells/kg of bodyweight, at least 0.5×10⁴ cells/kg of bodyweight, at least 1×10⁴ cells/kg of bodyweight, at least 5×10⁴ cells/kg of bodyweight, at least 1×10⁵ cells/kg of bodyweight, at least 0.5×10⁶ cells/kg of bodyweight, at least 1×10⁶ cells/kg of bodyweight, at least 0.5×10⁷ cells/kg of bodyweight, at least 1×10⁷ cells/kg of bodyweight, at least 0.5×10⁸ cells/kg of bodyweight, at least 1×10⁸ cells/kg of bodyweight, at least 2×10⁸ cells/kg of bodyweight, at least 3×10⁸ cells/kg of bodyweight, at least 4×10⁸ cells/kg of bodyweight, at least 5×10⁸ cells/kg of bodyweight, or at least 1×10⁹ cells/kg of bodyweight.

In particular embodiments, about 1×10⁶ T cells/kg of bodyweight to about 1×10⁸ T cells/kg of bodyweight, about 2×10⁶ T cells/kg of bodyweight to about 0.9×10⁸ T cells/kg of bodyweight, about 3×10⁶ T cells/kg of bodyweight to about 0.8×10⁸ T cells/kg of bodyweight, about 4×10⁶ T cells/kg of bodyweight to about 0.7×10⁸ T cells/kg of bodyweight, about 5×10⁶ T cells/kg of bodyweight to about 0.6×10⁸ T cells/kg of bodyweight, or about 5×10⁶ T cells/kg of bodyweight to about 0.5×10⁸ T cells/kg of bodyweight are administered to a subject.

One of ordinary skill in the art would recognize that multiple administrations of the compositions contemplated in particular embodiments may be required to effect the desired therapy. For example a composition may be administered 1, 2, 3, 4, 5, 6, 7, 8, 9, or 10 or more times over a span of 1 week, 2 weeks, 3 weeks, 1 month, 2 months, 3 months, 4 months, 5 months, 6 months, 1 year, 2 years, 5, years, 10 years, or more.

In certain embodiments, it may be desirable to administer activated T cells to a subject and then subsequently redraw blood (or have an apheresis performed), activate T cells therefrom, and reinfuse the patient with these activated and expanded T cells. This process can be carried out multiple times every few weeks. In certain embodiments, T cells can be activated from blood draws of from 10cc to 400cc. In certain embodiments, T cells are activated from blood draws of 20cc, 30cc, 40cc, 50cc, 60cc, 70cc, 80cc, 90cc, 100cc, 150cc, 200cc, 250cc, 300cc, 350cc, or 400cc or more. Not to be bound by theory, using this multiple blood draw/multiple reinfusion protocol may serve to select out certain populations of T cells.

The administration of the compositions contemplated in particular embodiments may be carried out in any convenient manner, including by aerosol inhalation, injection, ingestion, transfusion, implantation or transplantation. In a preferred embodiment, compositions are administered nasally, orally, enterally, or parenterally. The phrases "parenteral administration" and "administered parenterally" as used herein refers to modes of administration other than enteral and topical administration, usually by injection, and includes, without limitation, intravascular, intravenous, intramuscular, intraarterial, intrathecal, intracapsular, intraorbital, intratumoral, intracardiac, intradermal, intraperitoneal, transtracheal, subcutaneous, subcuticular, intraarticular, subcapsular, subarachnoid, intraspinal and intrasternal injection and infusion. In one embodiment, the compositions contemplated herein are administered to a subject by direct injection into a tumor, lymph node, or site of infection.

In one embodiment, a subject in need thereof is administered an effective amount of a composition to increase a cellular immune response to a cancer in the subject. The immune response may include cellular immune responses mediated by cytotoxic T cells capable of killing infected cells, regulatory T cells, and helper T cell responses. Humoral immune responses, mediated primarily by helper T cells capable of activating B cells thus leading to antibody production, may also be induced. A variety of techniques may be used for analyzing the type of immune responses induced by the compositions, which are well described in the art; e.g., Current Protocols in Immunology, Edited by: John E. Coligan, Ada M. Kruisbeek, David H. Margulies, Ethan M. Shevach, Warren Strober (2001) John Wiley & Sons, NY, N.Y.

In one embodiment, a method of treating a subject diagnosed with a cancer, comprises removing immune effector cells from the subject, modifying the immune effector cells and producing a population of modified immune effector cells, and administering the population of modified immune effector cells to the same subject. In a preferred embodiment, the immune effector cells comprise T cells.

The methods for administering the cell compositions contemplated in particular embodiments include any method which is effective to result in reintroduction of ex vivo modified immune effector cells or on reintroduction of the progenitors of immune effector cells that on introduction into a subject differentiate into mature immune effector cells. One method comprises modifying peripheral blood T cells ex vivo and returning the modified cells into the subject.

All publications, patent applications, and issued patents cited in this specification are herein incorporated by reference as if each individual publication, patent application, or issued patent were specifically and individually indicated to be incorporated by reference.

Although the foregoing embodiments have been described in some detail by way of illustration and example for purposes of clarity of understanding, it will be readily apparent to one of ordinary skill in the art in light of the teachings contemplated herein that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

Salvage Car System

A functional salvage CAR system re-directed an anti-BCMA salvage CAR to a CD19 positive, BCMA negative Nalm-6 cell line using a dimerizable anti-CD19 salvage receptor and the bridging factor AP21967.

The control anti-BCMA CAR comprises a CD8α-derived signal peptide, an anti-BCMA scFv, a CD8α derived hinge region and transmembrane domain, an intracellular 4-1BB co-stimulatory domain, and a CD3ζ signaling domain (FIG. 1, left panel, SEQ ID NO. 1). The anti-BCMA salvage CAR comprises a CD8α-derived signal peptide, an anti-BCMA scFv, a G4S linker sequence, a FRB variant (T82L), a CD8α derived hinge region and transmembrane domain, an intracellular 4-1BB co-stimulatory domain, and a CD3 zeta signaling domain (FIG. 1, center panel, SEQ ID NO. 2). The dimerizable salvage receptor comprises an IgK-derived signal peptide, a FLAG tag, an anti-CD19 scFv and a FKBP12 domain (SEQ ID NO: 3). The polypeptide used in this experiment was a polyprotein that also contained a T2A.1 sequence and an mCherry fluorescent protein (SEQ ID NO: 4). All constructs were cloned into lentiviral vectors; lentivirus was prepared using established protocols. See e.g., Kutner et al., *BMC Biotechnol.* 2009; 9:10. doi: 10.1186/1472-6750-9-10; Kutner et al. *Nat. Protoc.* 2009; 4(4):495-505. doi: 10.1038/nprot.2009.22.

Presence of a Dimerization Domain does not Impact CAR Function

Human PBMCs ($1\times10^6$ cells/mL) were activated with soluble anti-CD3 and anti-CD28 antibodies (50 ng/ml) on day 0. After 24 hr incubation, $1\times10^6$ cells were transduced with lentivirus encoding either an anti-BCMA CAR or an anti-BCMA salvage CAR. The transduced cells were washed and resuspended at $0.3\times10^6$ cells/mL growth medium on day 3. The CAR T cells were cultured for 7 days with IL-2 (250 IU/mL) containing medium changed every other day.

Figure 2A:
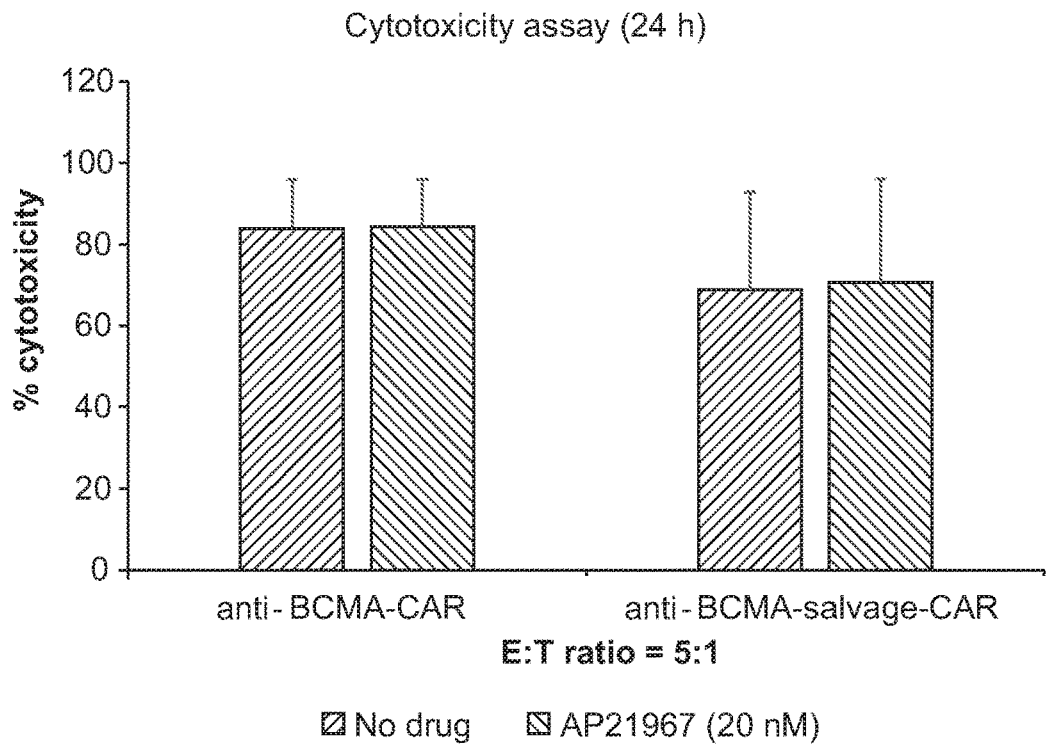
FIG. 2A shows the results from a cytotoxicity assay. Anti-BCMA CAR T cells and anti-BCMA salvage CAR T cells were co-cultured with K562-BCMA(+) and K562-BCMA(−) cells for 24 hours at an E:T ratio of 5:1. The co-cultures were treated with vehicle or AP21967.

The cytotoxic potential of anti-BCMA CAR T cells and anti-BCMA salvage CAR T cells was analyzed by co-culturing day 10 CAR T cells (E, effector cells) with a 50:50 mixture of K562-BCMA positive cells (GFP positive) (T, target cells) and K562-BCMA negative cells (BFP positive) for 24 hours at an E:T ratio of 5:1. Cells were co-cultured with or without 20 nM AP21967 (a non-immunosuppressive rapamycin analog). The ratio of K562-BCMA positive cells to K562-BCMA negative cells is a direct readout of CAR T cell cytotoxicity. There was no significant difference in BCMA specific cytotoxicity between anti-BCMA CAR T cells and anti-BCMA salvage CAR T cells (FIG. 2A). AP21967 also had no effect on cytotoxicity.

Figure 2B:
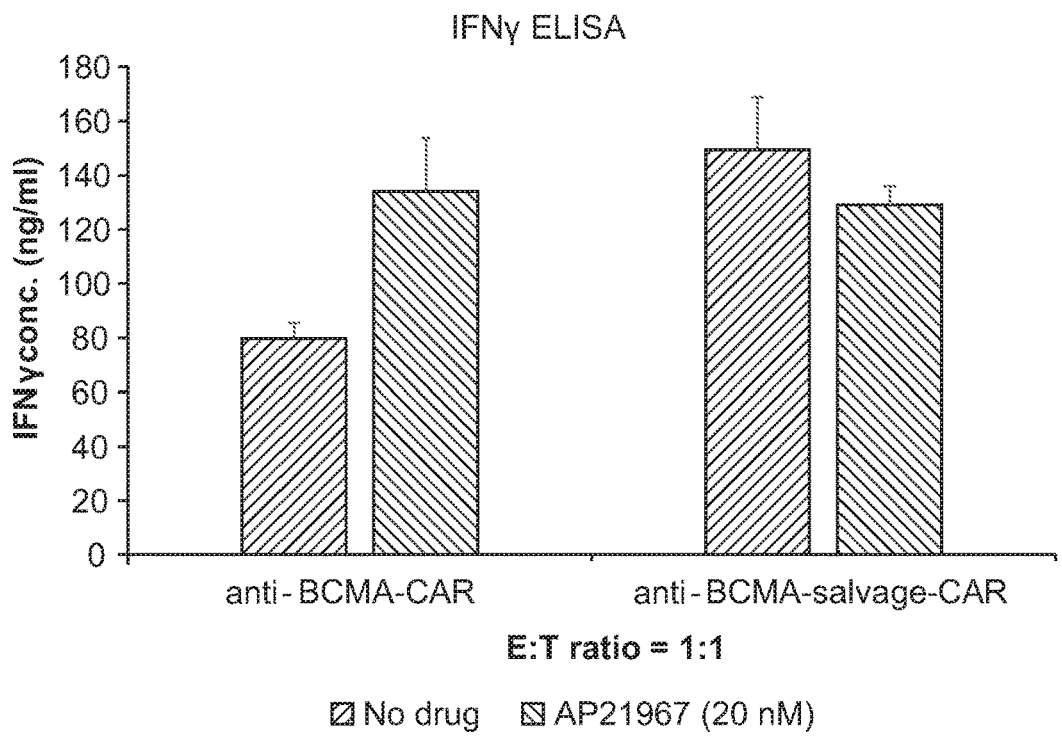
FIG. 2B shows the results from an interferon gamma (IFNγ) release assay. Anti-BCMA CAR T cells and anti-BCMA salvage CAR T cells were co-cultured with K562 BCMA(+) cells for 24 hours at an E:T ratio of 1:1. The co-cultures were treated with vehicle or AP21967.

Antigen dependent cytokine secretion was analyzed by co-culturing day 10 CAR T cells with K562-BCMA positive cells for 24 hours at an E:T ratio of 1:1 (with or without AP21967). Culture supernatants were collected and IFNγ production was analyzed using the IFNγ ELISA kit (eBiosciences). Similar levels of IFNγ secretion were observed between anti-BCMA CAR T cells and anti-BCMA salvage CAR T cells (FIG. 2B). AP21967 did not substantially affect cytotoxicity.

Anti-BCMA Salvage CAR T Cells can be Redirected to CD19 Expressing Nalm-6 Cells in the Presence of Anti-CD19 Salvage Receptor and AP21967

293 T cells were transduced with lentivirus encoding the dimerizable anti-CD19 salvage receptor to generate a stable source of secreted anti-CD19-scFv-FKBP12 proteins (FIG. 1, right panel). Supernatant containing soluble anti-CD19 salvage receptor polypeptides (anti-CD19 scFV FKBP12) was collected from stable 293T-710 cells and filtered.

Figure 3A:
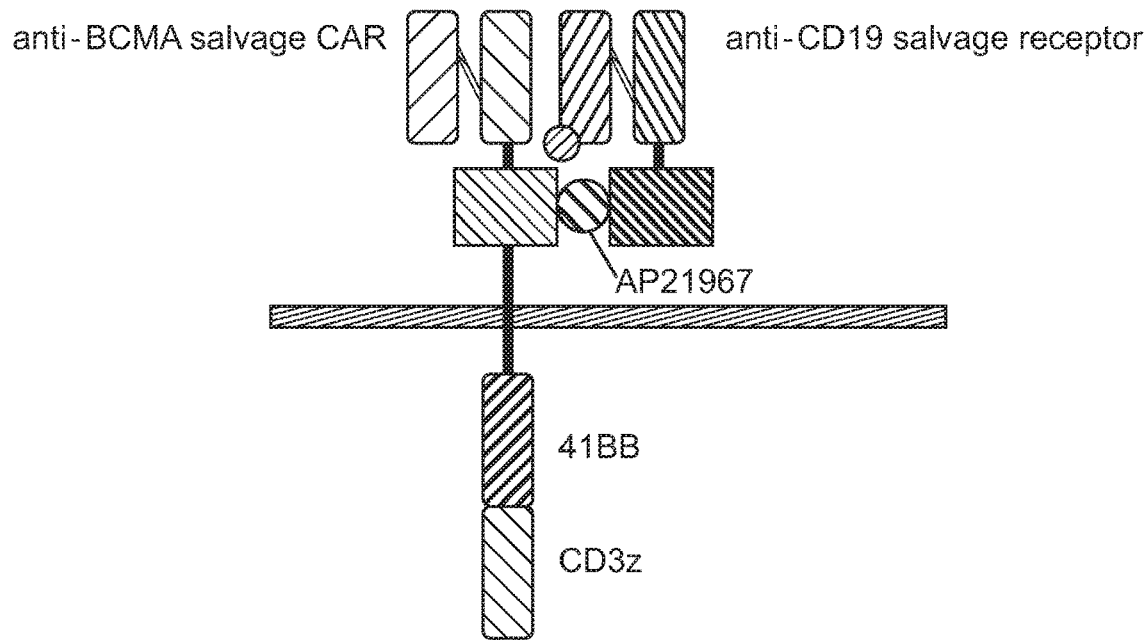
FIG. 3A shows a cartoon of a salvage CAR system. An anti-BCMA salvage CAR and a dimerizable anti-CD19 salvage receptor hetero dimerize in the presence of the bridging factor AP21967.
Figure 3B:
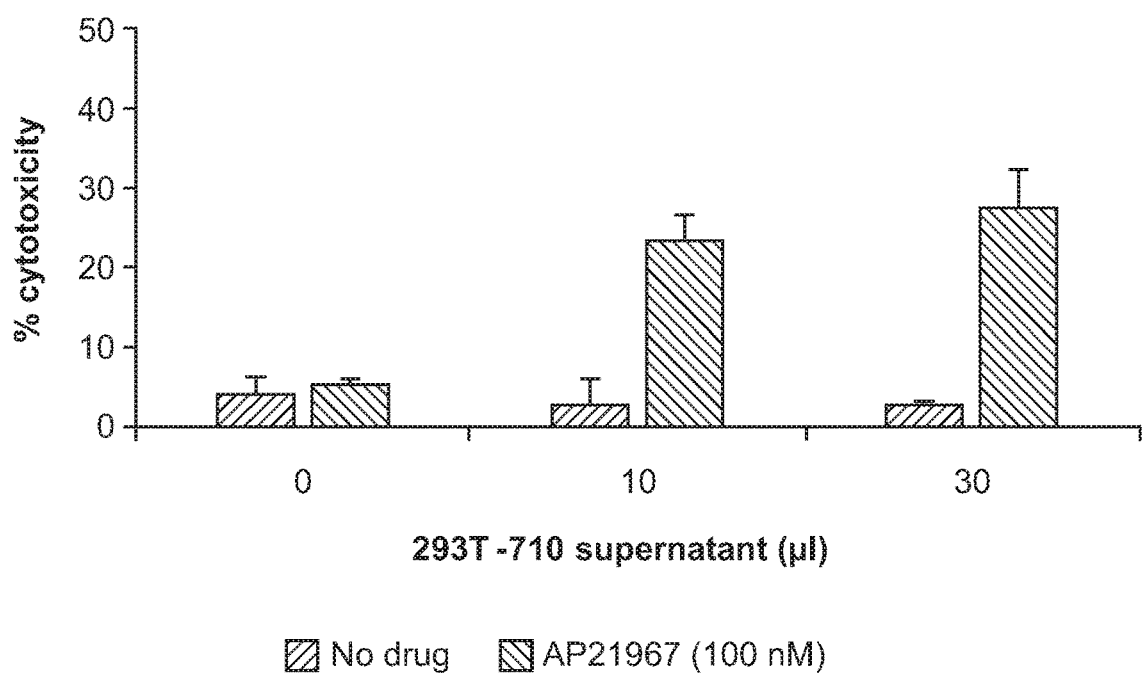
FIG. 3B shows the results from a cytotoxicity assay. Anti-BCMA salvage CAR T cells were co-cultured with Nalm-6-CD19(+) cells and K562 CD19(−) cells for 24 hours at an E:T ratio of 2:1. The co-cultures were treated with vehicle or 100 nM AP21967 and with 0 μL, 10 μL, or 30 μL of 293T-710 cell supernatant containing the dimerizable anti-CD19 salvage receptor.

The anti-CD19 salvage receptor forms a heterodimer with the anti-BCMA salvage CAR in the presence of AP21967 (FIG. 3A). The cytotoxic potential of anti-BCMA salvage CAR T cells (E) against BCMA negative, CD19 positive Nalm-6 cells (T) was analyzed by co-culturing CAR T cells with a 50:50 mixture of Nalm-6-CD19 positive cells (GFP positive) and K562-CD19 negative cells (BFP positive) for 24 hours at an E:T ratio of 2:1. The co-cultures were treated with vehicle or 100 nM AP21967 and with different volumes of 293T-710 cell supernatant (0 μl, 10 μl, or 30 μl). The anti-BCMA salvage CAR T cells showed CD19 specific cytotoxicity against Nalm-6 cells in the presence of both AP21967 and 293T-710 cell supernatant. FIG. 3B.

Figure 3C:
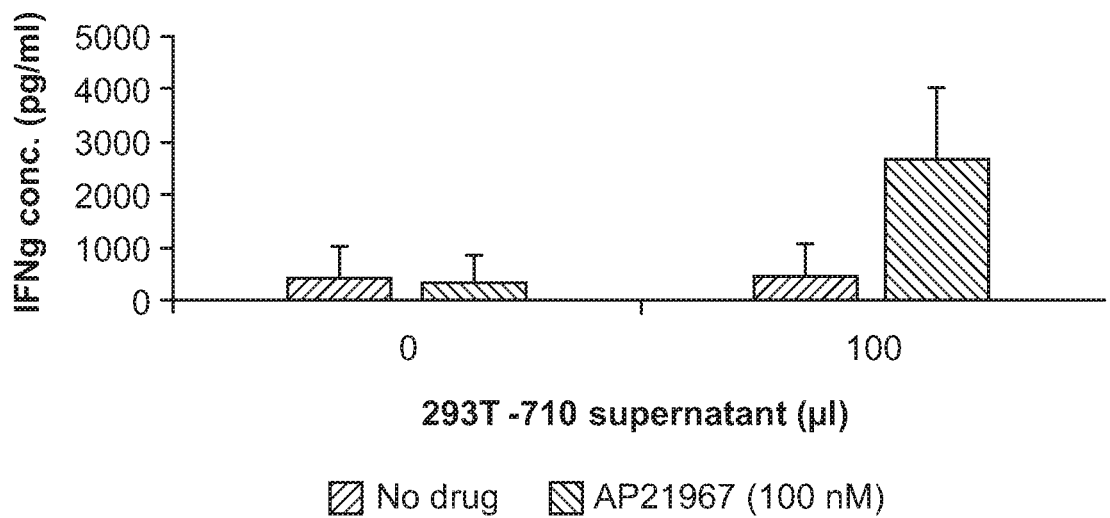
FIG. 3C shows the results from an interferon gamma (IFNγ) release assay. Anti-BCMA salvage CAR T cells were co-cultured with Nalm-6-CD19(+) cells for 24 hours at an E:T ratio of 1:1. The co-cultures were treated with 100 nM AP21967 and 0 μL or 100 μL of 293T-710 cell supernatant containing the dimerizable anti-CD19 salvage receptor.

Antigen dependent cytokine secretion was analyzed by co-culturing anti-BCMA salvage CAR T cells with CD19 positive Nalm-6 cells for 24 hours at an E:T ratio of 1:1. Co-cultures were treated with vehicle or 100 μL of of 293T-710 cell supernatant and with 100 nM AP21967. Culture supernatants were collected and IFNγ secretion was analyzed using the IFNγ ELISA kit (eBiosciences). IFNγ secretion significantly increased in anti-BCMA salvage CAR co-cultures in the presence of 100 μL 293T-710 cell supernatant and 100 nM AP21967. FIG. 3C.

Example 2

Pre-Loaded Dimerizable Anti-CD19 Salvage Receptor

A lentivirus encoding a dimerizable anti-CD19 salvage receptor comprising a human lipocalin-2-derived signal peptide, a scFV targeting CD19 antigen, a FKBP12 domain, a T2A.1 sequence, a mCherry sequence and a woodchuck post-transcriptional regulatory region (WPRE) (SEQ ID NO: 5) was used to generate a stable 293T cell line (293T-707) expressing the dimerizable anti-CD19 salvage receptor.

Figure 4A:
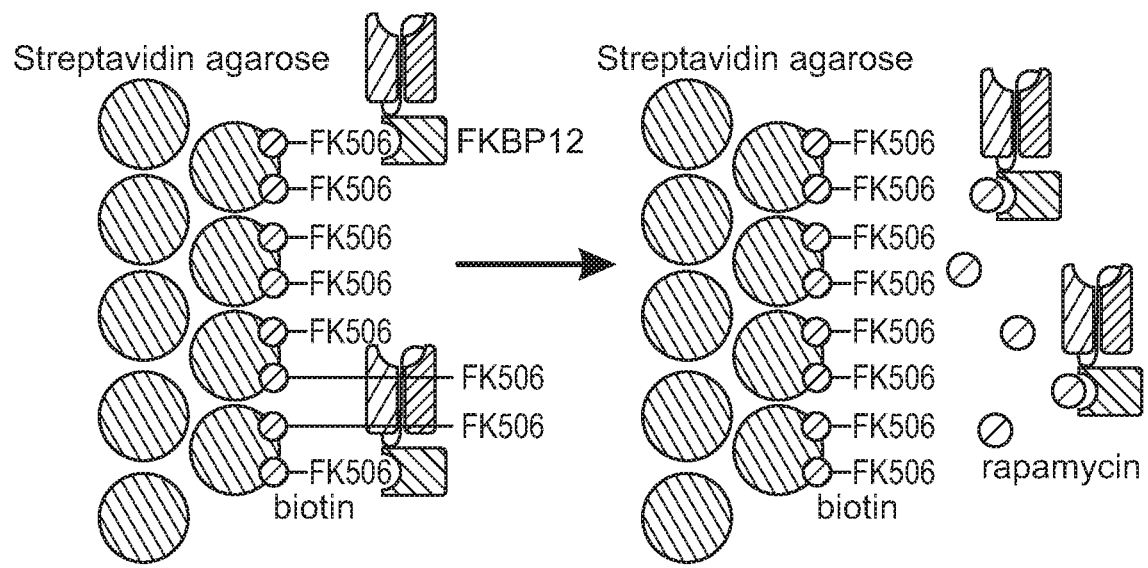
FIG. 4A shows a purification scheme for a dimerizable anti-CD19 salvage receptor.

The dimerizable anti-CD19 salvage receptor was purified by collecting and filtering (0.22 μm filter) 500 mL 293T-707 cell culture supernatant and binding to an FKBP12-specific affinity column. The column was generated by incubating 2 mL NeutrAvidin Agarose (Thermofisher) with 400 μg biotin-FK506 for 30 min at room temperature with constant rotation. The column was washed with PBS to remove uncoupled biotin-FK506. Filtered 293T-707 supernatants were passed through the column by gravity. The column was washed with PBS until the A280 of the flow through was approximately 0. Dimerizable anti-CD19 salvage receptors were eluted with 5 mL of 8 μM rapamycin followed by 15 mL PBS (FIG. 4A). Eluted proteins were concentrated (100×) using VivaSpin-20 centrifugal concentrator (10 kD MWCO). The concentrated protein fraction was re-diluted in 20 mL PBS followed by an additional round of VivaSpin-20 concentration. The protein fraction was desalted with Zeba Spin 7K column (Thermofisher) to PBS to remove residual unbound rapamycin. The purified protein solution was filter (0.22 μm) sterilized and stored at 4° C. The purified dimerizable anti-CD19 salvage receptor was assayed for the presence of bound rapamycin using SDS PAGE and Western blot analysis with rabbit anti-FKBP12 antibodies.

Figure 4B:
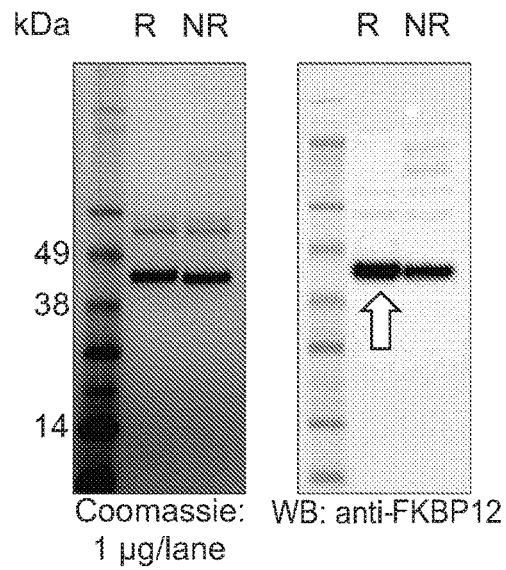
FIG. 4B shows that the purified dimerizable anti-CD19 salvage receptor is pre-loaded with ligand.

These assays confirmed that the purified dimerizable anti-CD19 salvage receptor was bound to rapamycin (FIG. 4B).

Example 3

Figure 5:
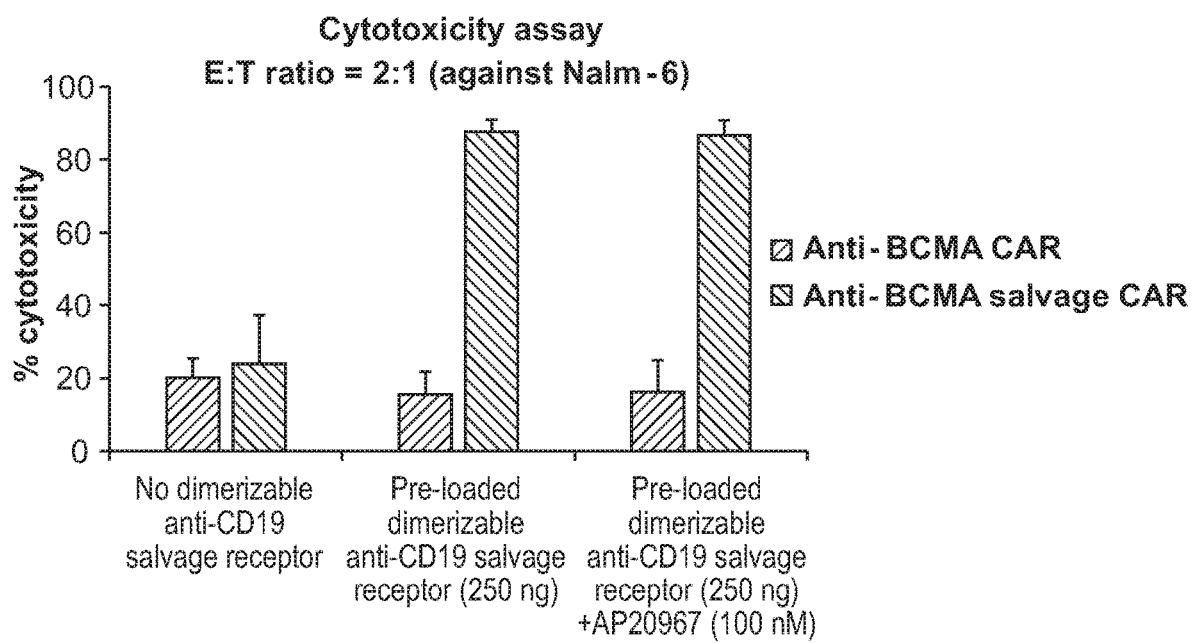
FIG. 5 shows results from a cytotoxicity assay. Anti-BCMA CAR T cells or anti-BCMA salvage CAR T cells were co-cultured with Nalm-6-CD19(+) cells and K562 CD19(−) cells, in the presence or absence of 250 ng pre-loaded dimerizable anti-CD19 salvage receptor, with or without 100 nM AP21967, for 24 hr, at a 2:1 E:T ratio.

Pre-Loaded Dimerizable Anti-CD19 Salvage Receptor Redirects Anti-BCMA Salvage Car T cells were transduced with lentiviral vectors encoding an anti-BCMA CAR or anti-BCMA salvage CAR. The CART cells were co-cultured with a 50:50 mixture of CD19 positive Nalm-6 cells expressing GFP and CD19 negative K562 cells expressing BFP, in the presence or absence of 250 ng pre-loaded dimerizable anti-CD19 salvage receptor, with or without 100 nM AP21967, for 24 hr, at a 2:1 E:T ratio. Anti-BCMA salvage CAR T cells showed CD19 specific cytotoxicity against Nalm-6 in the presence of the dimerizable anti-CD19 salvage receptor pre-loaded with rapamycin. FIG. 5. AP21967 was not required to trigger the CD19 specific cytotoxicity.

Figure 6:
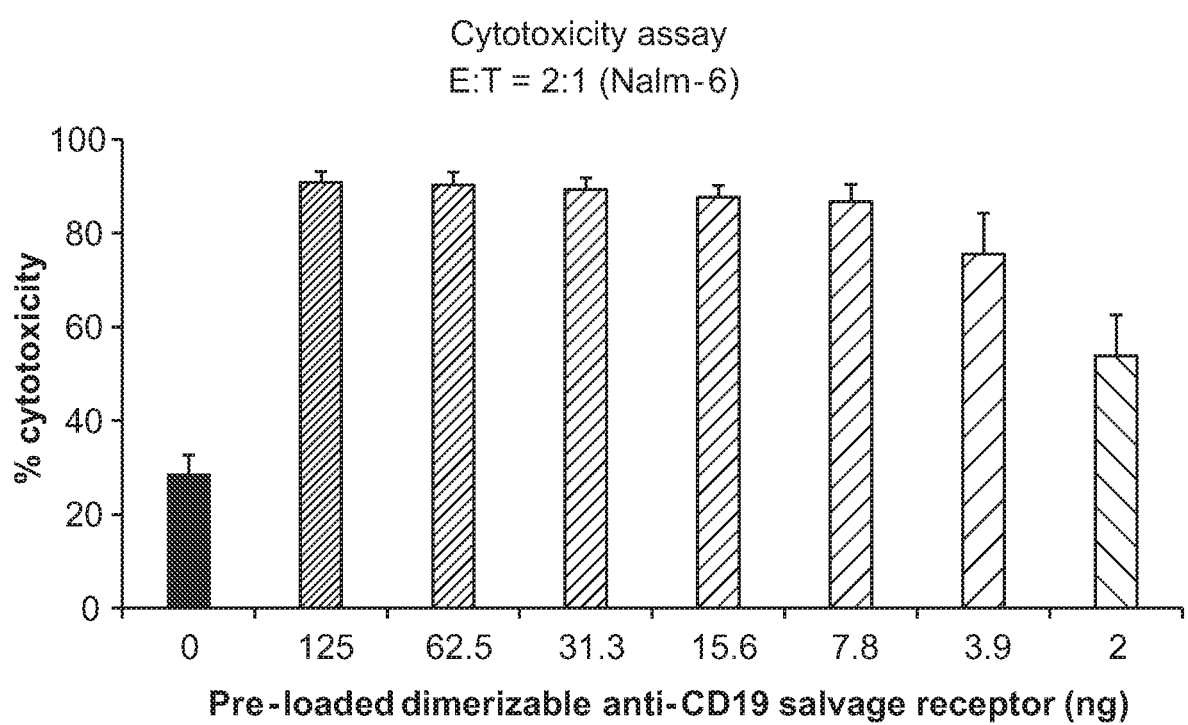
FIG. 6 shows results from a titration assay of pre-loaded dimerizable anti-CD19 salvage receptor. Anti-BCMA salvage CART cells were co-cultured with Nalm-6-CD19(+) cells and K562 CD19(−) cells, with decreasing amounts (125 ng, 62.5 ng, 31.3 ng, 15.6 ng, 7.8 ng, 3.9 ng, 2.0 ng) of pre-loaded dimerizable anti-CD19 salvage receptor for 24 hr, at a 2:1 E:T ratio.

Anti-BCMA salvage CAR T cells were co-cultured with a 50:50 mixture of CD19 positive Nalm-6 cells expressing GFP and CD19 negative K562 cells expressing BFP, with decreasing amounts (125 ng, 62.5 ng, 31.3 ng, 15.6 ng, 7.8 ng, 3.9 ng, 2.0 ng) of pre-loaded dimerizable anti-CD19 salvage receptor for 24 hr, at a 2:1 E:T ratio. At little as 2 ng of pre-loaded dimerizable anti-CD19 salvage receptor was sufficient to induce the CD19 specific cytotoxicity. FIG. 6.

Figure 7:
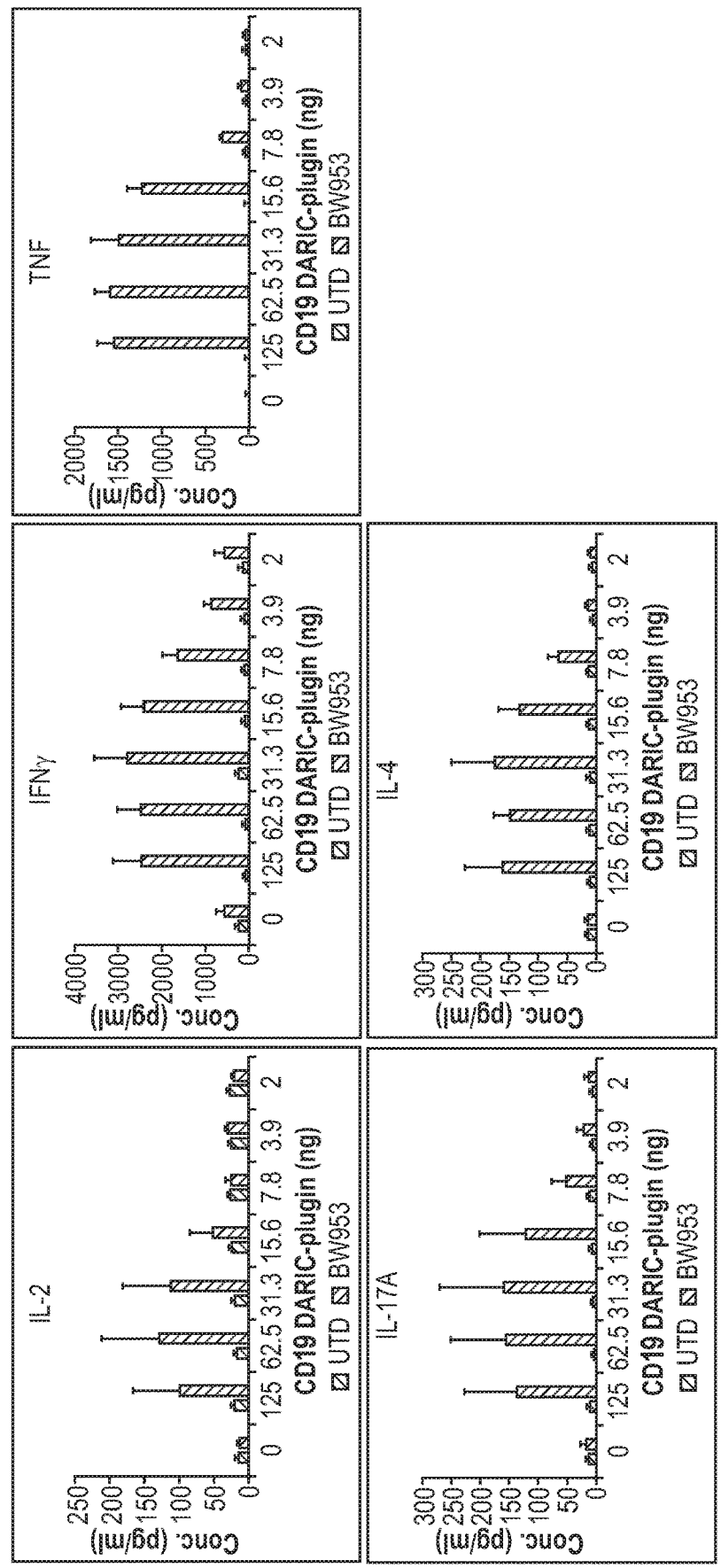
FIG. 7 shows the results from a cytokine release assay. Anti-BCMA salvage CAR T cells or untransduced T cells were co-cultured with CD19 positive Nalm-6 cells, with decreasing amounts (125 ng, 62.5 ng, 31.3 ng, 15.6 ng, 7.8 ng, 3.9 ng, 2.0 ng) of pre-loaded dimerizable anti-CD19 salvage receptor for 24 hr, at a 1:1 E:T ratio. IL-2, IL-4, IL-17A, TNF and IFNγ amounts were measured.

Anti-BCMA salvage CAR T cells or untransduced T cells were co-cultured with CD19 positive Nalm-6 cells, with decreasing amounts (125 ng, 62.5 ng, 31.3 ng, 15.6 ng, 7.8 ng, 3.9 ng, 2.0 ng) of pre-loaded dimerizable anti-CD19 salvage receptor for 24 hr, at a 1:1 E:T ratio. Cytokine release assays performed on the co-culture supernatants showed that IL-2, IL-4, IL-17A, TNF and IFNγ were produced and that the amount of cytokine produced correlated to the amount of pre-loaded dimerizable anti-CD19 salvage receptor in the co-culture. FIG. 7.

Example 4

Anti-CD19 Salvage Receptor Redirects Anti-BCMA Daric T Cells

A lentivirus comprising an MND promoter operably linked to polynucleotide sequence encoding an anti-BCMA DARIC was designed, constructed, and verified. The BCMA DARIC comprises a CD8α-derived signal peptide, a FRB variant (T82L), a CD8α derived transmembrane domain, an intracellular 4-1BB co-stimulatory domain, a CD3 zeta signaling domain, a P2A sequence, an IgK-derived signal peptide, a single-chain variable fragment (scFv) targeting the BCMA antigen, a G4S linker sequence, a FKBP12 domain, and an amnion less (AMN) derived transmembrane domain (SEQ ID NO: 6).

Figure 8A:
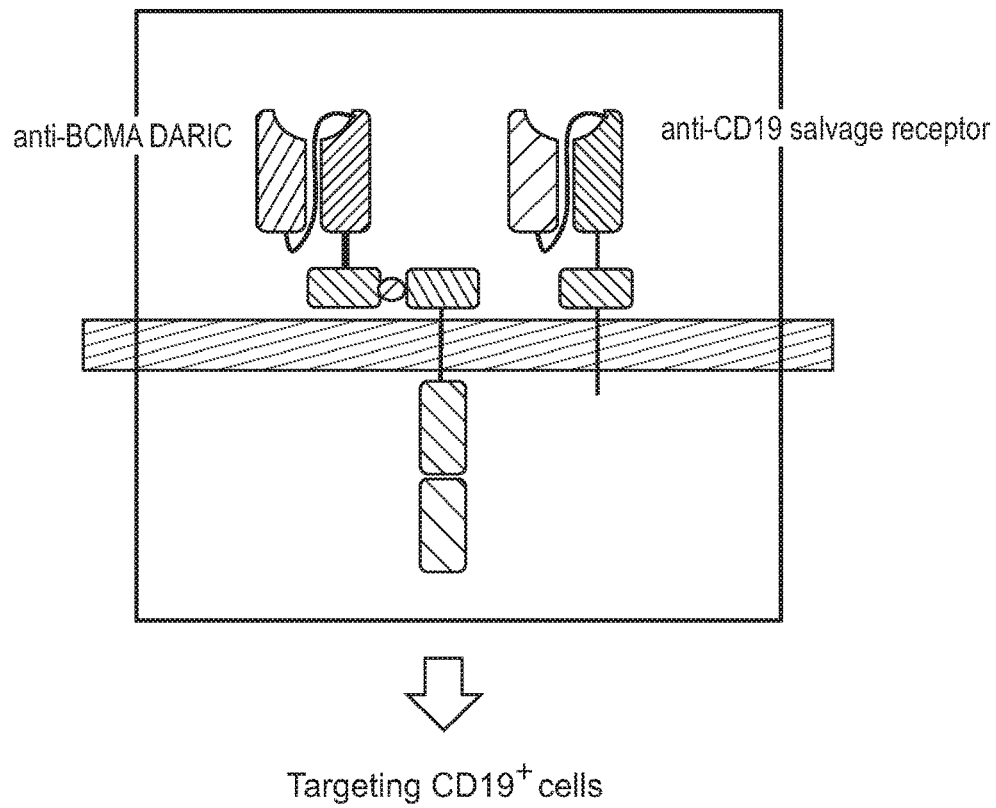
FIG. 8A shows a cartoon of an anti-BCMA DARIC and a dimerizable anti-CD19 salvage receptor system.
Figure 8B:
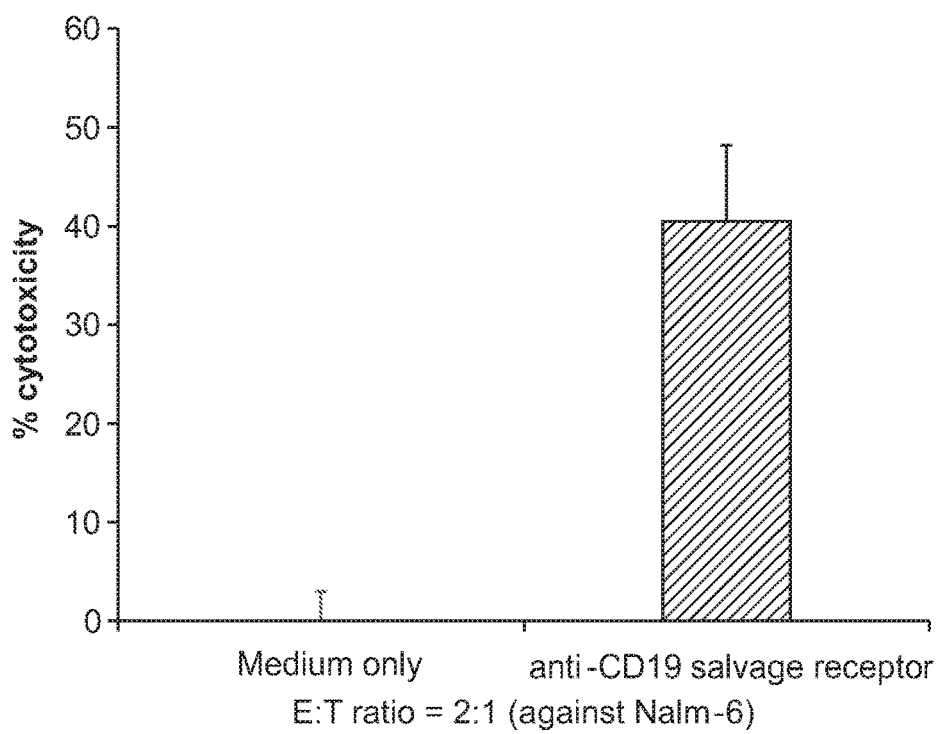
FIG. 8B shows that anti-BCMA DARIC T cells can be redirected to CD19 expressing Nalm-6 cells with an anti-CD19 salvage receptor.
Figure 8C:
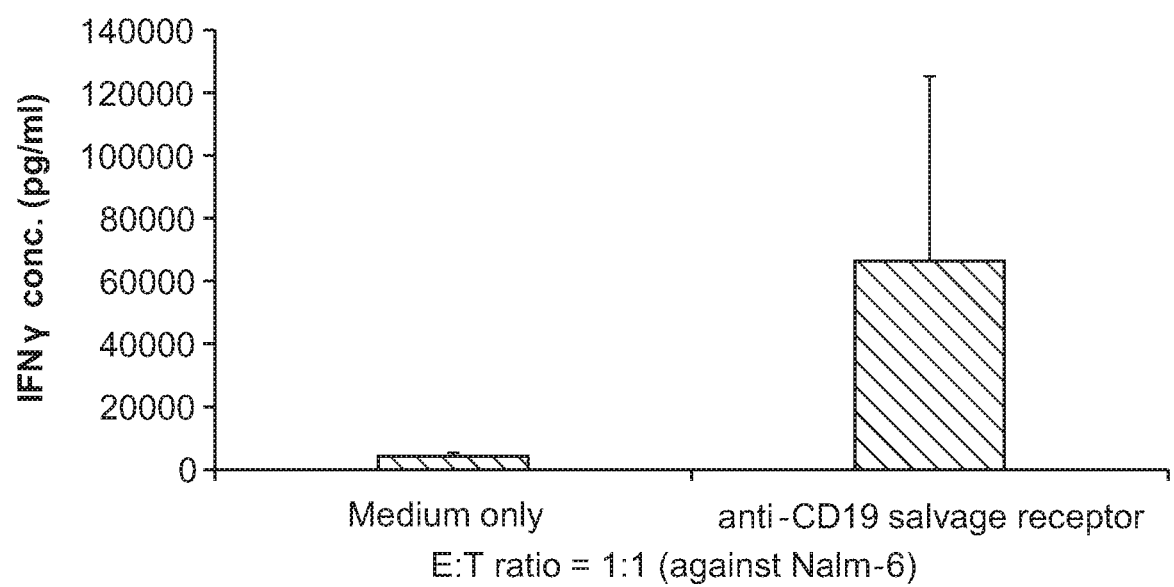
FIG. 8C shows that anti-BCMA DARIC T cells only secrete detectable levels of IFNγ when co-cultured with CD19 expressing Nalm-6 cells in the presence of an anti-CD19 salvage receptor.

The ability to redirect anti-BCMA DARIC T cells to CD19 expressing Nalm-6 cells with an anti-CD19 salvage receptor was assessed. Anti-BCMA-DARIC T cells were co-cultured with a 50:50 mixture of the CD19+ Nalm-6 (GFP) and K562 (BFP) target cells in the presence or absence of 250 ng anti-CD19 salvage receptor at an effector to target (E:T) ratio of 2:1. The anti-CD19 salvage receptor was able to redirect the cytotoxicity of anti-BCMA DARIC T cells to the CD19+ Nalm-6 cells. FIG. 8B. Cytokine release assays were also performed. Anti-BCMA DARIC T cells were co-cultured with Nalm-6 cells at a 1:1 E:T ratio for 24 hours in the presence or absence of 250 ng anti-CD19 salvage receptor. IFNγ was only produced from co-cultures containing anti-CD19 salvage receptor. FIG. 8C.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A polypeptide comprising a salvage chimeric antigen receptor (CAR) comprising:
   a) an extracellular antigen binding domain;
   b) an extracellular multimerization domain;
   c) a transmembrane domain;
   d) one or more intracellular co-stimulatory signaling domains; and
   e) a primary signaling domain.

2. The polypeptide comprising the salvage CAR of claim 1, wherein:
   (a) the extracellular antigen binding domain comprises an antibody or antigen binding fragment thereof;
   (b) the extracellular antigen binding domain comprises an antibody or antigen binding fragment thereof selected from the group consisting of: a Camel Ig, Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), and single-domain antibody (sdAb, Nanobody);
   (c) the extracellular antigen binding domain is an scFv;
   (d) the extracellular antigen binding domain binds an antigen selected from the group consisting of: alpha folate receptor, 5T4, $\alpha_v\beta_6$ integrin, BCMA, B7-H3, B7-H6, CAIX, CD16, CD19, CD20, CD22, CD30, CD33, CD37, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, VEGFR2, and WT-1;
   (e) the extracellular antigen binding domain binds an antigen selected from the group consisting of: BCMA, CD19, CSPG4, PSCA, ROR1, and TAG72;
   (f) the extracellular antigen binding domain binds an antigen selected from the group consisting of: BCMA, CD19, CD20, CD22, CD23, CD33, CD37, CD52, CD80, and HLA-DR;
   (g) the extracellular antigen binding domain binds BCMA or CD19;
   (h) the extracellular antigen binding domain binds an antigen expressed on a cancer cell;
   (i) the extracellular antigen binding domain binds an antigen expressed on a solid cancer cell;
   cell;
   (j) the extracellular antigen binding domain binds an antigen expressed on a liquid cancer
   (k) the extracellular antigen binding domain binds an antigen expressed on a malignant B cell; or
   (l) the extracellular antigen binding domain binds an antigen expressed on a malignant plasma cell.

3. The polypeptide comprising the salvage CAR of claim 1, wherein:
   (a) the multimerization domain is selected from the group consisting of: an FKBP polypeptide, an FRB polypeptide, a calcineurin polypeptide, a cyclophilin polypeptide, a bacterial DHFR polypeptide, a PYL1 polypeptide, an ABI1 polypeptide, a GIB1 polypeptide, a GAI polypeptide, and variants thereof;

(b) the multimerization domain is selected from the group consisting of: an FKBP polypeptide, an FRB polypeptide, and variants thereof; or (c) the multimerization domain is selected from the group consisting of: an FKBP12 polypeptide and an FRB T2098L polypeptide.

4. The polypeptide comprising the salvage CAR of claim 1, wherein:

(a) the transmembrane domain is isolated from a polypeptide selected from the group consisting of: alpha or beta chain of the T-cell receptor, CDδ, CD3ε, CDγ, CD3ζ; CD4, CD5, CD8α, CD9, CD 16, CD22, CD27, CD28, CD33, CD37, CD45, CD64, CD71, CD80, CD86, CD 134, CD137, CD152, CD154, AMN, and PD1;

(b) the transmembrane domain is isolated from a polypeptide selected from the group consisting of: CD8α; CD4, CD45, PD1, and CD152; or (c) the transmembrane domain is isolated from CD8α.

5. The polypeptide comprising the salvage CAR of claim 1, wherein:

(a) the one or more co-stimulatory signaling domains and/or primary signaling domains comprise an immunoreceptor tyrosine activation motif (ITAM);

(b) the one or more co-stimulatory signaling domains are isolated from a co-stimulatory molecule selected from the group consisting of: TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (0X40), CD137 (4-1BB), CD278 (ICOS), DAP10, LAT, NKD2C, SLP76, TRIM, and ZAP70;

(c) the one or more co-stimulatory signaling domains are isolated from a co-stimulatory molecule selected from the group consisting of: CD28, CD134, CD137, and CD278;

(d) the one or more co-stimulatory signaling domains is isolated from CD137;

(e) the primary signaling domain isolated from a polypeptide selected from the group consisting of: FcRγ, FcRβ, CD3γ, CD3δ, CD3ε, CD3ζ; CD22, CD79a, CD79b, and CD66d; or (f) the primary signaling domain isolated from a CD3ζ.

6. A polypeptide comprising a salvage CAR comprising:

(a) a signal peptide, an anti-BCMA scFv, a linker, an FRB (T82L) multimerization domain, a CD8α hinge and transmembrane domain, a 4-1BB co-stimulatory domain, and a CD3ζ primary signaling domain; or (b) an amino acid sequence set forth in SEQ ID NO: 2.

7. A polynucleotide encoding the polypeptide comprising the salvage CAR of claim 1.

8. A vector encoding the polynucleotide of claim 7 and a-polynucleotide encoding a dimerizable salvage receptor comprising:

a) an antigen binding domain;
b) a linker;
c) a multimerization domain;
d) a hinge domain; and
e) an anchor domain.

9. The vector of claim 8, wherein:

(a) the vector is an expression vector;
(b) the vector is an episomal vector;
(c) the vector is a viral vector;
(d) the vector is a retroviral vector; or
(e) the vector is a lentiviral vector.

10. A cell comprising the vector of claim 8.

11. The cell of claim 10, wherein the cell is:

(a) a hematopoietic cell;
(b) an immune effector cell;
(c) $CD3^+$, $CD4^+$, $CD8^+$, or a combination thereof;
(d) a T cell; or
(e) a cytotoxic T lymphocyte (CTL), a tumor infiltrating lymphocyte (TIL), or a helper T cell.

12. A composition comprising the cell of claim 11.

13. A composition comprising a physiologically acceptable carrier and the cell of claim 11.

14. A salvage CAR system comprising:

a) a T cell comprising the polypeptide comprising the salvage CAR of claim 1 that binds a first antigen,
b) a dimerizable salvage receptor that binds a second antigen, wherein the dimerizable salvage receptor comprises
  i) an antigen binding domain;
  ii) a linker;
  iii) a multimerization domain;
  iv) a hinge domain; and
  v) an anchor domain; and
c) a bridging factor.

* * * * *

UNITED STATES PATENT AND TRADEMARK OFFICE
CERTIFICATE OF CORRECTION

PATENT NO. : 11,976,116 B2
APPLICATION NO. : 16/092946
DATED : May 7, 2024
INVENTOR(S) : Wai-Hang Leung It is certified that error appears in the above-identified patent and that said Letters Patent is hereby corrected as shown below:

In the Claims

At Column 105, Claim number 2, Line number 60, please delete "$\alpha_c\beta_6$" and replace with --$\alpha v\beta 6$--.

At Column 106, Claim number 2, Line number 55, please delete second occurrence of the term "cell;".

At Column 107, Claim number 4, Line number 14, please delete "CD3ζ;" and replace with --CD3ζ,--.

At Column 107, Claim number 4, Line number 19, please delete "CD8α;" and replace with --CD8α,--.

At Column 107, Claim number 5, Line number 32, please delete "0X40" and replace with --OX40--.

At Column 107, Claim number 5, Line number 43, please delete "CD3ζ;" and replace with --CD3ζ,--.

At Column 108, Claim number 8, Line number 10, please delete "a-polynucleotide" and replace with --a polynucleotide--.

Signed and Sealed this
Twenty-ninth Day of October, 2024

Katherine Kelly Vidal
*Director of the United States Patent and Trademark Office*

SEQUENCE LISTING

```
<160> NUMBER OF SEQ ID NOS: 47

<210> SEQ ID NO 1
<211> LENGTH: 493
<212> TYPE: PRT
<213> ORGANISM: Artificial Sequence
<220> FEATURE:
<223> OTHER INFORMATION: Polypeptide sequence for an anti-BCMA chimeric
      antigen receptor

<400> SEQUENCE: 1

Met Ala Leu Pro Val Thr Ala Leu Leu Leu Pro Leu Ala Leu Leu Leu
1               5                   10                  15

His Ala Ala Arg Pro Asp Ile Val Leu Thr Gln Ser Pro Pro Ser Leu
            20                  25                  30

Ala Met Ser Leu Gly Lys Arg Ala Thr Ile Ser Cys Arg Ala Ser Glu
        35                  40                  45

Ser Val Thr Ile Leu Gly Ser His Leu Ile His Trp Tyr Gln Gln Lys
    50                  55                  60

Pro Gly Gln Pro Pro Thr Leu Leu Ile Gln Leu Ala Ser Asn Val Gln
65                  70                  75                  80

Thr Gly Val Pro Ala Arg Phe Ser Gly Ser Gly Ser Arg Thr Asp Phe
                85                  90                  95

Thr Leu Thr Ile Asp Pro Val Glu Glu Asp Asp Val Ala Val Tyr Tyr
            100                 105                 110

Cys Leu Gln Ser Arg Thr Ile Pro Arg Thr Phe Gly Gly Gly Thr Lys
        115                 120                 125

Leu Glu Ile Lys Gly Ser Thr Ser Gly Ser Gly Lys Pro Gly Ser Gly
    130                 135                 140

Glu Gly Ser Thr Lys Gly Gln Ile Gln Leu Val Gln Ser Gly Pro Glu
145                 150                 155                 160

Leu Lys Lys Pro Gly Glu Thr Val Lys Ile Ser Cys Lys Ala Ser Gly
                165                 170                 175
```

```
Tyr Thr Phe Thr Asp Tyr Ser Ile Asn Trp Val Lys Arg Ala Pro Gly
            180                 185                 190

Lys Gly Leu Lys Trp Met Gly Trp Ile Asn Thr Glu Thr Arg Glu Pro
        195                 200                 205

Ala Tyr Ala Tyr Asp Phe Arg Gly Arg Phe Ala Phe Ser Leu Glu Thr
        210                 215                 220

Ser Ala Ser Thr Ala Tyr Leu Gln Ile Asn Asn Leu Lys Tyr Glu Asp
225                 230                 235                 240

Thr Ala Thr Tyr Phe Cys Ala Leu Asp Tyr Ser Tyr Ala Met Asp Tyr
                245                 250                 255

Trp Gly Gln Gly Thr Ser Val Thr Val Ser Ser Ala Ala Thr Thr
            260                 265                 270

Thr Pro Ala Pro Arg Pro Pro Thr Pro Ala Pro Thr Ile Ala Ser Gln
            275                 280                 285

Pro Leu Ser Leu Arg Pro Glu Ala Cys Arg Pro Ala Ala Gly Gly Ala
290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490
```

<210> SEQ ID NO 2
<211> LENGTH: 594
<212> TYPE: PRT
<213> ORGANISM: Artificial Sequence
<220> FEATURE:
<223> OTHER INFORMATION: Polypeptide sequence for anti-BCMA chimeric
      antigen receptor comprising multimerization domain

<400> SEQUENCE: 2

```
Met Ala Leu Pro Val Thr Ala Leu Leu Leu Pro Leu Ala Leu Leu Leu
1               5                   10                  15

His Ala Ala Arg Pro Asp Ile Val Leu Thr Gln Ser Pro Pro Ser Leu
            20                  25                  30

Ala Met Ser Leu Gly Lys Arg Ala Thr Ile Ser Cys Arg Ala Ser Glu
        35                  40                  45
```

```
Ser Val Thr Ile Leu Gly Ser His Leu Ile His Trp Tyr Gln Gln Lys
    50                  55                  60
Pro Gly Gln Pro Pro Thr Leu Leu Ile Gln Leu Ala Ser Asn Val Gln
65                  70                  75                  80
Thr Gly Val Pro Ala Arg Phe Ser Gly Ser Gly Ser Arg Thr Asp Phe
                85                  90                  95
Thr Leu Thr Ile Asp Pro Val Glu Glu Asp Val Ala Val Tyr Tyr
            100                 105                 110
Cys Leu Gln Ser Arg Thr Ile Pro Arg Thr Phe Gly Gly Gly Thr Lys
        115                 120                 125
Leu Glu Ile Lys Gly Ser Thr Ser Gly Ser Gly Lys Pro Gly Ser Gly
130                 135                 140
Glu Gly Ser Thr Lys Gly Gln Ile Gln Leu Val Gln Ser Gly Pro Glu
145                 150                 155                 160
Leu Lys Lys Pro Gly Glu Thr Val Lys Ile Ser Cys Lys Ala Ser Gly
                165                 170                 175
Tyr Thr Phe Thr Asp Tyr Ser Ile Asn Trp Val Lys Arg Ala Pro Gly
            180                 185                 190
Lys Gly Leu Lys Trp Met Gly Trp Ile Asn Thr Glu Thr Arg Glu Pro
        195                 200                 205
Ala Tyr Ala Tyr Asp Phe Arg Gly Arg Phe Ala Phe Ser Leu Glu Thr
210                 215                 220
Ser Ala Ser Thr Ala Tyr Leu Gln Ile Asn Asn Leu Lys Tyr Glu Asp
225                 230                 235                 240
Thr Ala Thr Tyr Phe Cys Ala Leu Asp Tyr Ser Tyr Ala Met Asp Tyr
                245                 250                 255
Trp Gly Gln Gly Thr Ser Val Thr Val Ser Ser Gly Pro Gly Gly Gly
            260                 265                 270
Gly Ser Ile Leu Trp His Glu Met Trp His Glu Gly Leu Glu Glu Ala
        275                 280                 285
Ser Arg Leu Tyr Phe Gly Glu Arg Asn Val Lys Gly Met Phe Glu Val
290                 295                 300
Leu Glu Pro Leu His Ala Met Met Glu Arg Gly Pro Gln Thr Leu Lys
305                 310                 315                 320
Glu Thr Ser Phe Asn Gln Ala Tyr Gly Arg Asp Leu Met Glu Ala Gln
                325                 330                 335
Glu Trp Cys Arg Lys Tyr Met Lys Ser Gly Asn Val Lys Asp Leu Leu
            340                 345                 350
Gln Ala Trp Asp Leu Tyr Tyr His Val Phe Arg Arg Ile Ser Lys Ala
        355                 360                 365
Ser Ala Lys Pro Thr Thr Thr Pro Ala Pro Arg Pro Pro Thr Pro Ala
370                 375                 380
Pro Thr Ile Ala Ser Gln Pro Leu Ser Leu Arg Pro Glu Ala Cys Arg
385                 390                 395                 400
Pro Ala Ala Gly Gly Ala Val His Thr Arg Gly Leu Asp Phe Ala Cys
                405                 410                 415
Asp Ile Tyr Ile Trp Ala Pro Leu Ala Gly Thr Cys Gly Val Leu Leu
            420                 425                 430
Leu Ser Leu Val Ile Thr Met His Lys Arg Gly Arg Lys Lys Leu Leu
        435                 440                 445
Tyr Ile Phe Lys Gln Pro Phe Met Arg Pro Val Gln Thr Thr Gln Glu
450                 455                 460
```

```
Glu Asp Gly Cys Ser Cys Arg Phe Pro Glu Glu Glu Gly Gly Cys
465                 470                 475                 480

Glu Leu Arg Val Lys Phe Ser Arg Ser Ala Asp Ala Pro Ala Tyr Gln
                485                 490                 495

Gln Gly Gln Asn Gln Leu Tyr Asn Glu Leu Asn Leu Gly Arg Arg Glu
            500                 505                 510

Glu Tyr Asp Val Leu Asp Lys Arg Arg Gly Arg Asp Pro Glu Met Gly
        515                 520                 525

Gly Lys Pro Arg Arg Lys Asn Pro Gln Glu Gly Leu Tyr Asn Glu Leu
    530                 535                 540

Gln Lys Asp Lys Met Ala Glu Ala Tyr Ser Glu Ile Gly Met Lys Gly
545                 550                 555                 560

Glu Arg Arg Arg Gly Lys Gly His Asp Gly Leu Tyr Gln Gly Leu Ser
                565                 570                 575

Thr Ala Thr Lys Asp Thr Tyr Asp Ala Leu His Met Gln Ala Leu Pro
                580                 585                 590

Pro Arg

<210> SEQ ID NO 3
<211> LENGTH: 387
<212> TYPE: PRT
<213> ORGANISM: Artificial Sequence
<220> FEATURE:
<223> OTHER INFORMATION: Polypeptide sequence for a dimerizable
      anti-CD19 salvage receptor

<400> SEQUENCE: 3

Met Glu Thr Asp Thr Leu Leu Leu Trp Val Leu Leu Leu Trp Val Pro
1               5                   10                  15

Gly Ser Thr Gly Asp Tyr Lys Asp Glu Gly Ser Asp Ile Gln Met Thr
            20                  25                  30

Gln Thr Thr Ser Ser Leu Ser Ala Ser Leu Gly Asp Arg Val Thr Ile
        35                  40                  45

Ser Cys Arg Ala Ser Gln Asp Ile Ser Lys Tyr Leu Asn Trp Tyr Gln
50                  55                  60

Gln Lys Pro Asp Gly Thr Val Lys Leu Leu Ile Tyr His Thr Ser Arg
65                  70                  75                  80

Leu His Ser Gly Val Pro Ser Arg Phe Ser Gly Ser Gly Ser Gly Thr
                85                  90                  95

Asp Tyr Ser Leu Thr Ile Ser Asn Leu Glu Gln Glu Asp Ile Ala Thr
            100                 105                 110

Tyr Phe Cys Gln Gln Gly Asn Thr Leu Pro Tyr Thr Phe Gly Gly Gly
        115                 120                 125

Thr Lys Leu Glu Ile Thr Gly Ser Thr Ser Gly Ser Gly Lys Pro Gly
    130                 135                 140

Ser Gly Glu Gly Ser Thr Lys Gly Glu Val Lys Leu Gln Glu Ser Gly
145                 150                 155                 160

Pro Gly Leu Val Ala Pro Ser Gln Ser Leu Ser Val Thr Cys Thr Val
                165                 170                 175

Ser Gly Val Ser Leu Pro Asp Tyr Gly Val Ser Trp Ile Arg Gln Pro
            180                 185                 190

Pro Arg Lys Gly Leu Glu Trp Leu Gly Val Ile Trp Gly Ser Glu Thr
        195                 200                 205

Thr Tyr Tyr Asn Ser Ala Leu Lys Ser Arg Leu Thr Ile Ile Lys Asp
    210                 215                 220
```

```
Asn Ser Lys Ser Gln Val Phe Leu Lys Met Asn Ser Leu Gln Thr Asp
225                 230                 235                 240

Asp Thr Ala Ile Tyr Tyr Cys Ala Lys His Tyr Tyr Tyr Gly Gly Ser
            245                 250                 255

Tyr Ala Met Asp Tyr Trp Gly Gln Gly Thr Ser Val Thr Val Ser Ser
        260                 265                 270

Ala Ser Gly Ser Gly Gly Val Gln Val Glu Thr Ile Ser Pro Gly Asp
        275                 280                 285

Gly Arg Thr Phe Pro Lys Arg Gly Gln Thr Cys Val Val His Tyr Thr
    290                 295                 300

Gly Met Leu Glu Asp Gly Lys Lys Phe Asp Ser Ser Arg Asp Arg Asn
305                 310                 315                 320

Lys Pro Phe Lys Phe Met Leu Gly Lys Gln Glu Val Ile Arg Gly Trp
                325                 330                 335

Glu Glu Gly Val Ala Gln Met Ser Val Gly Gln Arg Ala Lys Leu Thr
            340                 345                 350

Ile Ser Pro Asp Tyr Ala Tyr Gly Ala Thr Gly His Pro Gly Ile Ile
        355                 360                 365

Pro Pro His Ala Thr Leu Val Phe Asp Val Glu Leu Leu Lys Leu Glu
370                 375                 380

Gly Gly Arg
385

<210> SEQ ID NO 4
<211> LENGTH: 644
<212> TYPE: PRT
<213> ORGANISM: Artificial Sequence
<220> FEATURE:
<223> OTHER INFORMATION: Polypeptide sequence for a dimerizable
      anti-CD19 salvage receptor with T2A mCherry

<400> SEQUENCE: 4

Met Glu Thr Asp Thr Leu Leu Leu Trp Val Leu Leu Leu Trp Val Pro
1               5                   10                  15

Gly Ser Thr Gly Asp Tyr Lys Asp Glu Gly Ser Asp Ile Gln Met Thr
            20                  25                  30

Gln Thr Thr Ser Ser Leu Ser Ala Ser Leu Gly Asp Arg Val Thr Ile
        35                  40                  45

Ser Cys Arg Ala Ser Gln Asp Ile Ser Lys Tyr Leu Asn Trp Tyr Gln
    50                  55                  60

Gln Lys Pro Asp Gly Thr Val Lys Leu Leu Ile Tyr His Thr Ser Arg
65                  70                  75                  80

Leu His Ser Gly Val Pro Ser Arg Phe Ser Gly Ser Gly Ser Gly Thr
                85                  90                  95

Asp Tyr Ser Leu Thr Ile Ser Asn Leu Glu Gln Glu Asp Ile Ala Thr
            100                 105                 110

Tyr Phe Cys Gln Gln Gly Asn Thr Leu Pro Tyr Thr Phe Gly Gly Gly
        115                 120                 125

Thr Lys Leu Glu Ile Thr Gly Ser Thr Ser Gly Ser Gly Lys Pro Gly
    130                 135                 140

Ser Gly Glu Gly Ser Thr Lys Gly Glu Val Lys Leu Gln Glu Ser Gly
145                 150                 155                 160

Pro Gly Leu Val Ala Pro Ser Gln Ser Leu Ser Val Thr Cys Thr Val
                165                 170                 175

Ser Gly Val Ser Leu Pro Asp Tyr Gly Val Ser Trp Ile Arg Gln Pro
            180                 185                 190
```

```
Pro Arg Lys Gly Leu Glu Trp Leu Gly Val Ile Trp Gly Ser Glu Thr
            195                 200                 205

Thr Tyr Tyr Asn Ser Ala Leu Lys Ser Arg Leu Thr Ile Ile Lys Asp
        210                 215                 220

Asn Ser Lys Ser Gln Val Phe Leu Lys Met Asn Ser Leu Gln Thr Asp
225                 230                 235                 240

Asp Thr Ala Ile Tyr Tyr Cys Ala Lys His Tyr Tyr Gly Gly Ser
                245                 250                 255

Tyr Ala Met Asp Tyr Trp Gly Gln Gly Thr Ser Val Thr Val Ser Ser
                260                 265                 270

Ala Ser Gly Ser Gly Gly Val Gln Val Glu Thr Ile Ser Pro Gly Asp
            275                 280                 285

Gly Arg Thr Phe Pro Lys Arg Gly Gln Thr Cys Val Val His Tyr Thr
            290                 295                 300

Gly Met Leu Glu Asp Gly Lys Lys Phe Asp Ser Ser Arg Asp Arg Asn
305                 310                 315                 320

Lys Pro Phe Lys Phe Met Leu Gly Lys Gln Glu Val Ile Arg Gly Trp
                325                 330                 335

Glu Glu Gly Val Ala Gln Met Ser Val Gly Gln Arg Ala Lys Leu Thr
            340                 345                 350

Ile Ser Pro Asp Tyr Ala Tyr Gly Ala Thr Gly His Pro Gly Ile Ile
            355                 360                 365

Pro Pro His Ala Thr Leu Val Phe Asp Val Glu Leu Leu Lys Leu Glu
370                 375                 380

Gly Gly Arg Ser Gly Glu Gly Arg Gly Ser Leu Leu Thr Cys Gly Asp
385                 390                 395                 400

Val Glu Glu Asn Pro Gly Pro Ser Arg Val Ser Lys Gly Glu Glu Asp
                405                 410                 415

Asn Met Ala Ile Ile Lys Glu Phe Met Arg Phe Lys Val His Met Glu
            420                 425                 430

Gly Ser Val Asn Gly His Glu Phe Glu Ile Glu Gly Glu Gly Glu Gly
            435                 440                 445

Arg Pro Tyr Glu Gly Thr Gln Thr Ala Lys Leu Lys Val Thr Lys Gly
450                 455                 460

Gly Pro Leu Pro Phe Ala Trp Asp Ile Leu Ser Pro Gln Phe Met Tyr
465                 470                 475                 480

Gly Ser Lys Ala Tyr Val Lys His Pro Ala Asp Ile Pro Asp Tyr Leu
            485                 490                 495

Lys Leu Ser Phe Pro Glu Gly Phe Lys Trp Glu Arg Val Met Asn Phe
            500                 505                 510

Glu Asp Gly Gly Val Val Thr Val Thr Gln Asp Ser Ser Leu Gln Asp
            515                 520                 525

Gly Glu Phe Ile Tyr Lys Val Lys Leu Arg Gly Thr Asn Phe Pro Ser
530                 535                 540

Asp Gly Pro Val Met Gln Lys Lys Thr Met Gly Trp Glu Ala Ser Ser
545                 550                 555                 560

Glu Arg Met Tyr Pro Glu Asp Gly Ala Leu Lys Gly Glu Ile Lys Gln
                565                 570                 575

Arg Leu Lys Leu Lys Asp Gly Gly His Tyr Asp Ala Glu Val Lys Thr
            580                 585                 590

Thr Tyr Lys Ala Lys Lys Pro Val Gln Leu Pro Gly Ala Tyr Asn Val
            595                 600                 605
```

```
Asn Ile Lys Leu Asp Ile Thr Ser His Asn Glu Asp Tyr Thr Ile Val
    610                 615                 620

Glu Gln Tyr Glu Arg Ala Glu Gly Arg His Ser Thr Gly Gly Met Asp
625                 630                 635                 640

Glu Leu Tyr Lys

<210> SEQ ID NO 5
<211> LENGTH: 641
<212> TYPE: PRT
<213> ORGANISM: Artificial Sequence
<220> FEATURE:
<223> OTHER INFORMATION: Polypeptide sequence for a dimerizable
      anti-CD19 salvage receptor with T2A mCherry

<400> SEQUENCE: 5

Met Pro Leu Gly Leu Leu Trp Leu Gly Leu Ala Leu Leu Gly Ala Leu
1               5                   10                  15

His Ala Gln Ala Gly Ser Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser Ala Ser Gly Gly Gly
            260                 265                 270

Gly Ser Gly Val Gln Val Glu Thr Ile Ser Pro Gly Asp Gly Arg Thr
        275                 280                 285

Phe Pro Lys Arg Gly Gln Thr Cys Val Val His Tyr Thr Gly Met Leu
    290                 295                 300

Glu Asp Gly Lys Lys Phe Asp Ser Ser Arg Asp Arg Asn Lys Pro Phe
305                 310                 315                 320
```

```
Lys Phe Met Leu Gly Lys Gln Glu Val Ile Arg Gly Trp Glu Gly
            325                 330                 335

Val Ala Gln Met Ser Val Gly Gln Arg Ala Lys Leu Thr Ile Ser Pro
        340                 345                 350

Asp Tyr Ala Tyr Gly Ala Thr Gly His Pro Gly Ile Ile Pro Pro His
    355                 360                 365

Ala Thr Leu Val Phe Asp Val Glu Leu Leu Lys Leu Glu Gly Gly Arg
370                 375                 380

Ser Gly Glu Gly Arg Gly Ser Leu Leu Thr Cys Gly Asp Val Glu Glu
385                 390                 395                 400

Asn Pro Gly Pro Ser Arg Val Ser Lys Gly Glu Glu Asp Asn Met Ala
                405                 410                 415

Ile Ile Lys Glu Phe Met Arg Phe Lys Val His Met Glu Gly Ser Val
            420                 425                 430

Asn Gly His Glu Phe Glu Ile Glu Gly Glu Gly Glu Gly Arg Pro Tyr
        435                 440                 445

Glu Gly Thr Gln Thr Ala Lys Leu Lys Val Thr Lys Gly Gly Pro Leu
    450                 455                 460

Pro Phe Ala Trp Asp Ile Leu Ser Pro Gln Phe Met Tyr Gly Ser Lys
465                 470                 475                 480

Ala Tyr Val Lys His Pro Ala Asp Ile Pro Asp Tyr Leu Lys Leu Ser
                485                 490                 495

Phe Pro Glu Gly Phe Lys Trp Glu Arg Val Met Asn Phe Glu Asp Gly
            500                 505                 510

Gly Val Val Thr Val Thr Gln Asp Ser Ser Leu Gln Asp Gly Glu Phe
        515                 520                 525

Ile Tyr Lys Val Lys Leu Arg Gly Thr Asn Phe Pro Ser Asp Gly Pro
    530                 535                 540

Val Met Gln Lys Lys Thr Met Gly Trp Glu Ala Ser Ser Glu Arg Met
545                 550                 555                 560

Tyr Pro Glu Asp Gly Ala Leu Lys Gly Glu Ile Lys Gln Arg Leu Lys
                565                 570                 575

Leu Lys Asp Gly Gly His Tyr Asp Ala Glu Val Lys Thr Thr Tyr Lys
            580                 585                 590

Ala Lys Lys Pro Val Gln Leu Pro Gly Ala Tyr Asn Val Asn Ile Lys
        595                 600                 605

Leu Asp Ile Thr Ser His Asn Glu Asp Tyr Thr Ile Val Glu Gln Tyr
    610                 615                 620

Glu Arg Ala Glu Gly Arg His Ser Thr Gly Gly Met Asp Glu Leu Tyr
625                 630                 635                 640

Lys

<210> SEQ ID NO 6
<211> LENGTH: 739
<212> TYPE: PRT
<213> ORGANISM: Artificial Sequence
<220> FEATURE:
<223> OTHER INFORMATION: Polypeptide sequence for an anti-BCMA DARIC

<400> SEQUENCE: 6

Met Ala Leu Pro Val Thr Ala Leu Leu Leu Pro Leu Ala Leu Leu Leu
1               5                   10                  15

His Ala Ala Arg Pro Gly Ser Ile Leu Trp His Glu Met Trp His Glu
            20                  25                  30

Gly Leu Glu Glu Ala Ser Arg Leu Tyr Phe Gly Glu Arg Asn Val Lys
```

```
                35                  40                  45
Gly Met Phe Glu Val Leu Glu Pro Leu His Ala Met Met Glu Arg Gly
 50                  55                  60

Pro Gln Thr Leu Lys Glu Thr Ser Phe Asn Gln Ala Tyr Gly Arg Asp
 65                  70                  75                  80

Leu Met Glu Ala Gln Glu Trp Cys Arg Lys Tyr Met Lys Ser Gly Asn
                 85                  90                  95

Val Lys Asp Leu Leu Gln Ala Trp Asp Leu Tyr Tyr His Val Phe Arg
                100                 105                 110

Arg Ile Ser Lys Ala Ser Ala Gly Thr Gly Ser Asp Ile Tyr Ile Trp
                115                 120                 125

Ala Pro Leu Ala Gly Thr Cys Gly Val Leu Leu Ser Leu Val Ile
130                 135                 140

Thr Met His Lys Arg Gly Arg Lys Lys Leu Leu Tyr Ile Phe Lys Gln
145                 150                 155                 160

Pro Phe Met Arg Pro Val Gln Thr Thr Gln Glu Glu Asp Gly Cys Ser
                165                 170                 175

Cys Arg Phe Pro Glu Glu Glu Gly Gly Cys Glu Leu Arg Val Lys
                180                 185                 190

Phe Ser Arg Ser Ala Asp Ala Pro Ala Tyr Gln Gln Gly Gln Asn Gln
                195                 200                 205

Leu Tyr Asn Glu Leu Asn Leu Gly Arg Arg Glu Glu Tyr Asp Val Leu
                210                 215                 220

Asp Lys Arg Arg Gly Arg Asp Pro Glu Met Gly Gly Lys Pro Arg Arg
225                 230                 235                 240

Lys Asn Pro Gln Glu Gly Leu Tyr Asn Glu Leu Gln Lys Asp Lys Met
                245                 250                 255

Ala Glu Ala Tyr Ser Glu Ile Gly Met Lys Gly Glu Arg Arg Arg Gly
                260                 265                 270

Lys Gly His Asp Gly Leu Tyr Gln Gly Leu Ser Thr Ala Thr Lys Asp
                275                 280                 285

Thr Tyr Asp Ala Leu His Met Gln Ala Leu Pro Pro Arg Ser Gly Ser
290                 295                 300

Gly Ala Thr Asn Phe Ser Leu Leu Lys Gln Ala Gly Asp Val Glu Glu
305                 310                 315                 320

Asn Pro Gly Pro Ser Met Glu Thr Asp Thr Leu Leu Leu Trp Val Leu
                325                 330                 335

Leu Leu Trp Val Pro Gly Ser Thr Gly Asp Ile Val Leu Thr Gln Ser
                340                 345                 350

Pro Pro Ser Leu Ala Met Ser Leu Gly Lys Arg Ala Thr Ile Ser Cys
                355                 360                 365

Arg Ala Ser Glu Ser Val Thr Ile Leu Gly Ser His Leu Ile His Trp
                370                 375                 380

Tyr Gln Gln Lys Pro Gly Gln Pro Pro Thr Leu Leu Ile Gln Leu Ala
385                 390                 395                 400

Ser Asn Val Gln Thr Gly Val Pro Ala Arg Phe Ser Gly Ser Gly Ser
                405                 410                 415

Arg Thr Asp Phe Thr Leu Thr Ile Asp Pro Val Glu Glu Asp Asp Val
                420                 425                 430

Ala Val Tyr Tyr Cys Leu Gln Ser Arg Thr Ile Pro Arg Thr Phe Gly
                435                 440                 445

Gly Gly Thr Lys Leu Glu Ile Lys Gly Ser Thr Ser Gly Ser Gly Lys
450                 455                 460
```

-continued

```
Pro Gly Ser Gly Glu Gly Ser Thr Lys Gly Gln Ile Gln Leu Val Gln
465                 470                 475                 480

Ser Gly Pro Glu Leu Lys Lys Pro Gly Glu Thr Val Lys Ile Ser Cys
            485                 490                 495

Lys Ala Ser Gly Tyr Thr Phe Thr Asp Tyr Ser Ile Asn Trp Val Lys
        500                 505                 510

Arg Ala Pro Gly Lys Gly Leu Lys Trp Met Gly Trp Ile Asn Thr Glu
    515                 520                 525

Thr Arg Glu Pro Ala Tyr Ala Tyr Asp Phe Arg Gly Arg Phe Ala Phe
530                 535                 540

Ser Leu Glu Thr Ser Ala Ser Thr Ala Tyr Leu Gln Ile Asn Asn Leu
545                 550                 555                 560

Lys Tyr Glu Asp Thr Ala Thr Tyr Phe Cys Ala Leu Asp Tyr Ser Tyr
                565                 570                 575

Ala Met Asp Tyr Trp Gly Gln Gly Thr Ser Val Thr Val Ser Ser Pro
            580                 585                 590

Arg Gly Gly Gly Gly Ser Gly Val Gln Val Glu Thr Ile Ser Pro Gly
        595                 600                 605

Asp Gly Arg Thr Phe Pro Lys Arg Gly Gln Thr Cys Val Val His Tyr
610                 615                 620

Thr Gly Met Leu Glu Asp Gly Lys Lys Phe Asp Ser Ser Arg Asp Arg
625                 630                 635                 640

Asn Lys Pro Phe Lys Phe Met Leu Gly Lys Gln Glu Val Ile Arg Gly
                645                 650                 655

Trp Glu Glu Gly Val Ala Gln Met Ser Val Gly Gln Arg Ala Lys Leu
            660                 665                 670

Thr Ile Ser Pro Asp Tyr Ala Tyr Gly Ala Thr Gly His Pro Gly Ile
        675                 680                 685

Ile Pro Pro His Ala Thr Leu Val Phe Asp Val Glu Leu Leu Lys Leu
690                 695                 700

Glu Gly Gly Arg Val Trp Gly Ser Ser Ala Ala Gly Leu Ala Gly Gly
705                 710                 715                 720

Val Ala Ala Ala Val Leu Leu Ala Leu Leu Val Leu Leu Val Ala Pro
                725                 730                 735

Pro Leu Leu

<210> SEQ ID NO 7
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 7

Asp Gly Gly Gly Ser
1               5

<210> SEQ ID NO 8
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 8

Thr Gly Glu Lys Pro
1               5
```

```
<210> SEQ ID NO 9
<211> LENGTH: 4
<212> TYPE: PRT
<213> ORGANISM: Artificial Sequence
<220> FEATURE:
<223> OTHER INFORMATION: Exemplary linker sequence

<400> SEQUENCE: 9

Gly Gly Arg Arg
1

<210> SEQ ID NO 10
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 10

Gly Gly Gly Gly Ser
1               5

<210> SEQ ID NO 11
<211> LENGTH: 14
<212> TYPE: PRT
<213> ORGANISM: Artificial Sequence
<220> FEATURE:
<223> OTHER INFORMATION: Exemplary linker sequence

<400> SEQUENCE: 11

Glu Gly Lys Ser Ser Gly Ser Gly Ser Glu Ser Lys Val Asp
1               5                   10

<210> SEQ ID NO 12
<211> LENGTH: 18
<212> TYPE: PRT
<213> ORGANISM: Artificial Sequence
<220> FEATURE:
<223> OTHER INFORMATION: Exemplary linker sequence

<400> SEQUENCE: 12

Lys Glu Ser Gly Ser Val Ser Ser Glu Gln Leu Ala Gln Phe Arg Ser
1               5                   10                  15

Leu Asp

<210> SEQ ID NO 13
<211> LENGTH: 8
<212> TYPE: PRT
<213> ORGANISM: Artificial Sequence
<220> FEATURE:
<223> OTHER INFORMATION: Exemplary linker sequence

<400> SEQUENCE: 13

Gly Gly Arg Arg Gly Gly Gly Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Exemplary linker sequence

<400> SEQUENCE: 14

Leu Arg Gln Arg Asp Gly Glu Arg Pro
```

```
1               5

<210> SEQ ID NO 15
<211> LENGTH: 12
<212> TYPE: PRT
<213> ORGANISM: Artificial Sequence
<220> FEATURE:
<223> OTHER INFORMATION: Exemplary linker sequence

<400> SEQUENCE: 15

Leu Arg Gln Lys Asp Gly Gly Gly Ser Glu Arg Pro
1               5                   10

<210> SEQ ID NO 16
<211> LENGTH: 16
<212> TYPE: PRT
<213> ORGANISM: Artificial Sequence
<220> FEATURE:
<223> OTHER INFORMATION: Exemplary linker sequence

<400> SEQUENCE: 16

Leu Arg Gln Lys Asp Gly Gly Gly Ser Gly Gly Gly Ser Glu Arg Pro
1               5                   10                  15

<210> SEQ ID NO 17
<211> LENGTH: 18
<212> TYPE: PRT
<213> ORGANISM: Artificial Sequence
<220> FEATURE:
<223> OTHER INFORMATION: Exemplary linker sequence

<400> SEQUENCE: 17

Gly Ser Thr Ser Gly Ser Gly Lys Pro Gly Ser Gly Glu Gly Ser Thr
1               5                   10                  15

Lys Gly

<210> SEQ ID NO 18
<211> LENGTH: 7
<212> TYPE: PRT
<213> ORGANISM: Artificial Sequence
<220> FEATURE:
<223> OTHER INFORMATION: Cleavage sequence by TEV protease
<220> FEATURE:
<221> NAME/KEY: misc_feature
<222> LOCATION: (2)..(3)
<223> OTHER INFORMATION: Xaa is any amino acid
<220> FEATURE:
<221> NAME/KEY: misc_feature
<222> LOCATION: (5)..(5)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa = Gly or Ser

<400> SEQUENCE: 18

Glu Xaa Xaa Tyr Xaa Gln Xaa
1               5

<210> SEQ ID NO 19
<211> LENGTH: 7
<212> TYPE: PRT
<213> ORGANISM: Artificial Sequence
<220> FEATURE:
<223> OTHER INFORMATION: Cleavage sequence by TEV protease

<400> SEQUENCE: 19

Glu Asn Leu Tyr Phe Gln Gly
```

```
<210> SEQ ID NO 20
<211> LENGTH: 7
<212> TYPE: PRT
<213> ORGANISM: Artificial Sequence
<220> FEATURE:
<223> OTHER INFORMATION: Cleavage sequence by TEV protease

<400> SEQUENCE: 20

Glu Asn Leu Tyr Phe Gln Ser
1               5

<210> SEQ ID NO 21
<211> LENGTH: 22
<212> TYPE: PRT
<213> ORGANISM: Artificial Sequence
<220> FEATURE:
<223> OTHER INFORMATION: Self-cleaving polypeptide comprising 2A site

<400> SEQUENCE: 21

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 22
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 22

Ala Thr Asn Phe Ser Leu Leu Lys Gln Ala Gly Asp Val Glu Glu Asn
1               5                   10                  15

Pro Gly Pro

<210> SEQ ID NO 23
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 23

Leu Leu Lys Gln Ala Gly Asp Val Glu Glu Asn Pro Gly Pro
1               5                   10

<210> SEQ ID NO 24
<211> LENGTH: 21
<212> TYPE: PRT
<213> ORGANISM: Artificial Sequence
<220> FEATURE:
<223> OTHER INFORMATION: Self-cleaving polypeptide comprising 2A site

<400> SEQUENCE: 24

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 25
<211> LENGTH: 18
<212> TYPE: PRT
```

```
<213> ORGANISM: Artificial Sequence
<220> FEATURE:
<223> OTHER INFORMATION: Self-cleaving polypeptide comprising 2A site

<400> SEQUENCE: 25

Glu Gly Arg Gly Ser Leu Leu Thr Cys Gly Asp Val Glu Glu Asn Pro
1               5                   10                  15

Gly Pro

<210> SEQ ID NO 26
<211> LENGTH: 13
<212> TYPE: PRT
<213> ORGANISM: Artificial Sequence
<220> FEATURE:
<223> OTHER INFORMATION: Self-cleaving polypeptide comprising 2A site

<400> SEQUENCE: 26

Leu Leu Thr Cys Gly Asp Val Glu Glu Asn Pro Gly Pro
1               5                   10

<210> SEQ ID NO 27
<211> LENGTH: 23
<212> TYPE: PRT
<213> ORGANISM: Artificial Sequence
<220> FEATURE:
<223> OTHER INFORMATION: Self-cleaving polypeptide comprising 2A site

<400> SEQUENCE: 27

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 28
<211> LENGTH: 20
<212> TYPE: PRT
<213> ORGANISM: Artificial Sequence
<220> FEATURE:
<223> OTHER INFORMATION: Self-cleaving polypeptide comprising 2A site

<400> SEQUENCE: 28

Gln Cys Thr Asn Tyr Ala Leu Leu Lys Leu Ala Gly Asp Val Glu Ser
1               5                   10                  15

Asn Pro Gly Pro
            20

<210> SEQ ID NO 29
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 29

Leu Leu Lys Leu Ala Gly Asp Val Glu Ser Asn Pro Gly Pro
1               5                   10

<210> SEQ ID NO 30
<211> LENGTH: 25
<212> TYPE: PRT
<213> ORGANISM: Artificial Sequence
<220> FEATURE:
<223> OTHER INFORMATION: Self-cleaving polypeptide comprising 2A site

<400> SEQUENCE: 30
```

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 31
<211> LENGTH: 22
<212> TYPE: PRT
<213> ORGANISM: Artificial Sequence
<220> FEATURE:
<223> OTHER INFORMATION: Self-cleaving polypeptide comprising 2A site

<400> SEQUENCE: 31

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 32
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 32

Leu Leu Lys Leu Ala Gly Asp Val Glu Ser Asn Pro Gly Pro
1               5                   10

<210> SEQ ID NO 33
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 33

Leu Leu Asn Phe Asp Leu Leu Lys Leu Ala Gly Asp Val Glu Ser Asn
1               5                   10                  15

Pro Gly Pro

<210> SEQ ID NO 34
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 34

Thr Leu Asn Phe Asp Leu Leu Lys Leu Ala Gly Asp Val Glu Ser Asn
1               5                   10                  15

Pro Gly Pro

<210> SEQ ID NO 35
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 35

Leu Leu Lys Leu Ala Gly Asp Val Glu Ser Asn Pro Gly Pro
1               5                   10

```
<210> SEQ ID NO 36
<211> LENGTH: 17
<212> TYPE: PRT
<213> ORGANISM: Artificial Sequence
<220> FEATURE:
<223> OTHER INFORMATION: Self-cleaving polypeptide comprising 2A site

<400> SEQUENCE: 36

Asn Phe Asp Leu Leu Lys Leu Ala Gly Asp Val Glu Ser Asn Pro Gly
1               5                   10                  15

Pro

<210> SEQ ID NO 37
<211> LENGTH: 20
<212> TYPE: PRT
<213> ORGANISM: Artificial Sequence
<220> FEATURE:
<223> OTHER INFORMATION: Self-cleaving polypeptide comprising 2A site

<400> SEQUENCE: 37

Gln Leu Leu Asn Phe Asp Leu Leu Lys Leu Ala Gly Asp Val Glu Ser
1               5                   10                  15

Asn Pro Gly Pro
            20

<210> SEQ ID NO 38
<211> LENGTH: 24
<212> TYPE: PRT
<213> ORGANISM: Artificial Sequence
<220> FEATURE:
<223> OTHER INFORMATION: Self-cleaving polypeptide comprising 2A site

<400> SEQUENCE: 38

Ala Pro Val Lys Gln Thr Leu Asn Phe Asp Leu Leu Lys Leu Ala Gly
1               5                   10                  15

Asp Val Glu Ser Asn Pro Gly Pro
            20

<210> SEQ ID NO 39
<211> LENGTH: 40
<212> TYPE: PRT
<213> ORGANISM: Artificial Sequence
<220> FEATURE:
<223> OTHER INFORMATION: Self-cleaving polypeptide comprising 2A site

<400> SEQUENCE: 39

Val Thr Glu Leu Leu Tyr Arg Met Lys Arg Ala Glu Thr Tyr Cys Pro
1               5                   10                  15

Arg Pro Leu Leu Ala Ile His Pro Thr Glu Ala Arg His Lys Gln Lys
            20                  25                  30

Ile Val Ala Pro Val Lys Gln Thr
        35                  40

<210> SEQ ID NO 40
<211> LENGTH: 18
<212> TYPE: PRT
<213> ORGANISM: Artificial Sequence
<220> FEATURE:
<223> OTHER INFORMATION: Self-cleaving polypeptide comprising 2A site

<400> SEQUENCE: 40

Leu Asn Phe Asp Leu Leu Lys Leu Ala Gly Asp Val Glu Ser Asn Pro
1               5                   10                  15

Gly Pro
```

-continued

```
<210> SEQ ID NO 41
<211> LENGTH: 40
<212> TYPE: PRT
<213> ORGANISM: Artificial Sequence
<220> FEATURE:
<223> OTHER INFORMATION: Self-cleaving polypeptide comprising 2A site

<400> SEQUENCE: 41

Leu Leu Ala Ile His Pro Thr Glu Ala Arg His Lys Gln Lys Ile Val
1               5                   10                  15

Ala Pro Val Lys Gln Thr Leu Asn Phe Asp Leu Leu Lys Leu Ala Gly
            20                  25                  30

Asp Val Glu Ser Asn Pro Gly Pro
        35                  40

<210> SEQ ID NO 42
<211> LENGTH: 33
<212> TYPE: PRT
<213> ORGANISM: Artificial Sequence
<220> FEATURE:
<223> OTHER INFORMATION: Self-cleaving polypeptide comprising 2A site

<400> SEQUENCE: 42

Glu Ala Arg His Lys Gln Lys Ile Val Ala Pro Val Lys Gln Thr Leu
1               5                   10                  15

Asn Phe Asp Leu Leu Lys Leu Ala Gly Asp Val Glu Ser Asn Pro Gly
            20                  25                  30

Pro

<210> SEQ ID NO 43
<211> LENGTH: 10
<212> TYPE: DNA
<213> ORGANISM: Artificial Sequence
<220> FEATURE:
<223> OTHER INFORMATION: Consensus Kozak sequence

<400> SEQUENCE: 43 gccrccatgg                                                          10

<210> SEQ ID NO 44
<211> LENGTH: 4
<212> TYPE: PRT
<213> ORGANISM: Artificial Sequence
<220> FEATURE:
<223> OTHER INFORMATION: Exemplary rule for determining light chain
      CDR-L3 motif
<220> FEATURE:
<221> NAME/KEY: MISC_FEATURE
<222> LOCATION: (3)..(3)
<223> OTHER INFORMATION: Xaa is any amino acid

<400> SEQUENCE: 44

Phe Gly Xaa Gly
1

<210> SEQ ID NO 45
<211> LENGTH: 4
<212> TYPE: PRT
<213> ORGANISM: Artificial Sequence
<220> FEATURE:
<223> OTHER INFORMATION: Exemplary rule for determining heavy chain
      CDR-H1 motif
<220> FEATURE:
<221> NAME/KEY: MISC_FEATURE
<222> LOCATION: (2)..(4)
```

```
<223> OTHER INFORMATION: Xaa is any amino acid

<400> SEQUENCE: 45

Cys Xaa Xaa Xaa
1

<210> SEQ ID NO 46
<211> LENGTH: 5
<212> TYPE: PRT
<213> ORGANISM: Artificial Sequence
<220> FEATURE:
<223> OTHER INFORMATION: Exemplary rule for determining heavy chain
      CDR-H2 motif

<400> SEQUENCE: 46

Leu Glu Trp Ile Gly
1               5

<210> SEQ ID NO 47
<211> LENGTH: 4
<212> TYPE: PRT
<213> ORGANISM: Artificial Sequence
<220> FEATURE:
<223> OTHER INFORMATION: Exemplary rule for determining heavy chain
      CDR-H3 motif
<220> FEATURE:
<221> NAME/KEY: MISC_FEATURE
<222> LOCATION: (3)..(3)
<223> OTHER INFORMATION: Xaa is any amino acid

<400> SEQUENCE: 47

Trp Gly Xaa Gly
1
```